United States Patent
Igawa et al.

(10) Patent No.: US 9,199,963 B2
(45) Date of Patent: Dec. 1, 2015

(54) HETEROCYCLIC COMPOUND

(71) Applicant: Takeda Pharmaceutical Company Limited, Osaka (JP)

(72) Inventors: Hideyuki Igawa, Kanagawa (JP); Masashi Takahashi, Kanagawa (JP); Keiko Kakegawa, Kanagawa (JP); Minoru Ikoma, Kanagawa (JP); Jumpei Aida, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 14/325,564

(22) Filed: Jul. 8, 2014

(65) Prior Publication Data

US 2015/0018373 A1 Jan. 15, 2015

(30) Foreign Application Priority Data

Jul. 9, 2013 (JP) .................................. 2013-143940

(51) Int. Cl.
| | | |
|---|---|---|
| C07D 401/00 | (2006.01) |
| A61K 31/4965 | (2006.01) |
| C07D 401/04 | (2006.01) |
| C07D 401/14 | (2006.01) |
| C07D 409/14 | (2006.01) |
| C07D 417/14 | (2006.01) |
| C07D 405/14 | (2006.01) |

(52) U.S. Cl.
CPC ............ *C07D 401/04* (2013.01); *C07D 401/14* (2013.01); *C07D 405/14* (2013.01); *C07D 409/14* (2013.01); *C07D 417/14* (2013.01)

(58) Field of Classification Search
None
See application file for complete search history.

(56) References Cited

U.S. PATENT DOCUMENTS

| 2004/0077628 A1 | 4/2004 | Ishihara et al. |
|---|---|---|
| 2009/0264426 A1 | 10/2009 | Sakuraba et al. |
| 2010/0184648 A1 | 7/2010 | Gomori et al. |
| 2015/0018363 A1* | 1/2015 | Kasai et al. ............. 514/252.04 |

FOREIGN PATENT DOCUMENTS

| JP | 10-262687 | 10/1998 |
|---|---|---|
| WO | 96/39162 | 12/1996 |
| WO | 99/28492 | 6/1999 |
| WO | 00/49170 | 8/2000 |
| WO | 01/82925 | 11/2001 |
| WO | 03/028641 | 4/2003 |
| WO | 03/063889 | 8/2003 |
| WO | 03/068230 | 8/2003 |
| WO | 2004/028453 | 4/2004 |
| WO | 2005/018557 | 3/2005 |
| WO | 2005/040824 | 5/2005 |
| WO | 2006/104136 | 10/2006 |
| WO | 2007/029847 | 3/2007 |
| WO | 2008/070599 | 6/2008 |
| WO | 2008/086404 | 7/2008 |
| WO | 2008/086409 | 7/2008 |
| WO | 2011/127643 | 10/2011 |
| WO | 2011/130086 | 10/2011 |
| WO | 2013/105676 | 7/2013 |

OTHER PUBLICATIONS

International Search Report issued Aug. 22, 2014 in International (PCT) Application No. PCT/JP2014/068651.
Written Opinion issued Aug. 22, 2014 in International (PCT) Application No. PCT/JP2014/068651.
Surman et al., "5-(Pyridinon-1-yl)indazoles and 5-(furopyridinon-5-yl)indazoles as MCH-1 antagonists", Bioorganic & Medicinal Chemistry Letters, vol. 20, No. 23, Sep. 16, 2010, pp. 7015-7019.

* cited by examiner

*Primary Examiner* — Heidi Reese
(74) *Attorney, Agent, or Firm* — Wenderoth, Lind & Ponack, L.L.P.

(57) ABSTRACT

Provided is a compound having a melanin-concentrating hormone receptor antagonistic action and is useful as an agent for the prophylaxis or treatment of obesity and the like. A compound represented by the formula (I):

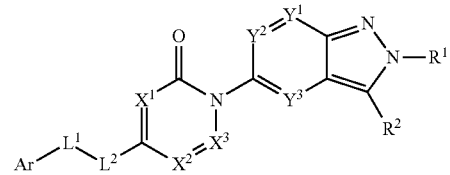

wherein each symbol is as defined in the specification, or a salt thereof.

20 Claims, No Drawings

HETEROCYCLIC COMPOUND

TECHNICAL FIELD

The present invention relates to a heterocyclic compound having melanin-concentrating hormone (hereinafter sometimes abbreviated as MCH) receptor antagonistic action, and useful as an agent for the prophylaxis or treatment of obesity and the like.

BACKGROUND OF THE INVENTION

MCH is a hypothalamus-derived hormone known to have an appetite increasing action. Furthermore, it has been reported that MCH knockout mouse behaves normally but shows a significantly decreased food intake amount and a lighter body weight as compared to normal mouse (Nature, vol. 396, page 670, 1998). Furthermore, MCH receptor-1-deficient mice have been reported to show a lean phenotype (Proc. Natl. Acad. Sci. USA, vol. 99, page 3240, 2002). Therefrom MCH receptor (particularly MCH receptor 1) antagonists are expected to be excellent appetite suppressants or anti-obesity agents.

As compounds having a MCH receptor antagonistic action, the following compounds are known.

1) WO 2007/029847 (patent document 1) discloses a pyridone derivative represented by the formula:

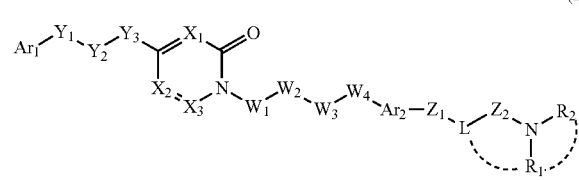

(I)

wherein $R_1$ and $R_2$ are the same or different and each is a hydrogen atom, a lower alkyl group optionally having substituent(s) or a lower cycloalkyl group optionally having substituent(s), or $R_1$ and $R_2$ form, together with the nitrogen atom bonded thereto, an aliphatic nitrogen-containing heterocycle optionally having substituent(s), $X_1$, $X_2$ and $X_3$ are the same or different and each is a methine group optionally having substituent(s) or a nitrogen atom, provided that $X_1$, $X_2$ and $X_3$ are not simultaneously nitrogen atoms, $Y_1$ is a single bond, —O—, —NR—, —S—, —SO— or —SO$_2$—, $Y_2$ is a lower alkylene group optionally having substituent(s), a lower alkenylene group optionally having substituent(s) or a lower cycloalkylene group optionally having substituent(s), $Y_3$ is a single bond, —O—, —NR—, —S—, —SO— or —SO$_2$—, each R is independently a hydrogen atom or a lower alkyl group optionally having substituent(s), $W_1$, $W_2$, $W_3$ and $W_4$ are the same or different and each is a single bond, a methylene group optionally having substituent(s) or —O—, provided that continuous two or more of $W_1$, $W_2$, $W_3$ and $W_4$ are not simultaneously —O—, L is a single bond, a methylene group optionally having substituent(s) or an ethylene group optionally having substituent(s), and L optionally forms, together with $Z_2$, $R_1$ and the nitrogen atom bonded to $R_1$, an aliphatic nitrogen-containing heterocycle optionally having substituent(s), $Z_1$ and $Z_2$ are the same or different, and each is a single bond, a $C_{1-4}$alkylene group optionally having substituent(s) or —O—, $Ar_1$ is an aromatic carbocyclic group optionally having substituent(s) or an aromatic heterocyclic group optionally having substituent(s), and $Ar_2$ is a divalent and bicyclic aromatic carbocyclic group optionally having substituent(s) or a divalent and bicyclic aromatic heterocyclic group optionally having substituent(s), or a pharmaceutically acceptable salt thereof.

2) WO 2008/086409 (patent document 2) discloses a compound represented by the formula:

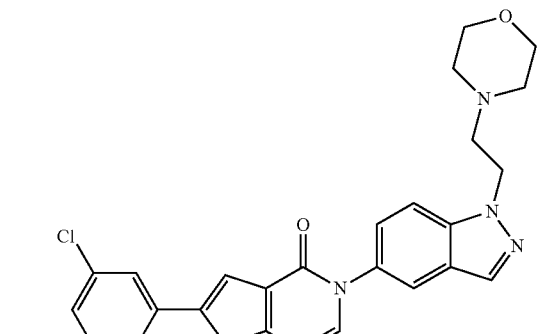

wherein n is 1 or 2,

R is $NR^1R^2$ wherein, $R^1$ and $R^2$ are each independently selected from H and optionally substituted alkyl, or $R^1$ and $R^2$ form, together with the adjacent N atom, a 4- to 7-membered optionally substituted heterocycle optionally containing 1 or 2 hetero atoms in addition to the N atom, $R^3$ and $R^4$ are each independently selected from H and alkyl, or R, $R^3$ and $R^4$ can form, in combination, optionally substituted imidazolin-2-yl, B is aryl or heteroaryl, and $R^5$, $R^6$ and $R^7$ are each independently selected from H, —OH, —O-alkyl, alkyl, halo, —CF$_3$ and —CN, provided the aforementioned compound is not one of the following

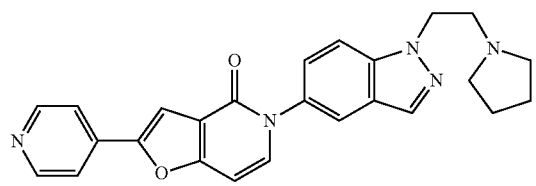

and

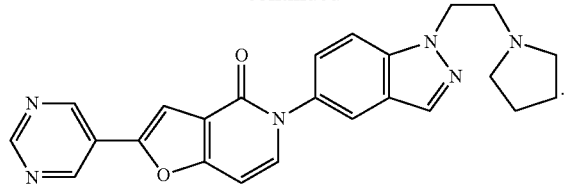

3) Bioorg. Med. Chem. Lett., 20(23), 7015-7019 (2010) (non-patent document 1) discloses a compound represented by the following formula:

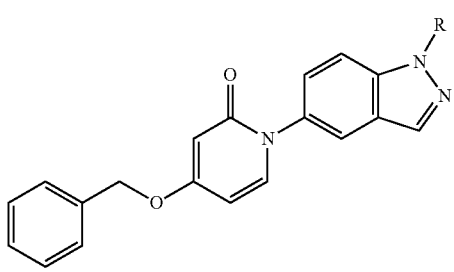

wherein R is 2-(dimethylamino)ethyl, 2-(pyrrolidin-1-yl)ethyl, (4,5-dihydro-1H-imidazol-2-yl)methyl or the like.

4) WO 2011/130086 (patent document 3) and WO 2011/127643 (patent document 4) disclose a compound represented by the formula:

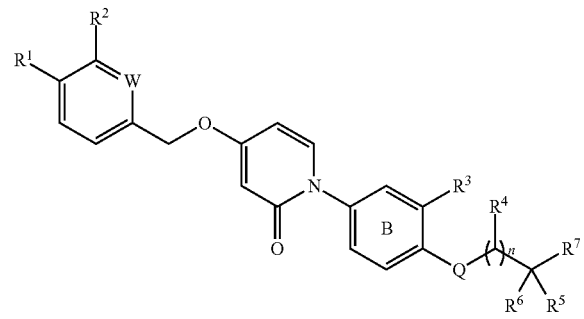

wherein
$R^1$ and $R^2$ are each independently selected from the group consisting of halogen, hydrogen, —OH, $C_1$-$C_6$ alkyl, —$OC_1$-$C_6$ alkyl, —O-halogen-substituted $C_1$-$C_6$ alkyl and halogen-substituted $C_1$-$C_6$ alkyl;
W is —N— or —CH—;
Q is —O—, —NH— or —C—, or forms heteroaryl together with $R^4$, aromatic ring B and $R^3$;
$R^3$ is halogen, hydrogen, —$OC_1$-$C_6$ alkyl, $C_1$-$C_6$ alkyl, —O-halogen substituted $C_1$-$C_6$ alkyl, halogen-substituted $C_1$-$C_6$ alkyl, cyano, $SO_2C_1$-$C_6$ alkyl or forms a heteroaryl ring together with aromatic ring B, Q and $R^4$;
$R^4$ is hydrogen, oxo, $C_1$-$C_6$ alkyl, halogen-substituted $C_1$-$C_6$ alkyl or forms heteroaryl together with aromatic ring B, $R^3$ and Q, or forms $C_3$-$C_6$ cycloalkyl together with $R^5$;
$R^5$, $R^6$ and $R^7$ are each independently selected from the group consisting of hydrogen, $C_1$-$C_6$ alkyl, halogen-substituted $C_1$-$C_6$ alkyl, $C_3$-$C_6$ cycloalkyl, halogen-substituted $C_3$-$C_6$ cycloalkyl, $C_1$-$C_6$ alkyl $C_3$-$C_6$ cycloalkyl, —OH, $C_1$-$C_6$ alkyl-OH and —$OC_1$-$C_6$ alkyl, or $R^5$ forms oxo group or $C_3$-$C_6$ cycloalkyl together with $R^6$, or $R^5$ forms $C_3$-$C_6$ cycloalkyl together with $R^4$, and at least one of $R^5$, $R^6$ and $R^7$ is not hydrogen, and
n is 1-3,
or a pharmaceutically acceptable salt thereof.

5) WO 01/82925 (patent document 5) discloses a compound represented by the formula:

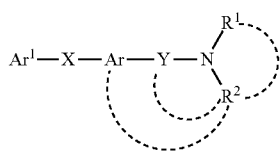

wherein
$Ar^1$ is a cyclic group optionally having substituent(s);
X and Y are the same or different and each is a spacer wherein the main chain has 1 to 6 atoms;
Ar is a fused polycyclic aromatic ring optionally having substituent(s);
$R^1$ and $R^2$ are the same or different and each is a hydrogen atom or a hydrocarbon group optionally having substituent(s), or $R^1$ and $R^2$ optionally form, together with the adjacent nitrogen atom, a nitrogen-containing heterocycle optionally having substituent(s), $R^2$ optionally form, together with the adjacent nitrogen atom and Y, a nitrogen-containing heterocycle optionally having substituent(s), and $R^2$ optionally form, together with the adjacent nitrogen atom, Y and Ar, a nitrogen-containing fused ring optionally having substituent(s),
or a salt thereof.

On the other hand, as a p38 MAP kinase modulator, the following compound is known.

6) WO 03/068230 (patent document 6) and WO 2005/018557 (patent document 7) disclose a compound represented by the formula:

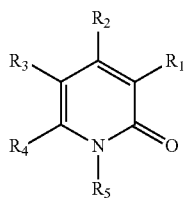

wherein
$R_1$ is H, halogen or the like,
$R_2$ is optionally substituted arylalkoxy, optionally substituted heteroarylalkyl or the like,
$R_3$ is H, halogen or the like,
$R_4$ is H or optionally substituted alkyl, and
$R_5$ is aryl optionally substituted by substituent(s) such as $C_3$-$C_7$ cycloalkyl, alkoxyalkyl and the like, and the like or a pharmaceutically acceptable salt thereof, and Example 641 discloses a compound represented by the following formula:

As the VEGF receptor 3 inhibitor, the following compound is known.

7) WO 2008/070599 (patent document 8) discloses a compound represented by the formula:

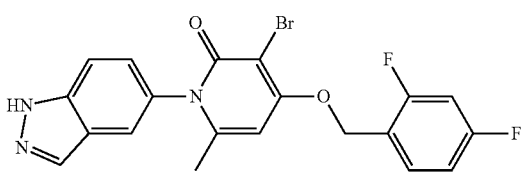

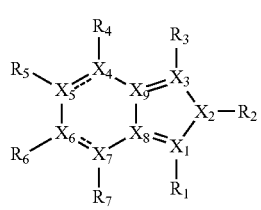
(I)

wherein $X_1$, $X_2$, $X_3$, $X_4$, $X_5$, $X_6$ and $X_7$ are each independently C or N, $X_8$ and $X_9$ are each independently C or $N^+$, $R_1$, $R_2$, $R_3$, $R_4$, $R_5$, $R_6$ and $R_7$ are each independently H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halogen, CN, $NO_2$, $OR_a$, $COOR_a$, $OC(O)R_a$, $C(O)R_a$, $C(O)NR_aR_b$, $C(O)N(R_a)N(R_b)C(O)R_c$, $NR_aR_b$, $N(R_c)SO_2NR_aR_b$, $SO_2NR_aR_b$, or $SR_a$, $R_a$, $R_b$ and $R_c$ are each independently H, $C_1$-$C_{10}$ alkyl, $C_3$-$C_{20}$ cycloalkyl, $C_1$-$C_{20}$ heterocycloalkyl, aryl or heteroaryl, or $R_a$ and $R_b$ form, together with the nitrogen atom bonded thereto, $C_1$-$C_{20}$ heterocycloalkyl or heteroaryl and, as compound 52, a compound represented by the following formula is disclosed.

Compound 52

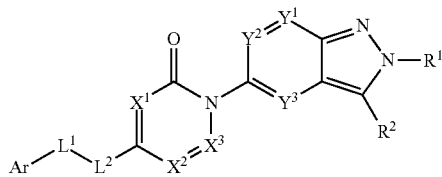

DOCUMENT LIST

Patent Documents patent document 1: WO 2007/029847
patent document 2: WO 2008/086409
patent document 3: WO 2011/130086
patent document 4: WO 2011/127643
patent document 5: WO 01/82925
patent document 6: WO 03/068230
patent document 7: WO 2005/018557
patent document 8: WO 2008/070599

Non-Patent Document non-patent document 1: Bioorg. Med. Chem. Lett., 20(23), 7015-7019 (2010)

SUMMARY OF THE INVENTION

Problems to be Solved by the Invention

The development of a compound having an MCH receptor antagonistic action and low toxicity, which is useful as an agent for the prophylaxis or treatment of obesity and the like is desired.

Means of Solving the Problems

The present inventors have conducted intensive studies of a compound having an MCH receptor antagonistic action, and found that compound (I) explained in the following has an excellent MCH receptor antagonistic action and shows low toxicity such as cardiotoxicity (e.g., human ether-a-go-go related gene (hERG) inhibitory activity), phospholipidosis (PLsis) inducing potential and the like, which resulted in the completion of the present invention.

Accordingly, the present invention relates to

[1] a compound represented by the formula (I):

wherein ring Ar is an aromatic ring optionally further substituted;

$L^1$ is O, $S(O)_{m1}$, $NR^{3A}$ or $CR^{3B}R^{3C}$;
$L^2$ is O, $S(O)_{m2}$, $NR^{4A}$ or $CR^{4B}R^{4C}$;
(excluding the combination of $L^1$ being other than $CR^{3B}R^{3C}$ and $L^2$ being other than $CR^{4B}R^{4C}$)
m1 and m2 are each independently an integer of 0 to 2;
$R^{3A}$ and $R^{4A}$ are each independently a hydrogen atom or an optionally substituted hydrocarbon group;
$R^{3B}$, $R^{3C}$, $R^{4B}$ and $R^{4C}$ are each independently a hydrogen atom or a substituent;
when $L^1$ is $CR^{3B}R^{3C}$ and ring Ar has substituent(s), $R^{3B}$ and the substituent are optionally bonded to each other to form an optionally substituted ring;
$X^1$, $X^2$ and $X^3$ are each independently $CR^5$ or N;
$R^5$ is a hydrogen atom, a halogen atom, a cyano group, an optionally substituted $C_{1-6}$alkyl group, an optionally substituted $C_{1-6}$alkoxy group or an optionally substituted $C_{3-10}$ cycloalkyl group;
$R^1$ is an optionally substituted $C_{1-6}$alkyl group or an optionally substituted cyclic group;
$R^2$ is a halogen atom, an optionally substituted $C_{1-6}$alkyl group or an optionally substituted cyclic group;
$Y^1$, $Y^2$ and $Y^3$ are each independently $CR^6$ or N; and
$R^6$ is a hydrogen atom, a halogen atom, an optionally substituted $C_{1-6}$alkyl group, an optionally substituted $C_{1-6}$ alkoxy group or an optionally substituted $C_{3-10}$ cycloalkyl group, or a salt thereof (hereinafter sometimes to be abbreviated as "compound (I)");

[2] the compound of the aforementioned [1], wherein ring Ar is a $C_{6-14}$ aromatic hydrocarbon ring or a 5- to 10-membered aromatic heterocycle, each of which is optionally further substituted by 1 to 3 substituents selected from
(a) a halogen atom,
(b) a $C_{1-6}$alkyl group optionally substituted by 1 to 3 halogen atoms,
(c) a $C_{1-6}$alkoxy group optionally substituted by 1 to 3 halogen atoms, and
(d) a pentafluorosulfanyl group, or a salt thereof;
[3] the compound of the aforementioned [1] or [2], wherein $L^1$ is $CH_2$; and $L^2$ is O, or a salt thereof;
[4] the compound of any one of the aforementioned [1] to [3], wherein $X^1$, $X^2$ and $X^3$ are CH, or a salt thereof;
[5] the compound of any one of the aforementioned [1] to [4], wherein $R^1$ is a $C_{1-6}$alkyl group or a $C_{3-10}$ cycloalkyl group, or a salt thereof;
[6] the compound of any one of the aforementioned [1] to [5], wherein $R^2$ is a $C_{1-6}$alkyl group, or a salt thereof;
[7] the compound of any one of the aforementioned [1] to [6], wherein $Y^1$, $Y^2$ and $Y^3$ are CH, or a salt thereof;
[8] the compound of the aforementioned [1], wherein ring Ar is a $C_{6-14}$ aromatic hydrocarbon ring or a 5- to 10-membered aromatic heterocycle, each of which is optionally further substituted by 1 to 3 substituents selected from
(a) a halogen atom,
(b) a $C_{1-6}$alkyl group optionally substituted by 1 to 3 halogen atoms,
(c) a $C_{1-6}$alkoxy group optionally substituted by 1 to 3 halogen atoms, and
(d) a pentafluorosulfanyl group,
$L^1$ is $CH_2$, $L^2$ is O,
$X^1$, $X^2$ and $X^3$ are CH,
$R^1$ is a $C_{1-6}$ alkyl group or a $C_{3-10}$ cycloalkyl group,
$R^2$ is a $C_{1-6}$ alkyl group, and
$Y^1$, $Y^2$ and $Y^3$ are CH, or a salt thereof;
[9] 4-[(4-chlorobenzyl)oxy]-1-(2,3-dimethyl-2H-indazol-5-yl)pyridin-2(1H)-one or a salt thereof;
[10] 1-(2-cyclopropyl-3-methyl-2H-indazol-5-yl)-4-{[5-(trifluoromethyl)thiophen-3-yl]methoxy}pyridin-2(1H)-one or a salt thereof;
[11] 1-(2-cyclopropyl-3-methyl-2H-indazol-5-yl)-4-{[2-(trifluoromethyl)-1,3-thiazol-4-yl]methoxy}pyridin-2(1H)-one or a salt thereof;
[12] a medicament comprising the compound of any one of the aforementioned [1] to [11] or a salt thereof;
[13] the medicament of the aforementioned [12], which is a melanin-concentrating hormone receptor antagonist;
[14] the medicament of the aforementioned [12], which is an anorexigenic agent;
[15] the medicament of the aforementioned [12], which is a prophylactic or therapeutic agent for obesity;
[16] a method of preventing or treating obesity in a mammal, comprising administering an effective amount of the compound of any one of the aforementioned [1] to [11] or a salt thereof to the mammal;
[17] a method of antagonizing a melanin-concentrating hormone receptor in a mammal, comprising administering an effective amount of the compound of any one of the aforementioned [1] to [11] or a salt thereof to the mammal;
[18] a method of suppressing food intake in a mammal, comprising administering an effective amount of the compound of any one of the aforementioned [1] to [11] or a salt thereof to the mammal;
[19] use of the compound of any one of the aforementioned [1] to [11] or a salt thereof for the production of a prophylactic or therapeutic agent for obesity;
[20] use of the compound of any one of the aforementioned [1] to [11] or a salt thereof for the production of an anorexigenic agent;
[21] the compound of any one of the aforementioned [1] to [11] or a salt thereof for use in the prophylaxis or treatment of obesity;
[22] the compound of any one of the aforementioned [1] to [11] or a salt thereof for use in the suppression of food intake; and the like.

Compound (I) has a high MCH receptor antagonistic action, and is low in toxicity such as cardiotoxicity (e.g., hERG inhibitory activity), PLsis inducing potential and the like, as compared to conventional MCH receptor antagonists. Therefore, compound (I) is useful as an agent for the prophylaxis or treatment of obesity and the like.

DETAILED DESCRIPTION OF THE INVENTION

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$alkyl group" include a $C_{1-6}$alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{7-16}$ aralkyl group" include benzyl, phenethyl, naphthylmethyl and phenylpropyl.

In the present specification, examples of the "$C_{1-6}$alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$alkoxy group" include a $C_{1-6}$alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$alkylthio group" include a $C_{1-6}$alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$alkyl-carbonyl group" include a $C_{1-6}$alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ arylcarbonyl group" include benzoyl, 1-naphthoyl and 2-naphthoyl.

In the present specification, examples of the "$C_{7-16}$ aralkylcarbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$alkyl group, a $C_{2-6}$alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$alkoxy-carbonyloxy group (e.g., methoxycarbonyloxy, ethoxycarbonyloxy, propoxycarbonyloxy, butoxycarbonyloxy),
(14) a mono- or di-$C_{1-6}$alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$alkyl group (e.g., phenylsulfonyloxy, toluenesulfonyloxy),
(20) an optionally halogenated $C_{1-6}$alkylthio group,
(21) a 5- to 14-membered aromatic heterocyclic group,

(22) a 3- to 14-membered non-aromatic heterocyclic group,
(23) a formyl group,
(24) a carboxy group,
(25) an optionally halogenated $C_{1-6}$alkyl-carbonyl group,
(26) a $C_{6-14}$ aryl-carbonyl group,
(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$alkyl-carbonylamino group (e.g., acetylamino, propanoylamino, butanoylamino),
(51) a ($C_{1-6}$alkyl) ($C_{1-6}$alkyl-carbonyl)amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$alkylsulfonylamino group (e.g., methylsulfonylamino, ethylsulfonylamino),
(56) a $C_{6-14}$ arylsulfonylamino group optionally substituted by a $C_{1-6}$alkyl group (e.g., phenylsulfonylamino, toluenesulfonylamino),
(57) an optionally halogenated $C_{1-6}$alkyl group,
(58) a $C_{2-6}$alkenyl group,
(59) a $C_{2-6}$alkynyl group,
(60) a $C_{3-10}$ cycloalkyl group,
(61) a $C_{3-10}$ cycloalkenyl group and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 hetero atoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 hetero atoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, 3-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 hetero atoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the aforementioned substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$alkyl group, a $C_{2-6}$alkenyl group, a $C_{3-10}$cycloalkyl group, a $C_{3-10}$cycloalkenyl group, a $C_{6-14}$aryl group, a $C_{7-16}$aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$alkyl-carbonyl group, a $C_{2-6}$alkenyl-carbonyl group (e.g., crotonoyl), a $C_{3-10}$cycloalkyl-carbonyl group (e.g., cyclobutanecarbonyl, cyclopentanecarbonyl, cyclohexanecarbonyl, cycloheptanecarbonyl), a $C_{3-10}$cycloalkenyl-carbonyl group (e.g., 2-cyclohexenecarbonyl), a $C_{6-14}$aryl-carbonyl group, a $C_{7-16}$aralkyl-carbonyl group, a 5- to 14-membered aromatic heterocyclylcarbonyl group, a 3- to 14-membered non-aromatic heterocyclylcarbonyl group, a $C_{1-6}$alkoxy-carbonyl group, a $C_{6-14}$aryloxy-carbonyl group (e.g., phenyloxycarbonyl, naphthyloxycarbonyl), a $C_{7-16}$aralkyloxy-carbonyl group (e.g., benzyloxycarbonyl, phenethyloxycarbonyl), a carbamoyl group, a mono- or di-$C_{1-6}$alkyl-carbamoyl group, a mono- or di-$C_{2-6}$alkenyl-carbamoyl group (e.g., diallylcarbamoyl), a mono- or di-$C_{3-10}$cycloalkyl-carbamoyl group (e.g., cyclopropylcarbamoyl), a mono- or di-$C_{6-14}$aryl-carbamoyl group (e.g., phenylcarbamoyl), a mono- or di-$C_{7-16}$aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted amino group include an amino group, a mono- or di-(optionally halogenated $C_{1-6}$alkyl)amino group (e.g., methylamino, trifluoromethylamino, dimethylamino, ethylamino, diethylamino, propylamino, dibutylamino), a mono- or di-$C_{2-6}$alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl)amino group (e.g., methylcarbamoylamino), a (mono- or di-$C_{7-16}$ aralkyl-carbamoyl)amino group (e.g., benzylcarbamoylamino), a $C_{1-6}$alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl) ($C_{1-6}$alkyl-carbonyl) amino group (e.g., N-acetyl-N-methylamino) and a ($C_{1-6}$alkyl) ($C_{6-14}$ aryl-carbonyl)amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$alkyl-carbamoyl group and a mono- or di-$C_{7-16}$ aralkyl-carbamoyl group, each of which optionally has 1 to 3 substituents selected from substituent group A".

Preferable examples of the optionally substituted carbamoyl group include a carbamoyl group, a mono- or di-$C_{1-6}$ alkyl-carbamoyl group, a mono- or di-$C_{2-6}$alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$alkenyl group, a $C_{3-10}$ cycloalkyl group, a $C_{6-14}$ aryl group, a $C_{7-16}$ aralkyl group, a $C_{1-6}$alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$alkyl-carbamoyl group and a mono- or di-$C_{7-16}$ aralkyl-carbamoyl group, each of which optionally has 1 to 3 substituents selected from substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$alkenyl group, a $C_{3-10}$ cycloalkyl group, a $C_{6-14}$ aryl group, a $C_{7-16}$ aralkyl group, a $C_{1-6}$alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$alkyl-carbamoyl group and a mono- or di-$C_{7-16}$ aralkyl-carbamoyl group, each of which optionally has 1 to 3 substituents selected from substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$alkenyl-sultamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxyl group optionally having "a substituent selected from a $C_{1-6}$alkyl group, a $C_{2-6}$ alkenyl group, a $C_{3-10}$ cycloalkyl group, a $C_{6-14}$ aryl group, a $C_{7-16}$ aralkyl group, a $C_{1-6}$alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from substituent group A".

Preferable examples of the optionally substituted hydroxy group include a hydroxy group, a $C_{1-6}$alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$alkyl-carbamoyloxy group (e.g., methylcarbamoyloxy), a $C_{1-16}$ aralkyl-carbamoyloxy group (e.g., benzylcarbamoyloxy), a $C_{1-6}$alkylsulfonyloxy group (e.g., methylsulfonyloxy, ethylsulfonyloxy) and a $C_{1-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$alkenyl group, a $C_{3-10}$ cycloalkyl group, a $C_{6-14}$ aryl group, a $C_{7-16}$ aralkyl group, a $C_{1-6}$alkyl-carbonyl group, a $C_{6-14}$ aryl-carbonyl group and a 5- to 14-membered aromatic heterocyclic group, each of which optionally has 1 to 3 substituents selected from substituent group A" and a halogenated sulfanyl group.

Preferable examples of the optionally substituted sulfanyl group include a sulfanyl (—SH) group, a $C_{1-6}$alkylthio group, a $C_{2-6}$alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$alkenyl group, a $C_{3-10}$ cycloalkyl group, a $C_{6-14}$ aryl group and a $C_{7-16}$ aralkyl group, each of which optionally has 1 to 3 substituents selected from substituent group A".

Preferable examples of the optionally substituted silyl group include a tri-$C_{1-6}$alkylsilyl group (e.g., trimethylsilyl, tert-butyl(dimethyl)silyl).

In the present specification, examples of the "ring" (including "ring" in the "optionally further substituted ring") include a hydrocarbon ring and heterocycle.

In the present specification, examples of the "ring" in the "optionally further substituted ring" optionally has 1 to (preferably, 1 to 3) substituents at substitutable position(s). When the number of the substituents is two or more, the respective substituents may be the same or different.

In the present specification, examples of the "hydrocarbon ring" include a $C_{6-14}$ aromatic hydrocarbon ring, $C_{3-10}$ cycloalkane and $C_{3-10}$ cycloalkene.

In the present specification, examples of the "$C_{6-14}$ aromatic hydrocarbon ring" include benzene and naphthalene.

In the present specification, examples of the "$C_{3-10}$ cycloalkane" include cyclopropane, cyclobutane, cyclopentane, cyclohexane, cycloheptane and cyclooctane.

In the present specification, examples of the "$C_{3-10}$ cycloalkene" include cyclopropene, cyclobutene, cyclopentene, cyclohexene, cycloheptene and cyclooctene.

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and 8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiine, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxathiine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepanine, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-3-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

"(60) a $C_{3-10}$ cycloalkyl group" in the above-mentioned substituent group A is optionally substituted by a cyano group.

"(22) a 3- to 14-membered non-aromatic heterocyclic group" in the above-mentioned substituent group A is optionally substituted by a $C_{1-6}$alkyl group.

"(6) an optionally halogenated $C_{1-6}$ alkoxy group" in the above-mentioned substituent group A is optionally substituted by a $C_{1-6}$alkoxy group.

In the present specification, examples of the "aromatic ring" (including "aromatic ring" in the "optionally further substituted aromatic ring") include a $C_{6-14}$ aromatic hydrocarbon ring and an aromatic heterocycle.

In the present specification, examples of the "aromatic ring" in the "optionally further substituted aromatic ring" optionally has 1 to 5, preferably, 1 to 3, substituents at substitutable position(s). When the number of the substituents is two or more, the respective substituents may be the same or different. The substituent also includes a sulfanyl group optionally substituted by 1 to 5 halogen atoms.

In the present specification, examples of the "optionally substituted $C_{1-6}$alkyl group" include an "optionally substituted hydrocarbon group" wherein the hydrocarbon group is a "$C_{1-6}$ alkyl group".

In the present specification, examples of the "optionally substituted $C_{3-10}$ cycloalkyl group" include an "optionally substituted hydrocarbon group" wherein the hydrocarbon group is a "$C_{3-10}$ cycloalkyl group".

In the present specification, examples of the "cyclic group" of the "optionally substituted cyclic group" include a "cyclic hydrocarbon group" and a "heterocyclic group".

Examples of the "cyclic hydrocarbon group" include a $C_{6-14}$ aryl group, a $C_{3-10}$ cycloalkyl group and a $C_{3-10}$ cycloalkenyl group.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "cyclic group" of the "optionally substituted cyclic group" optionally has 1 to 5, preferably 1 to 3 substituents, at substitutable position(s). When the number of the substituents is two or more, the respective substituents may be the same or different.

In the present specification, examples of the "$C_{1-6}$alkoxy group" of the "optionally substituted $C_{1-6}$alkoxy group" optionally has 1 to 5, preferably 1 to 3 substituents, at substitutable position(s). When the number of the substituents is two or more, the respective substituents may be the same or different.

In the above-mentioned formula (I), preferable groups are as described below.

Ring Ar is an optionally further substituted aromatic ring.

Ring Ar is, for example, an optionally further substituted $C_{6-14}$ aromatic hydrocarbon ring, an optionally further substituted 5- to 10-membered aromatic heterocycle (preferably, a 5- to 10-membered aromatic heterocycle containing, as a ring-constituting atom besides carbon atom, 1 to 4 hetero atoms selected from a nitrogen atom, a sulfur atom and an oxygen atom) and the like.

Ring Ar is preferably a $C_{6-14}$ aromatic hydrocarbon ring (e.g., benzene) optionally further substituted by 1 to 3 substituents selected from substituent group A, or a 5- to 10-membered aromatic heterocycle (preferably, a 5- to 10-membered aromatic heterocycle containing, as a ring-constituting atom besides carbon atom, 1 to 4 hetero atoms selected from a nitrogen atom, a sulfur atom and an oxygen atom, for example, pyridine, thiophene, thiazole, pyrazine, pyrazole, pyrimidine, furan, benzofuran, benzothiophene) optionally further substituted by 1 to 3 substituents selected from substituent group A.

Ring Ar is more preferably a $C_{6-14}$ aromatic hydrocarbon ring (e.g., benzene) or a 5- to 10-membered aromatic heterocycle (preferably, a 5- to 10-membered aromatic heterocycle containing, as a ring-constituting atom besides carbon atom, 1 to 4 hetero atoms selected from a nitrogen atom, a sulfur atom and an oxygen atom, for example, pyridine, thiophene, thiazole, pyrazine, pyrazole, pyrimidine, furan, benzofuran, benzothiophene), each of which is optionally further substituted by 1 to 3 substituents selected from
(a) a halogen atom,
(b) a $C_{1-6}$alkyl group optionally substituted by 1 to 3 halogen atoms,
(c) a $C_{1-6}$ alkoxy group optionally substituted by 1 to 3 halogen atoms, and
(d) a pentafluorosulfanyl group.

Ring Ar is further preferably a $C_{6-14}$ aromatic hydrocarbon ring (e.g., benzene) or a 5- to 10-membered aromatic heterocycle (preferably, a 5- to 10-membered aromatic heterocycle containing, as a ring-constituting atom besides carbon atom, 1 to 4 hetero atoms selected from a nitrogen atom, a sulfur atom and an oxygen atom, for example, pyridine, thiophene, thiazole, pyrazine, benzofuran, benzothiophene), each of which is optionally further substituted by 1 to 3 substituents selected from
(a) a halogen atom,
(b) a $C_{1-6}$alkyl group optionally substituted by 1 to 3 halogen atoms, and
(c) a pentafluorosulfanyl group.

$L^1$ is O, $S(O)_{m1}$, $NR^{3A}$ or $CR^{3B}R^{3C}$;
$L^2$ is O, $S(O)_{m2}$, $NR^{4A}$ or $CR^{4B}R^{4C}$;
(excluding the combination of $L^1$ being other than $CR^{3B}R^{3C}$ and $L^2$ being other than $CR^{4B}R^{4C}$)
m1 and m2 are each independently an integer of 0 to 2;
$R^{3A}$ and $R^{4A}$ are each independently a hydrogen atom or an optionally substituted hydrocarbon group; and
$R^{3B}$, $R^{3C}$, $R^{4B}$ and $R^{4C}$ are each independently a hydrogen atom or a substituent;
when $L^1$ is $CR^{3B}R^{3C}$ and ring Ar has substituent(s), $R^{3B}$ and the substituent are optionally bonded to form an optionally substituted ring.

Examples of the optionally substituted hydrocarbon group for $R^{3A}$ or $R^{4A}$ include a $C_{1-6}$alkyl group optionally substituted by 1 to 3 halogen atoms and the like.

$R^{3A}$ and $R^{4A}$ are each preferably a hydrogen atom.

Examples of the substituent for $R^{3B}$, $R^{3C}$, $R^{4B}$ or $R^{4C}$ include a halogen atom, a cyano group, a nitro group, an optionally substituted hydrocarbon group, an optionally substituted heterocyclic group, an optionally substituted hydroxy group, an optionally substituted sulfanyl group, an optionally substituted amino group, an acyl group and the like.

$R^{3B}$, $R^{3C}$, $R^{4B}$ and $R^{4C}$ are each preferably independently a hydrogen atom, a halogen atom, a cyano group, a nitro group, a hydroxy group, or a $C_{1-6}$alkyl group optionally substituted by 1 to 3 halogen atoms s.

$R^{3B}$, $R^{3C}$, $R^{4B}$ and $R^{4C}$ are more preferably each independently a hydrogen atom or a $C_{1-6}$alkyl group.

Examples of the optionally substituted ring, which is formed by $R^{3B}$ and the substituent of ring Ar bonded to each other, include an optionally substituted $C_{5-7}$cycloalkane (e.g., cyclopentane, cyclohexane) and the like. Examples of the substituent that $C_{5-7}$cycloalkane optionally has include a halogen atom, a cyano group, a nitro group, a hydroxy group, a $C_{1-6}$ alkyl group and the like.

Ar-$L^1$-$L^2$- when $R^{3B}$ and the substituent of ring Ar are bonded to each other to form an optionally substituted ring is, for example, a group represented by the formula

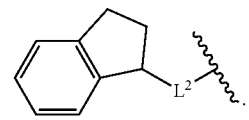

Preferable combinations of Ar-$L^1$-$L^2$- are, for example,
Ar—$CR^{3B}R^{3C}$—O—,
Ar—O—$CR^{4B}R^{4C}$—,
Ar—$CR^{3B}R^{3C}$—$CR^{4B}R^{4C}$—,
Ar—$CH_2$—$NR^{4A}$—
and the like, more preferably
Ar—$CH_2$—O—,
Ar—O—$CH_2$—,
Ar—$CH(CH_3)$—O—,
Ar—$CH_2$—NH—,
Ar—$CH_2$—$N(CH_3)$—,
Ar—$CH_2$—$CH_2$—,

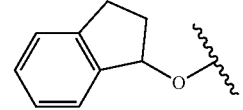 [SMILES: *OC1CCc2ccccc21]

and the like.
More preferably,
$L^1$ is $CH_2$ and $L^2$ is O, or
$L^1$ is O and $L^2$ is $CH_2$.
Particularly preferably, $L^1$ is $CH_2$ and $L^2$ is O.

$X^1$, $X^2$ and $X^3$ are each independently $CR^5$ or N; and $R^5$ is a hydrogen atom, a halogen atom, a cyano group, an optionally substituted $C_{1-6}$alkyl group, an optionally substituted $C_{1-6}$alkoxy group or an optionally substituted $C_{3-10}$cycloalkyl group.

$R^5$ is preferably
a hydrogen atom,
a halogen atom,
a cyano group,
a $C_{1-6}$alkyl group optionally substituted by 1 to 3 substituents selected from substituent group A, a $C_{1-6}$alkoxy group optionally substituted by 1 to 3 substituents selected from substituent group A, or a $C_{3-10}$ cycloalkyl group optionally substituted by 1 to 3 substituents selected from substituent group A.

$R^5$ is more preferably a hydrogen atom, a halogen atom, a cyano group, a $C_{1-6}$alkyl group, a $C_{1-6}$alkoxy group or a $C_{3-10}$ cycloalkyl group.

$R^5$ is more preferably a hydrogen atom.

In preferable combinations of $X^1$, $X^2$ and $X^3$, $X^1$, $X^2$ and $X^3$ are CH;

$X^2$ and $X^3$ are CH, and $X^1$ is N;

$X^1$ and $X^3$ are CH, and $X^2$ is N; or $X^1$ and $X^2$ are CH, and $X^3$ is N.

More preferably, $X^1$, $X^2$ and $X^3$ are CH.

$R^1$ is an optionally substituted $C_{1-6}$alkyl group, or an optionally substituted cyclic group.

Examples of the "cyclic group" of the "optionally substituted cyclic group" for $R^1$ include a $C_{3-10}$ cycloalkyl group, a $C_{6-14}$ aryl group, a heterocyclic group and the like. As the heterocyclic group, a 4- to 6-membered heterocyclic group containing, besides carbon atom, 1 to 4 hetero atoms selected from a nitrogen atom, a sulfur atom and an oxygen atom and the like can be mentioned.

$R^1$ is preferably a $C_{1-6}$alkyl group optionally substituted by 1 to 3 substituents selected from substituent group A, or a $C_{3-10}$ cycloalkyl group optionally substituted by 1 to 3 substituents selected from substituent group A.

$R^1$ is more preferably (1) a $C_{1-6}$alkyl group optionally substituted by 1 to 3 substituents selected from (a) a $C_{1-6}$alkoxy group optionally substituted by 1 to 3 $C_{1-6}$alkoxy groups, (b) a $C_{3-10}$ cycloalkyl group (e.g., cyclopropyl) optionally substituted by 1 to 3 cyano groups, and (c) a non-aromatic heterocyclic group (preferably, a 4- to 6-membered non-aromatic heterocyclic group containing, as a ring-constituting atom besides carbon atom, 1 or 2 oxygen atoms, for example, oxetanyl) optionally substituted by 1 to 3 $C_{1-6}$alkyl groups, or (2) a $C_{3-10}$ cycloalkyl group (e.g., cyclopropyl).

$R^1$ is more preferably a $C_{1-6}$alkyl group or a $C_{3-10}$ cycloalkyl group.

$R^2$ is a halogen atom, an optionally substituted $C_{1-6}$alkyl group or an optionally substituted cyclic group.

Examples of the "cyclic group" of the "optionally substituted cyclic group" for $R^2$ include a $C_{3-10}$ cycloalkyl group, a $C_{6-14}$ aryl group, a heterocyclic group and the like. As the heterocyclic group, a 4- to 6-membered heterocyclic group containing, besides carbon atom, 1 to 4 hetero atoms selected from a nitrogen atom, a sulfur atom and an oxygen atom and the like can be mentioned.

$R^2$ is preferably a halogen atom, a $C_{1-6}$alkyl group optionally substituted by 1 to 3 substituents selected from substituent group A, or a $C_{3-10}$ cycloalkyl group optionally substituted by 1 to 3 substituents selected from substituent group A.

$R^2$ is more preferably a $C_{1-6}$alkyl group optionally substituted by 1 to 3 substituents selected from a halogen atom, a hydroxy group and a $C_{1-6}$alkoxy group.

$R^2$ is further preferably a $C_{1-6}$alkyl group optionally substituted by 1 to 3 substituents selected from a hydroxy group and a $C_{1-6}$alkoxy group.

$R^2$ is particularly preferably a $C_{1-6}$alkyl group (e.g., methyl).

$Y^1$, $Y^2$ and $Y^3$ are each independently $CR^6$ or N; and $R^6$ is a hydrogen atom, a halogen atom, an optionally substituted $C_{1-6}$alkyl group, an optionally substituted $C_{1-6}$ alkoxy group or an optionally substituted $C_{3-10}$ cycloalkyl group.

$R^6$ is preferably a hydrogen atom, a halogen atom, a $C_{1-6}$alkyl group optionally substituted by 1 to 3 substituents selected from substituent group A, a $C_{1-6}$ alkoxy group optionally substituted by 1 to 3 substituents selected from substituent group A, or a $C_{3-10}$ cycloalkyl group optionally substituted by 1 to 3 substituents selected from substituent group A.

$R^6$ is more preferably a hydrogen atom, a halogen atom, a $C_{1-6}$alkyl group, a $C_{1-6}$alkoxy group or a $C_{3-10}$ cycloalkyl group.

$R^6$ is further preferably a hydrogen atom or a halogen atom (e.g., a fluorine atom).

$Y^1$, $Y^2$ and $Y^3$ are preferably $CR^6$; and each $R^6$ is independently a hydrogen atom or a halogen atom (e.g., a fluorine atom).

$Y^1$, $Y^2$ and $Y^3$ are more preferably CH.

Preferable examples of compound (I) include the following compounds.

[Compound (I-A)]

Compound (I) wherein ring Ar is benzene, pyridine, pyrazine, thiophene, thiazole, benzofuran or benzothiophene, each of which is optionally further substituted by 1 to 3 substituents selected from (a) a halogen atom (e.g., a chlorine atom, a fluorine atom, a bromine atom), (b) a $C_{1-6}$alkyl group optionally substituted by 1 to 3 halogen atoms (e.g., a fluorine atom), and (c) a pentafluorosulfanyl group;

$L^1$ is $CH_2$ and $L^2$ is O, or $L^1$ is O and $L^2$ is $CH_2$;

$X^1$, $X^2$ and $X^3$ are CH;

$R^1$ is (1) a $C_{1-6}$alkyl group optionally substituted by 1 to 3 substituents selected from (a) a $C_{1-6}$alkoxy group optionally substituted by 1 to 3 $C_{1-6}$alkoxy groups, (b) a $C_{3-10}$ cycloalkyl group (e.g., cyclopropyl) optionally substituted by 1 to 3 cyano groups, and (c) a non-aromatic heterocyclic group (preferably, a 4- to 6-membered non-aromatic heterocyclic group containing, as a ring-constituting atom besides carbon atom, 1 or 2 oxygen atoms, for example, oxetanyl) optionally substituted by 1 to 3 $C_{1-6}$alkyl groups, or (2) a $C_{3-10}$ cycloalkyl group (e.g., cyclopropyl);

$R^2$ is a $C_{1-6}$alkyl group;

$Y^1$, $Y^2$ and $Y^3$ are $CR^6$; and each $R^6$ is independently a hydrogen atom or a halogen atom (e.g., a fluorine atom), or a salt thereof.

[Compound (I-B)]

Compound (I) wherein ring Ar is benzene, pyridine, pyrazine, thiophene, thiazole, benzofuran or benzothiophene, each of which is optionally substituted by 1 to 3 substituents selected from (a) a halogen atom (e.g., a chlorine atom, a fluorine atom, a bromine atom), (b) a $C_{1-6}$alkyl group optionally substituted by 1 to 3 halogen atoms (e.g., a fluorine atom), and (c) a pentafluorosulfanyl group;

L is $CH_2$ and $L^2$ is O;

$X^1$, $X^2$ and $X^3$ are CH;

$R^1$ is (1) a $C_{1-6}$ alkyl group optionally substituted by 1 to 3 substituents selected from (a) a $C_{1-6}$ alkoxy group optionally substituted by 1 to 3 $C_{1-6}$ alkoxy groups, (b) a $C_{3-10}$ cycloalkyl group (e.g., cyclopropyl) optionally substituted by 1 to 3 cyano groups, and (c) a 4- to 6-membered non-aromatic heterocyclic group containing, as a ring-constituting atom besides carbon atom, 1 or 2 oxygen atoms (preferably oxetanyl), which is optionally substituted by 1 to 3 $C_{1-6}$ alkyl groups, or (2) a $C_{3-10}$ cycloalkyl group (e.g., cyclopropyl);

$R^2$ is a $C_{1-6}$ alkyl group; and $Y^1$, $Y^2$ and $Y^3$ are CH, or a salt thereof.

[Compound (I-C)]

Compound (I) wherein ring Ar is a $C_{6-14}$ aromatic hydrocarbon ring (e.g., benzene) or a 5- to 10-membered aromatic heterocycle (e.g., pyridine, thiophene, thiazole, pyrazine, pyrazole, pyrimidine, furan, benzofuran, benzothiophene), each of which is optionally further substituted by 1 to 3 substituents selected from (a) a halogen atom (e.g., chlorine atom, fluorine atom, bromine atom), (b) a $C_{1-6}$ alkyl group optionally substituted by 1 to 3 halogen atoms (e.g., fluorine atom), (c) a $C_{1-6}$ alkoxy group optionally substituted by 1 to 3 halogen atoms (e.g., fluorine atom), and (d) a pentafluorosulfanyl group;

$L^1$ is $CH_2$, $L^2$ is O;

$X^1$, $X^2$ and $X^3$ are CH;

$R^1$ is a $C_{1-6}$ alkyl group or a $C_{3-10}$ cycloalkyl group (e.g., cyclopropyl);

$R^2$ is a $C_{1-6}$ alkyl group (e.g., methyl); and $Y^1$, $Y^2$ and $Y^3$ are CH, or a salt thereof.

[Compound (I-D)]

Compound (I) wherein ring Ar is benzene or a 5- to 10-membered aromatic heterocycle (e.g., pyridine, pyrazine, thiophene, thiazole, benzofuran, benzothiophene), each of which is optionally substituted by 1 to 3 substituents selected from (a) a halogen atom (e.g., a chlorine atom, a fluorine atom, a bromine atom), (b) a $C_{1-6}$ alkyl group optionally substituted by 1 to 3 halogen atoms (e.g., a fluorine atom), and (c) a pentafluorosulfanyl group;

$L^1$ is $CH_2$ and $L^2$ is O;

$X^1$, $X^2$ and $X^3$ are CH;

$R^1$ is a $C_{1-6}$ alkyl group or a $C_{3-10}$ cycloalkyl group (e.g., cyclopropyl);

$R^2$ is a $C_{1-6}$ alkyl group (e.g., methyl); and $Y^1$, $Y^2$ and $Y^3$ are CH, or a salt thereof.

[Compound (I-E)]

Compound (I) wherein ring Ar is benzene or a 5- or 6-membered aromatic heterocycle (e.g., pyridine, pyrazine, thiophene, thiazole), each of which is optionally substituted by 1 to 3 substituents selected from (a) a halogen atom (e.g., a chlorine atom, a fluorine atom, a bromine atom), (b) a $C_{1-6}$ alkyl group optionally substituted by 1 to 3 halogen atoms (e.g., a fluorine atom), and (c) a pentafluorosulfanyl group;

$L^1$ is $CH_2$ and $L^2$ is O;

$X^1$, $X^2$ and $X^3$ are CH;

$R^1$ is a $C_{1-6}$ alkyl group or a $C_{3-10}$ cycloalkyl group (e.g., cyclopropyl);

$R^2$ is a $C_{1-6}$ alkyl group (e.g., methyl); and $Y^1$, $Y^2$ and $Y^3$ are CH, or a salt thereof.

[Compound (I-F)]

Compound (I) wherein ring Ar is benzene, pyridine, thiophene, thiazole or benzofuran, each of which is optionally substituted by 1 to 3 substituents selected from (a) a halogen atom (e.g., a chlorine atom, a fluorine atom, a bromine atom), and (b) a $C_{1-6}$ alkyl group optionally substituted by 1 to 3 halogen atoms (e.g., a fluorine atom), $L^1$ is $CH_2$ and $L^2$ is O;

$X^1$, $X^2$ and $X^3$ are CH;

$R^1$ is a $C_{1-6}$ alkyl group or a $C_{3-10}$ cycloalkyl group (e.g., cyclopropyl);

$R^2$ is a $C_{1-6}$ alkyl group (e.g., methyl); and $Y^1$ and $Y^2$ are CH;

$Y^3$ is $CR^6$; and $R^6$ is a hydrogen atom or a halogen atom (e.g., a fluorine atom), or a salt thereof.

[Compound (I-G)]

Compound (I) wherein ring Ar is benzene, pyridine, thiophene or thiazole, each of which is optionally substituted by 1 to 3 substituents selected from (a) a halogen atom (e.g., a chlorine atom, a fluorine atom, a bromine atom), and (b) a $C_{1-6}$ alkyl group optionally substituted by 1 to 3 halogen atoms (e.g., a fluorine atom), $L^1$ is $CH_2$ and $L^2$ is O;

$X^1$, $X^2$ and $X^3$ are CH;

$R^1$ is a $C_{1-6}$ alkyl group or a $C_{3-10}$ cycloalkyl group (e.g., cyclopropyl);

$R^2$ is a $C_{1-6}$ alkyl group (e.g., methyl); and $Y^1$, $Y^2$ and $Y^3$ are CH, or a salt thereof.

[Compound (I-H)]

4-[(4-Chlorobenzyl)oxy]-1-(2,3-dimethyl-2H-indazol-5-yl)pyridin-2(1H)-one or a salt thereof.

1-(2-Cyclopropyl-3-methyl-2H-indazol-5-yl)-4-{[5-(trifluoromethyl)thiophen-3-yl]methoxy}pyridin-2(1H)-one or a salt thereof.

1-(2-Cyclopropyl-3-methyl-2H-indazol-5-yl)-4-{[2-(trifluoromethyl)-1,3-thiazol-4-yl]methoxy}pyridin-2(1H)-one or a salt thereof.

More preferable examples of compound (I) include those described in the following Examples and salts thereof.

When compound (I) is in the form of a salt, concrete examples thereof include pharmaceutically acceptable salts, for example, salts with inorganic bases, ammonium salts, salts with organic bases, salts with inorganic acids, salts with organic acids, salts with basic or acidic amino acids and the like.

Preferable examples of the salts with inorganic bases include alkali metal salts such as sodium salt, potassium salt, and the like; alkaline earth metal salts such as calcium salts, magnesium salts, barium salts, and the like; aluminum salts, and the like.

Preferable examples of the salts with organic bases include salts with trimethylamine, triethylamine, pyridine, picoline, ethanolamine, diethanolamine, triethanolamine, dicyclohexylamine, N,N'-dibenzylethylenediamine, and the like.

Preferable examples of the salts with inorganic acids include salts with hydrochloric acid, hydrobromic acid, nitric acid, sulfuric acid, phosphoric acid, and the like.

Preferable examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like.

Preferable examples of the salts with basic amino acids include salts with arginine, lysine, ornithine, and the like.

Preferable examples of the salts with acidic amino acids include salts with aspartic acid, glutamic acid, and the like.

Compound (I) may be any of an anhydrate or a hydrate.

In addition, compound (I) may be any of non-solvate and solvate.

Moreover, compound (I) may be labeled with an isotope (e.g., $^3H$, $^{11}C$, $^{14}C$, $^{18}F$, $^{35}S$, $^{125}I$)

Furthermore, compound (I) may also be a deuterated compound wherein $^1H$ is converted to $^2H(D)$.

Compound (I) labeled with or substituted by an isotope can be used, for example, as a tracer used for Positron Emission Tomography (PET) (PET tracer), and is useful in the field of medical diagnosis and the like.

Compound (I) may be a pharmaceutically acceptable cocrystal or a cocrystal salt. Here, the cocrystal or cocrystal salt means a crystalline substance, which is constituted from two or more kinds of specific solids each having different physical properties (e.g., structure, melting point, heat of fusion, hygroscopicity, solubility, stability etc.) at room temperature. The cocrystal and cocrystal salt can be produced according to a cocrystallization method known per se.

When compound (I) contains an optical isomer, a stereoisomer, a regioisomer or a rotamer, these are also encompassed in compound (I), and can be obtained as a single product according to synthesis and separation methods known per se. For example, when compound (I) has an optical isomer, an optical isomer resolved from this compound is also encompassed in compound (I).

The optical isomer can be produced by a method known per se (e.g., a fractional recrystallization method, a chiral column method, a diastereomer method).

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine) is formed, which is separated by a fractional recrystallization method, and if desired, a free optical isomer is obtained by a neutralization step.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer) and organic solvents (e.g., ethanol, methanol, isopropanol, acetonitrile, trifluoroacetic acid, diethylamine) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., fractional recrystallization, a chromatography method) and the like, and is subjected to a chemical treatment such as hydrolysis and the like to separate an optically active reagent moiety, whereby an optical isomer is obtained. For example, when compound (I) contains a hydroxy group, or a primary or secondary amino group in a molecule, the compound and an optically active organic acid (e.g., MTPA [a-methoxy-a-(trifluoromethyl)phenylacetic acid], (−)-menthoxyacetic acid) and the like are subjected to condensation reaction to give diastereomers in the ester form or in the amide form, respectively. When compound (I) has a carboxyl group, this compound and an optically active amine or alcohol are subjected to condensation reaction to give diastereomers in the amide form or in the ester form, respectively. The separated diastereomer is converted to an optical isomer of the original compound by acid hydrolysis or base hydrolysis.

Compound (I) may be a prodrug, and a prodrug of compound (I) means a compound which is converted to compound (I) with a reaction due to an enzyme, a gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc.

A prodrug of compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation);

a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation or dimethylaminomethylcarbonylation);

a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like.

Any of these compounds can be produced from compound (I) by a method known per se.

A prodrug of compound (I) may also be one which is converted into compound (I) under a physiological condition, such as those described in IYAKUHIN no KAIHATSU (Development of Pharmaceuticals), Vol. 7, Design of Molecules, p. 163-198, published by HIROKAWA SHOTEN (1990).

The production methods of compound (I) are explained in the following.

Compound (I) can be produced by, for example, a method shown below or a method analogous thereto, though not limited thereto.

In each of the following schemes, each starting compound may form a salt as long as it does not inhibit the reaction and, as the salt, those exemplified as the salt of the compound represented by the aforementioned formula (I) is used.

In each of the following schemes, as the starting compound, unless specific production method is stated, a commercially available one is easily available, or can be produced by a method known per se or a method analogous thereto.

A solvent to be used for the reaction of each of the following schemes is not particularly limited as long as it does not inhibit the reaction and dissolves the starting material to some extent. Examples thereof include aromatic hydrocarbons such as benzene, toluene, xylene and the like; aliphatic hydrocarbons such as hexane, heptane and the like; ethers such as diethyl ether, diisopropyl ether, tert-butyl methyl ether, tetrahydrofuran, 1,4-dioxane, 1,2-dimethoxyethane and the like; ketones such as acetone, 2-butanone and the like; nitriles such as acetonitrile, propionitrile and the like; esters such as ethyl acetate, isopropyl acetate, tert-butyl acetate and the like; amides such as N,N-dimethylformamide, N,N-dimethylacetamide, 1-methyl-2-pyrrolidinone and the like; imides such as 1,3-dimethyl-2-imidazolidinone and the like; alcohols such as methanol, ethanol, propanol, isopropanol, tert-butanol and the like; halogenated hydrocarbons such as chloroform, dichloromethane, 1,2-dichloroethane, carbon tetrachloride and the like; sulfoxides such as dimethyl sulfoxide and the like; water and the like. These solvents may be mixed and used at an appropriate ratio. The reaction temperature is not higher than the boiling points of the aforementioned solvents, and is generally −100° C. to 250° C. In some cases, pressure-resistant reaction conditions and the like may be employed, and the reaction may be performed at a temperature not lower than the boiling point of the solvent. The reaction time is generally 0.5 hr to 100 hr.

In each of the following reactions, the "room temperature" means 10° C. to 35° C.

Compound (I) can be produced, for example, by the reaction of compound (2) and compound (3) shown in the following production method 1-1.

[Production Method 1-1]

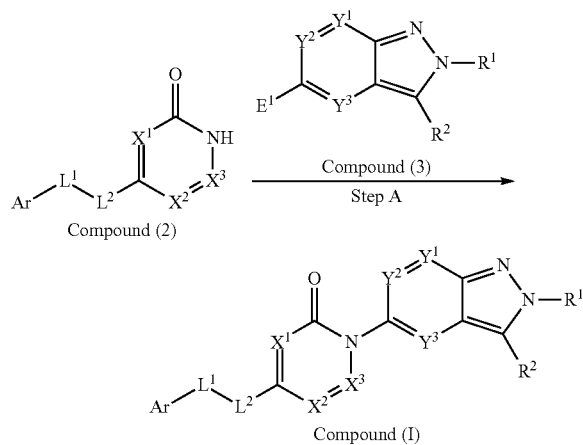

Compound (2)

Compound (I)

wherein each symbol is as defined above, $E^1$ is a leaving group (e.g., a halogen atom such as a chlorine atom, a bromine atom, an iodine atom and the like, a substituted sulfonyloxy group such as methanesulfonyloxy, p-toluenesulfonyloxy and the like, a boronic acid group etc.).

That is, in production method 1-1, compound (I) is obtained using about 1.0 to 10.0 mol, preferably about 1.0 to 5.0 mol, of compound (3), about 1.0 to 10.0 mol, preferably about 1.0 to 5.0 mol, of a base, and about 0.000001 to 5 mol, preferably about 0.0001 mol to 2 mol, of a metal catalyst, per 1 mol of compound (2).

Examples of the base include inorganic salts such as potassium carbonate, sodium carbonate, cesium carbonate, tripotassium phosphate and the like; amines such as pyridine, triethylamine, N,N-dimethylaniline, 1,8-diazabicyclo[5.4.0]undec-7-ene and the like; and the like. Two or more kinds of these bases may be mixed and used at an appropriate ratio.

Examples of the metal catalyst include copper and a salt thereof (e.g., copper(II) acetate, copper(I) iodide and the like), palladium complexes (e.g., palladium acetate, palladium chloride, tetrakis(triphenylphosphine)palladium, dichlorobis(triphenylphosphine)palladium, [1,1'-bis(diphenylphosphino)ferrocene]dichloropalladium and the like), nickel compounds (e.g., tetrakis(triphenylphosphine)nickel and the like), rhodium compounds (e.g., tris(triphenylphosphine)rhodium chloride and the like), platinum compounds and the like. Of these, copper and a salt thereof are preferable.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether, 1,2-dimethoxyethane and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; and the like. Two or more kinds of these solvents may be mixed and used at an appropriate ratio.

The reaction time is generally 15 min to 60 hr, preferably 30 min to 24 hr. The reaction temperature is from room temperature to 250° C., preferably 50° C. to 200° C. This reaction may be performed in a microwave reactor, for which the reaction time is generally 5 min to 24 hr, preferably 30 min to 2 hr. The reaction temperature is generally from room temperature to 250° C., preferably 50° C. to 200° C.

In addition, this reaction may be performed using a ligand. As the ligand, organic amine compounds such as N,N'-dimethylethylenediamine, N,N'-dimethyl-cyclohexane-1,2-diamine, 2,2-bipyridyl and the like; organic phosphorus compounds such as triphenylphosphine, tri-tert-butylphosphine, tricyclohexylphosphine, BINAP (2,2'-bis(diphenylphosphino)-1,1'-binaphthyl) and the like can be mentioned. The amount of the ligand to be used is generally about 1.0 to 10.0 mol, preferably about 1.0 to 5.0 mol, relative to the metal catalyst.

The obtained compound (I) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (2) may be a commercially available reagent, or can be produced by the method described in the following production method or a method analogous thereto, or can be produced by a method known per se.

Compound (3) can be produced by the method described in the following production method or a method analogous thereto.

Compounds (Ib) and (Ib'), which are compounds (I) wherein $L^1$ is $CR^{3B}R^{3C}$, and $L^2$ is O, $S(O)_{m2}$ or $NR^{4A}$, can also be produced by, for example, the reaction of compound (4) and compound (5) shown in the following production method 1-2 and, where necessary, a subsequent oxidation reaction.

[Production Method 1-2]

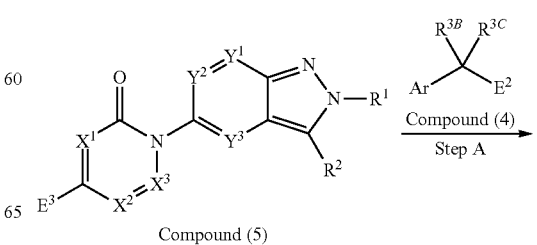

Compound (5)

-continued

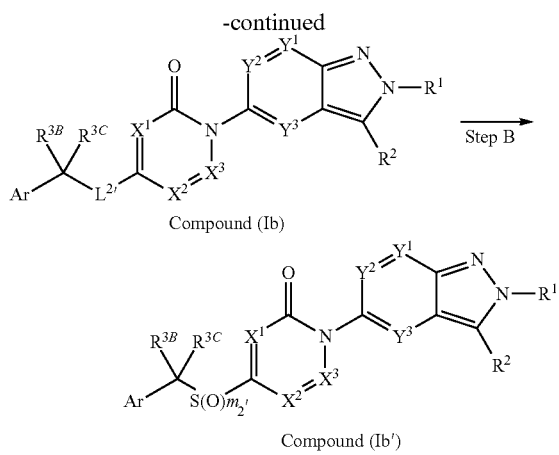

Compound (Ib)

Compound (Ib')

wherein $E^2$ is a leaving group (e.g., a halogen atom such as a chlorine atom, a bromine atom and the like, a substituted sulfonyloxy group such as methanesulfonyloxy, p-toluenesulfonyloxy and the like), a hydroxy group, $NR^{4A}H$ or SH, $E^3$ is a leaving group (e.g., a halogen atom such as a chlorine atom, a bromine atom and the like, a substituted sulfonyloxy group such as methanesulfonyloxy, p-toluenesulfonyloxy and the like) or a hydroxy group, $L^{2'}$ is O, S or $NR^{4A}$, m2' is an integer of 1 or 2, and other symbols are each as defined above. However, one of $E^2$ and $E^3$ is a leaving group, or they are simultaneously hydroxy groups, and Step B is present only when $L^{2'}$ is S.

<Step A>

When $E^2$ is a leaving group and $E^3$ is a hydroxy group, or $E^3$ is a leaving group and $E^2$ is a hydroxy group, $NR^{4A}H$ or SH, compound (Ib) can be produced using about 1.0 to 10.0 mol, preferably about 1.0 to 3.0 mol, of compound (4) and about 1.0 to 10.0 mol, preferably about 1.0 to 5.0 mol, of a base, per 1 mol of compound (5).

Examples of the base include inorganic salts such as sodium hydride, potassium carbonate, sodium carbonate, cesium carbonate and the like; metal alkoxides such as sodium methoxide, sodium ethoxide, potassium tert-butoxide and the like; amines such as pyridine, triethylamine, diisopropylethylamine, N,N-dimethylaniline, 1,8-diazabicyclo[5.4.0]undec-7-ene and the like, and the like. Two or more kinds of these bases may be mixed and used at an appropriate ratio.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide, N,N-dimethylacetamide and the like; sulfoxides such as dimethyl sulfoxide and the like; water and the like. Two or more kinds of these solvents may be mixed and used at an appropriate ratio.

The reaction time is generally 15 min to 60 hr, preferably 15 min to 24 hr. The reaction temperature is generally –20° C. to 150° C., preferably 0° C. to 100° C. This reaction may be performed using a microwave reactor. In this case, the reaction time is generally 5 min to 24 hr, preferably 30 min to 2 hr. The reaction temperature is generally from room temperature to 250° C., preferably 50° C. to 200° C.

The obtained compound (Ib) can be used directly as a reaction mixture, or as a crude product, for the next reaction. It can also be isolated from the reaction mixture according to a conventional method, and can be easily purified by a separation means such as washing, recrystallization, distillation, chromatography and the like.

When both $E^2$ and $E^3$ are hydroxy groups, compound (Ib) can be produced by "Mitsunobu reaction" [for example, Synthesis, 1-27, (1981)].

The "Mitsunobu reaction" can be performed using, for example, about 0.5 to 10 mol, preferably about 1 to 2 mol, of compound (4), about 1 to 20 mol, preferably about 1 to 5 mol, of azodicarboxamide or azodicarboxylate, and about 1 to 20 mol, preferably about 1 to 5 mol, of trialkylphosphine or triarylphosphine, per 1 mol of compound (5).

This reaction is preferably performed using a solvent inert to the reaction. While such solvent is not particularly limited as long as the reaction proceeds and, for example, aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; and the like can be mentioned. Two or more kinds of these solvents may be mixed and used at an appropriate ratio.

As "azodicarboxamide or azodicarboxylate", diisopropyl azodicarboxylate, diethyl azodicarboxylate, bis(2-methoxyethyl)azodicarboxylate, 1,1'-(azodicarbonyl)dipiperidine and the like are used.

As "trialkylphosphine or triarylphosphine", triphenylphosphine, tributylphosphine, trimethylphosphine and the like are used.

The reaction time is generally 30 min to 1 week, preferably 2 hr to 24 hr. The reaction temperature is generally –20° C. to 100° C., preferably 0° C. to 8° C.

The obtained compound (Ib) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (5) can be produced by the following production method or a method analogous thereto.

Compound (4) may be a commercially available reagent, or can be produced according to a method known per se.

<Step B>

When $L^{2'}$ is S, compound (Ib') is obtained by reacting about 1.0 to 30.0 mol, preferably about 1.0 to 5.0 mol, of an oxidizing agent per 1 mol of compound (Ib) in Step B.

Examples of the oxidizing agent include peracids such as hydrogen peroxide, Oxone (registered trade mark), peracetic acid, perbenzoic acid, m-chloroperbenzoic acid and the like, oxoacids such as hypochlorous acid, periodic acid and the like and a salt thereof, metal oxoacids such as chromic acid and the like and a salt thereof and other oxidizing agents.

This reaction is preferably performed using a solvent inert to the reaction. While such solvent is not particularly limited as long as the reaction proceeds, for example, alcohols such as methanol, ethanol, propanol, 1,1-dimethylethanol and the like; aromatic hydrocarbons such as benzene, toluene and the like; amides such as N,N-dimethylformamide, N,N-dimethylacetamide and the like; nitriles such as acetonitrile, propionitrile and the like; sulfoxides such as dimethyl sulfoxide and the like; organic acids such as acetic acid, trifluoroacetic acid and the like; water, a mixed solvent thereof and the like can be mentioned.

The reaction time is generally 1 hr to 60 hr, preferably 1 hr to 24 hr. The reaction temperature is generally −50° C. to 150° C., preferably 0° C. to 100° C.

The obtained compound (Ib') can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (Ic) and compound (Ic') which are compounds (I), wherein $L^1$ is O, $S(O)_{m1}$ or $NR^{3,4}$, and $L^2$ is $CR^{4B}R^{4C}$ can also be produced by, as another method, for example, the reaction of compound (6) and compound (7) shown in the following production method 1-3 and, where necessary, a subsequent oxidation reaction.

[Production Method 1-3]

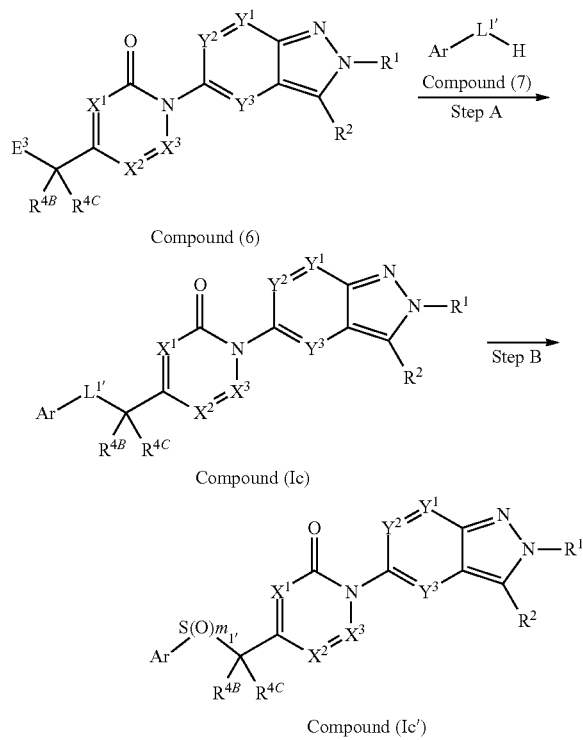

wherein $L^{1'}$ is O, S or $NR^{3,4}$, m1' is an integer of 1 or 2, and other symbols are each as defined above, when $E^3$ is a hydroxy group, $L^{1'}$ is O, and Step B can be present only when $L^{1'}$ is S.

<Step A>

When $E^3$ is a hydroxy group and $L^{1'}$ is O, compound (Ic) can be produced from compound (6) according to the "Mitsunobu reaction" shown in the above-mentioned production method 1-2, Step A, or a method analogous thereto.

When $E^3$ is a leaving group, compound (Ic) can be produced using about 1.0 to 10.0 mol, preferably about 1.0 to 3.0 mol, of compound (7) and about 1.0 to 10.0 mol, preferably about 1.0 to 5.0 mol, of a base, per 1 mol of compound (6).

Examples of the base include inorganic salts such as sodium hydride, potassium carbonate, sodium carbonate, cesium carbonate and the like; metal alkoxides such as sodium methoxide, sodium ethoxide, potassium tert-butoxide and the like; amines such as pyridine, triethylamine, N,N-dimethylaniline, 1,8-diazabicyclo[5.4.0]undec-7-ene and the like, and the like. Two or more kinds of these bases may be mixed at an appropriate ratio and used.

This reaction is preferably performed using a solvent inert to the reaction. While such solvent is not particularly limited as long as the reaction proceeds, for example, aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide, N,N-dimethylacetamide and the like; sulfoxides such as dimethyl sulfoxide and the like, and the like can be mentioned. Two or more kinds of these solvents may be mixed at an appropriate ratio and used.

The reaction time is generally 15 min to 60 hr, preferably 15 min to 24 hr. The reaction temperature is generally −20° C. to 150° C., preferably 0° C. to 100° C.

The obtained compound (Ic) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (6) can be produced by the method described in the following production method or a method analogous thereto.

Compound (7) may be a commercially available reagent, or can be produced by a method known per se.

<Step B>

When $L^{1'}$ is S, compound (Ic') is obtained by reacting about 1.0 to 30.0 mol, preferably about 1.0 to 5.0 mol, of an oxidizing agent per 1 mol of compound (Ic) in Step B.

As the oxidizing agent, peracids such as hydrogen peroxide, Oxone (registered trade mark), peracetic acid, perbenzoic acid, m-chloroperbenzoic acid and the like, oxoacids such as hypochlorous acid, periodic acid and the like and a salt thereof, metal oxoacids such as chromic acid and the like and a salt thereof and other oxidizing agents can be mentioned.

This reaction is preferably performed using a solvent inert to the reaction. While such solvent is not particularly limited as long as the reaction proceeds, for example, alcohols such as methanol, ethanol, propanol, 1,1-dimethylethanol and the like; aromatic hydrocarbons such as benzene, toluene and the like; amides such as N,N-dimethylformamide, N,N-dimethylacetamide and the like; nitriles such as acetonitrile, propionitrile and the like; sulfoxides such as dimethyl sulfoxide and the like; organic acids such as acetic acid, trifluoroacetic acid and the like; water, a mixed solvent thereof and the like can be mentioned.

The reaction time is generally 1 hr to 60 hr, preferably 1 hr to 24 hr. The reaction temperature is generally −50° C. to 150° C., preferably 0° C. to 100° C.

The obtained compound (Ic') can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (6) which is the starting compound of the production method 1-3 can be produced by obtaining compound (9) by the reaction of compound (8) and compound (3) according to the following production method 2-1, and thereafter according to a method known per se.

[Production Method 2-1]

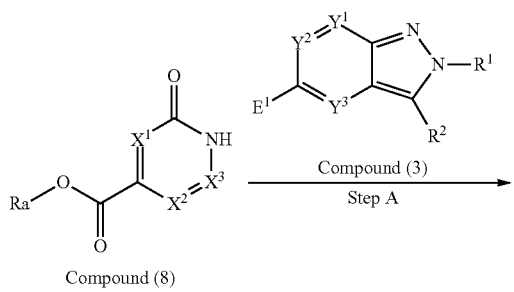

Compound (8)

↓ Compound (3), Step A

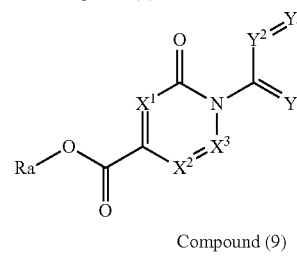

Compound (9)

↓ Step B

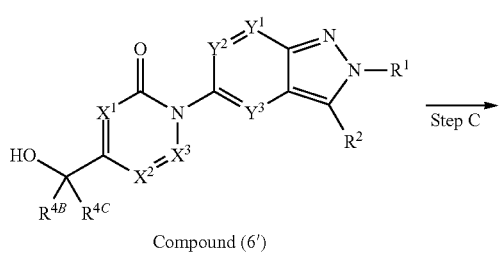

Compound (6')

↓ Step C

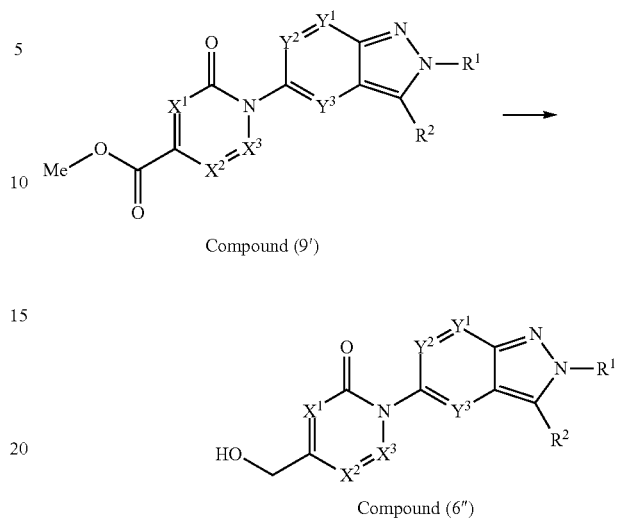

Compound (6)

wherein Ra is a $C_{1-6}$alkyl group, and other symbols are as defined above.

<Step A>

In Step A, compound (8) and compound (3) are reacted by the method of the above-mentioned production method 1-1, Step A, or a method analogous thereto to give compound (9).

Compound (8) may be a commercially available reagent or can be produced according to a method known per se.

<Step B>

In Step B, compound (6') which is compound (6) wherein $E^3$ is a hydroxy group is produced from compound (9) according to a method known per se.

<Step C>

In Step C, compound (6) is produced from compound (6') according to a method known per se.

As production method 2-1, Step B, the following reaction is shown.

[Production Method 2-1A]

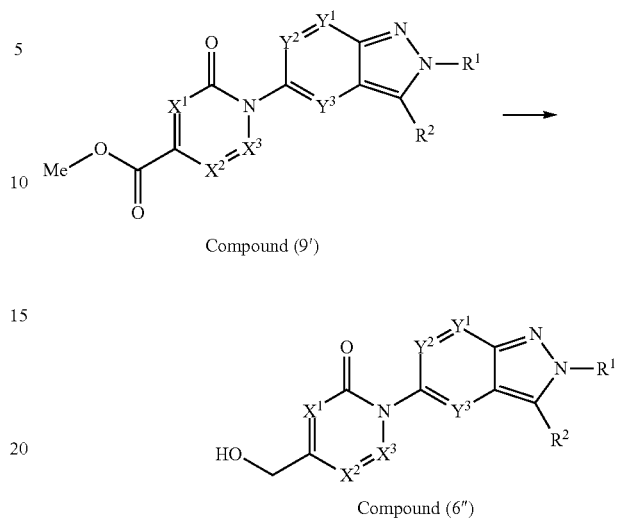

Compound (9')

↓

Compound (6'')

wherein Me is methyl, and other symbols are each as defined above.

That is, in production method 2-1A, compound (6") is obtained by reacting about 0.5 to 10.0 mol, preferably 1.0 to 5.0 mol, of a reducing agent per 1 mol of compound (9').

Examples of the reducing agent include diisopropylaluminum hydride, lithium aluminum hydride, lithium borohydride, sodium borohydride and the like.

This reaction is preferably performed using a solvent inert to the reaction. While such solvent is not particularly limited as long as the reaction proceeds, for example, aromatic hydrocarbons such as benzene, toluene, xylene and the like; ethers such as tetrahydrofuran, 1,4-dioxane, diethyl ether and the like; halogenated hydrocarbons such as chloroform, dichloromethane and the like, and the like can be mentioned. Two or more kinds of these solvents may be mixed and used at an appropriate ratio.

The reaction time is generally 30 min to 48 hr, preferably 3 hr to 24 hr. The reaction temperature is generally −80° C. to 100° C., preferably −80° C. to 80° C.

The obtained compound (6") can be used directly as a reaction mixture, or as a crude product, for the next reaction. It can also be isolated from the reaction mixture according to a conventional method, and can be easily purified by a separation means such as washing, recrystallization, distillation, chromatography and the like.

As production method 2-1, Step C, the following reaction is shown.

[Production Method 2-1B]

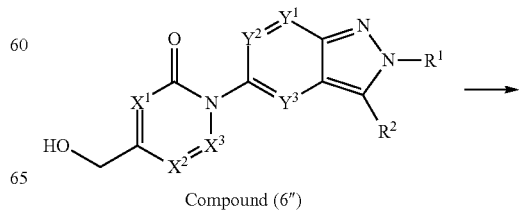

Compound (6'')

-continued

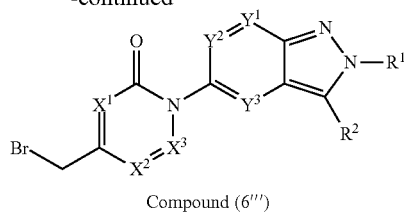

Compound (6''')

wherein each symbol is as defined above.

That is, in production method 2-1B, compound (6") is brominated according to a method known per se to give compound (6''').

Compound (2') and compound (2"), which are compounds (2), which are the starting compounds in production method 1-1, wherein $L^1$ is $CR^{3B}R^{3C}$ and $L^2$ is O, $S(O)_{m2}$ or $NR^{4A}$, can be synthesized according to the following production method 2-2.

[Production Method 2-2]

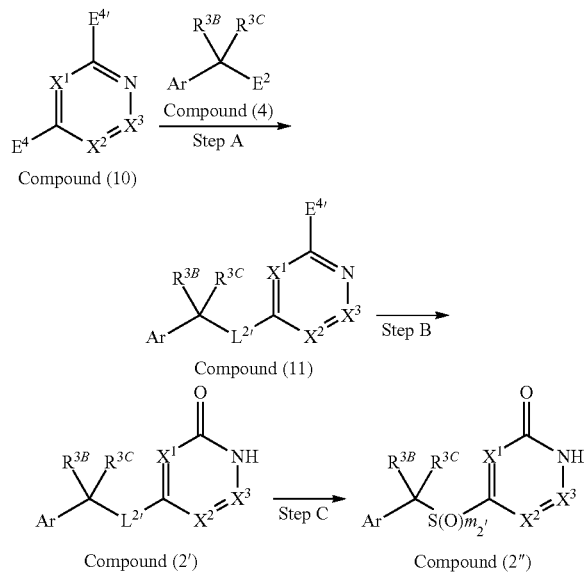

wherein $E^4$ and $E^{4'}$ are each a halogen atom (e.g., a chlorine atom, a bromine atom, an iodine atom and the like) or a hydroxy group, and other symbols are each as defined above. One of $E^4$ and $E^2$ is a leaving group or they are simultaneously hydroxy groups, and Step C can be present only when $L^{2'}$ is S.

<Step A>

When $E^4$ is a hydroxy group and $E^2$ is a leaving group, or $E^4$ is a halogen atom and $E^2$ is SH, $NR^{4A}H$ or a hydroxy group, compound (11) is produced using about 1.0 to 10.0 mol, preferably about 1.0 to 3.0 mol, of compound (4) and about 1.0 to 10.0 mol, preferably about 1.0 to 5.0 mol, of a base, per 1 mol of compound (10) in Step A.

Examples of the base include inorganic salts such as sodium hydride, potassium carbonate, sodium carbonate, cesium carbonate and the like; metal alkoxides such as sodium methoxide, sodium ethoxide, potassium tert-butoxide and the like; amines such as pyridine, triethylamine, N,N-dimethylaniline, 1,8-diazabicyclo[5.4.0]undec-7-ene and the like, and the like. Two or more kinds of these bases may be mixed at an appropriate ratio and used.

This reaction is preferably performed using a solvent inert to the reaction. While such solvent is not particularly limited as long as the reaction proceeds, for example, aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like, and the like can be mentioned. Two or more kinds of these solvents may be mixed and used at an appropriate ratio.

The reaction time is generally 15 min to 60 hr, preferably 15 min to 24 hr. The reaction temperature is generally −20° C. to 150° C., preferably 0° C. to 100° C.

The obtained compound (11) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (10) and compound (4) may be each a commercially available reagent, or can be produced according to a method known per se.

When both $E^4$ and $E^2$ are hydroxy groups, compound (11) can be produced from compound (10) according to the "Mitsunobu reaction" shown in the above-mentioned production method 1-2, Step A, or a method analogous thereto.

<Step B>

When $E^{4'}$ in compound (11) is a hydroxy group, compound (11) is compound (2').

When $E^{4'}$ is a halogen atom, compound (2') is produced by hydrolysis in the presence of about 1 to 20 mol, preferably about 1 to 5 mol, of a base per 1 mol of compound (11) in Step B.

Examples of the base include inorganic salts such as potassium hydroxide, sodium hydroxide, sodium carbonate, potassium carbonate and the like. Two or more kinds of these bases may be mixed at an appropriate ratio and used.

This reaction is preferably performed in water and, where necessary, ethers such as tetrahydrofuran, 1,4-dioxane, diethyl ether and the like; or ketones such as acetone, 2-butanone and the like may be mixed at an appropriately ratio and used.

The reaction time is generally 15 min to 60 hr, preferably 15 min to 24 hr. The reaction temperature is generally 0° C. to 200° C., preferably from room temperature to 150° C.

The obtained compound (2') can be used directly as a reaction mixture, or as a crude product, for the next reaction. It can also be isolated from the reaction mixture according to a conventional method, and can be easily purified by a separation means such as washing, recrystallization, distillation, chromatography and the like.

<Step C>

In Step C, compound (2") is produced by reacting compound (2') by the method of production method 1-3, Step B, or a method analogous thereto.

Compound (5), which is the starting compound of production method 1-2, can be produced by deprotection of compound (Id) shown in the following production method 2-3, which is compound (I) wherein ring Ar is benzene, $L^1$ is $CH_2$, and $L^2$ is O, and a subsequent halogenation or sulfonyloxylation.

[Production Method 2-3]

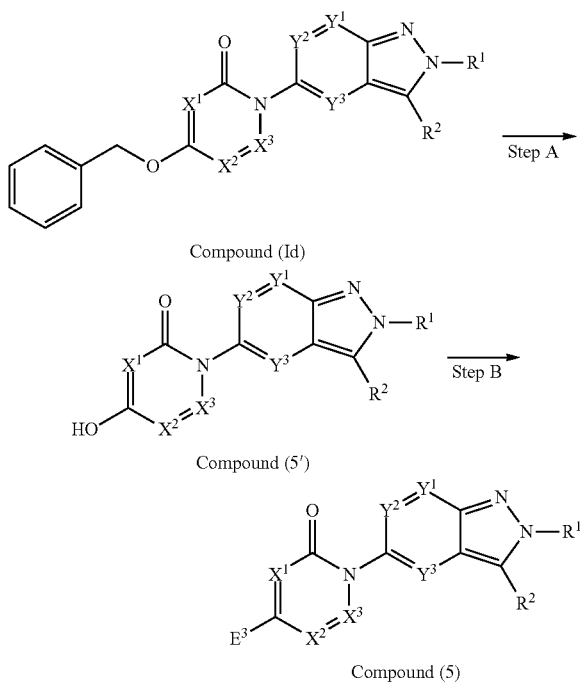

Compound (Id)

Compound (5')

Compound (5)

wherein each symbol is as defined above.
<Step A>
In Step A, compound (5') is obtained by reduction using about 0.01 to 5.0 mol, preferably about 0.01 to 2.0 mol, of a metal catalyst per 1 mol of compound (Id) under a hydrogen atmosphere.

As the metal catalyst, palladium-carbon, palladium hydroxide-carbon, platinum oxide, platinum and the like can be mentioned.

This reaction is preferably performed using a solvent inert to the reaction. While such solvent is not particularly limited as long as the reaction proceeds, for example, solvents such as alcohols such as methanol, ethanol, propanol and the like; aromatic hydrocarbons such as benzene, toluene and the like; saturated hydrocarbons such as cyclohexane, hexane and the like; ethers such as tetrahydrofuran, 1,4-dioxane, 1,2-dimethoxyethane and the like; amides such as N,N-dimethylformamide, N,N-dimethylacetamide and the like; sulfoxides such as dimethylsulfoxide and the like; water and the like or a mixed solvent thereof and the like are preferable.

The reaction time is generally 1 hr to 60 hr, preferably 1 hr to 48 hr. The reaction temperature is generally −50° C. to 150° C., preferably 0° C. to 100° C., and the pressure is about 1 to 10 atm, preferably about 1 to 5 atm.

The obtained compound (5') can be used directly as a reaction mixture, or as a crude product, for the next reaction. It can also be isolated from the reaction mixture according to a conventional method, and can be easily purified by a separation means such as washing, recrystallization, distillation, chromatography and the like.

As another method, Step A can also be performed in the presence of an acid. That is, compound (5') is obtained using about 0.01 to 100 mol, preferably about 0.1 to 50 mol, of an acid per 1 mol of compound (Id).

Examples of the acid include organic acids such as acetic acid, trifluoroacetic acid, p-toluenesulfonic acid and the like; mineral acids such as hydrochloric acid, sulfuric acid and the like; Lewis acids such as boron trichloride, boron tribromide and the like. These acids may also be used as solvents.

This reaction is preferably performed using a solvent inert to the reaction. The solvent is not particularly limited as long as the reaction proceeds. Examples thereof include aromatic hydrocarbons such as benzene, toluene, xylene and the like; halogenated hydrocarbons such as chloroform, dichloromethane and the like; amides such as N,N-dimethylformamide and the like; sulfoxides such as dimethyl sulfoxide and the like; and the like. Two or more kinds of these solvents may be mixed and used at an appropriate ratio.

The reaction time is generally 15 min to 60 hr, preferably 15 min to 24 hr. The reaction temperature is generally 0° C. to 200° C., preferably from room temperature to 100° C.

The obtained compound (5') can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (Id) can be produced by the method described in the above-mentioned production method 1-1, or a method analogous thereto.
<Step B>
When $E^3$ is a hydroxy group, compound (5') is compound (5).

When $E^3$ is a halogen atom, compound (5) can be produced using about 1.0 to 20.0 mol, preferably about 1.0 to 5.0 mol, of a halogenating agent, per 1 mol of compound (5').

As the halogenating agent, for example, phosphorus oxybromide, phosphorus tribromide, phosphorus oxychloride, thionyl chloride, sulfuryl chloride and the like can be mentioned.

This reaction is preferably performed using a solvent inert to the reaction. While such solvent is not particularly limited as long as the reaction proceeds, for example, aromatic hydrocarbons such as benzene, toluene, xylene and the like; ethers such as tetrahydrofuran, 1,4-dioxane, diethyl ether and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like, and the like can be mentioned. Two or more kinds of these solvents may be mixed and used at an appropriate ratio.

The reaction time is generally 15 min to 60 hr, preferably 15 min to 24 hr. The reaction temperature is generally −20° C. to 150° C., preferably 0° C. to 100° C.

The obtained compound (5) can be used directly as a reaction mixture, or as a crude product, for the next reaction. It can also be isolated from the reaction mixture according to a conventional method, and can be easily purified by a separation means such as washing, recrystallization, distillation, chromatography and the like.

When $E^3$ is a substituted sulfonyloxy group, compound (5) can be produced using about 1.0 to 20.0 mol, preferably about 1.0 to 5.0 mol, of substituted sulfonyl chloride and 1.0 to 20.0 mol, preferably about 1.0 to 5.0 mol, of a base, per 1 mol of compound (5').

As the substituted sulfonyl chloride, for example, methanesulfonyl chloride, p-toluenesulfonyl chloride and the like can be mentioned.

Examples of the base include inorganic salts such as sodium hydride, potassium carbonate, sodium carbonate, cesium carbonate and the like; metal alkoxides such as sodium methoxide, sodium ethoxide, potassium tert-butoxide and the like; amines such as pyridine, triethylamine, N,N-dimethylaniline, 1,8-diazabicyclo[5.4.0]undec-7-ene and the like, and the like. Two or more kinds of these bases may be mixed and used at an appropriate ratio.

This reaction is preferably performed using a solvent inert to the reaction. The solvent is not particularly limited as long as the reaction proceeds. Examples thereof include aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide, N,N-dimethylacetamide and the like; sulfoxides such as dimethyl sulfoxide and the like; water and the like. Two or more kinds of these solvents may be mixed and used at an appropriate ratio.

The reaction time is generally 15 min to 60 hr, preferably 15 min to 3 hr. The reaction temperature is generally −20° C. to 200° C., preferably 0° C. to 100° C.

The obtained compound (5) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (3), which is the starting compound of production methods 1-1 and 2-1, can be produced by an oxidation reaction of compound (12), followed by indazole ring construction reaction, and alkylation reaction of the obtained compound (14). Alternatively, it can also be produced by nitration of compound (17) to give compound (18), which is converted to imine intermediate (20) and cyclized.

[Production Method 3-1]

This reaction is preferably performed using a solvent inert to the reaction. While such solvent is not particularly limited as long as the reaction proceeds, for example, aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide and the like; sulfoxides such as dimethyl sulfoxide and the like; organic acids such as acetic acid, trifluoroacetic acid and the like, and the like can be mentioned. Two or more kinds of these solvents may be mixed and used at an appropriate ratio.

The reaction time is generally 15 min to 60 hr, preferably 30 min to 24 hr. The reaction temperature is generally 0° C. to 250° C., preferably from room temperature to 100° C.

The obtained compound (13) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (12) may be a commercially available reagent, or can be produced according to a method known per se.

<Step B>

In Step B, compound (14) is obtained by using about 1.0 to 10.0 mol of hydrazine hydrate per 1 mol of compound (13).

This reaction is preferably performed using a solvent inert to the reaction. While such solvent is not particularly limited as long as the reaction proceeds, for example, aromatic hydrocarbons such as benzene, toluene, xylene and the like; ethers

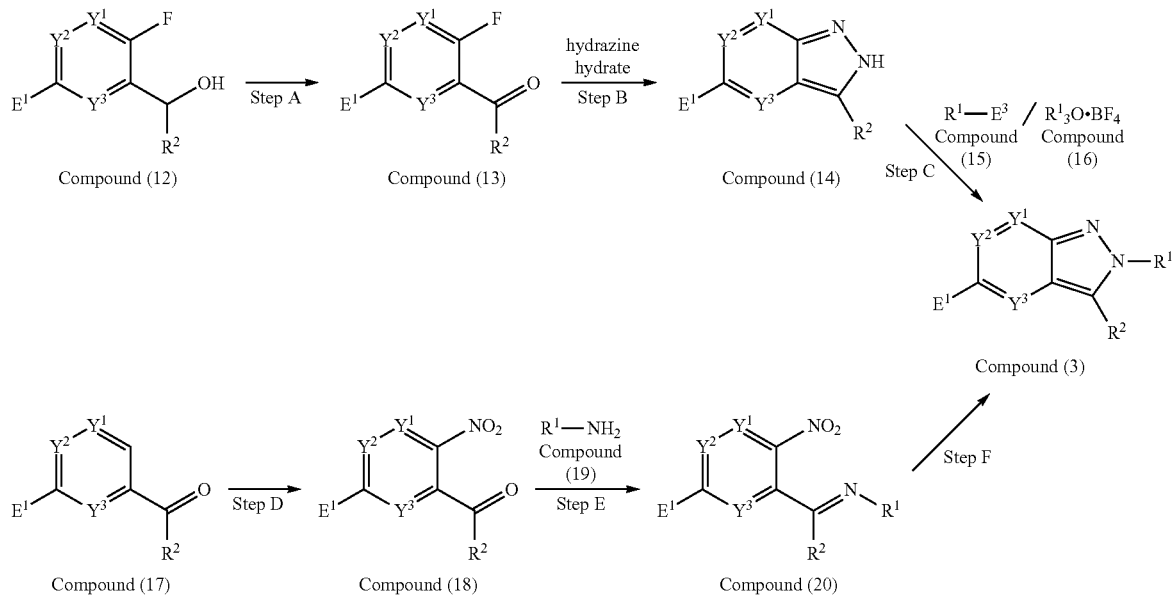

wherein each symbol is as defined above.

<Step A>

In Step A, compound (13) is obtained using about 1.0 to 20.0 mol, preferably about 1.0 to 10.0 mol, of an oxidizing agent per 1 mol of compound (12).

As the oxidizing agent, for example, manganese dioxide, 1,1,1-triacetoxy-1,1-dihydro-1,2-benziodoxol-3-(1H)-one (Dess-Martin reagent), 2-iodoxybenzoic acid, sulfur trioxide, pyridinium chlorochromate and the like can be mentioned.

such as tetrahydrofuran, 1,4-dioxane, diethyl ether and the like; alcohols such as methanol, ethanol, butanol and the like; halogenated hydrocarbons such as chloroform, dichloromethane and the like; amides such as N,N-dimethylformamide and the like; sulfoxides such as dimethyl sulfoxide and the like; organic acids such as acetic acid, trifluoroacetic acid and the like, and the like can be mentioned. Two or more kinds of these solvents may be mixed and used at an appropriate ratio.

The reaction time is generally 15 min to 60 hr, preferably 30 min to 26 hr. The reaction temperature is generally 0° C. to 250° C., preferably from room temperature to 200° C.

The obtained compound (14) can be used directly as a reaction mixture, or as a crude product, for the next reaction. It can also be isolated from the reaction mixture according to a conventional method, and can be easily purified by a separation means such as washing, recrystallization, distillation, chromatography and the like.

<Step C>

In Step C, compound (3) is obtained using about 1 to 10 mol, preferably about 1 to 5 mol of compound (15) and about 1 to 20 mol, preferably about 1 to 10 mol, of a base per 1 mol of compound (14).

Examples of the base include inorganic salts such as sodium hydride, potassium carbonate, sodium carbonate, cesium carbonate and the like; metal alkoxides such as sodium methoxide, sodium ethoxide, potassium tert-butoxide and the like; amines such as pyridine, triethylamine, N,N-dimethylaniline, 1,8-diazabicyclo[5.4.0]undec-7-ene and the like, and the like. Two or more kinds of these bases may be mixed and used at an appropriate ratio.

This reaction is preferably performed using a solvent inert to the reaction. While such solvent is not particularly limited as long as the reaction proceeds, for example, aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide, N,N-dimethylacetamide and the like; sulfoxides such as dimethyl sulfoxide and the like, and the like can be mentioned. Two or more kinds of these solvents may be mixed and used at an appropriate ratio.

The reaction time is generally 15 min to 60 hr, preferably 15 min to 24 hr. The reaction temperature is generally −20° C. to 150° C., preferably 0° C. to 100° C.

The obtained compound (3) can be used directly as a reaction mixture, or as a crude product, for the next reaction. It can also be isolated from the reaction mixture according to a conventional method, and can be easily purified by a separation means such as washing, recrystallization, distillation, chromatography and the like.

As another method, compound (3) can also be obtained by reacting about 1.0 to 10.0 mol, preferably about 1.0 to 5.0 mol, of compound (16) per 1 mol of compound (14).

This reaction is preferably performed using a solvent inert to the reaction. While such solvent is not particularly limited as long as the reaction proceeds, for example, aromatic hydrocarbons such as benzene, toluene, xylene and the like; ethers such as tetrahydrofuran, 1,4-dioxane, diethyl ether and the like; esters such as ethyl acetate, methyl acetate and the like; halogenated hydrocarbons such as chloroform, dichloromethane and the like; nitriles such as acetonitrile, propionitrile and the like; amides such as N,N-dimethylformamide, N,N-dimethylacetamide and the like; sulfoxides such as dimethyl sulfoxide and the like, and the like can be mentioned. Two or more kinds of these solvents may be mixed and used at an appropriate ratio.

The reaction time is generally 15 min to 60 hr, preferably 15 min to 24 hr. The reaction temperature is generally −20° C. to 150° C., preferably 0° C. to 50° C.

The obtained compound (3) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (15) may be a commercially available reagent, or can be produced according to a method known per se.

Compound (16) may be a commercially available reagent, or can be produced according to a method known per se.

<Step D>

In Step D, compound (18) is obtained by reacting about 1.0 to 10.0 mol, preferably about 1.0 to 5.0 mol, of a nitrating reagent per 1 mol of compound (17).

As the nitrating reagent, for example, mineral acids such as mixed acid, nitric acid and the like; nitrate salts such as potassium nitrate, sodium nitrate, tetramethylammonium nitrate, silver nitrate and the like, and the like can be mentioned.

This reaction is preferably performed using a solvent inert to the reaction. While such solvent is not particularly limited as long as the reaction proceeds, for example, aromatic hydrocarbons such as benzene, nitrobenzene, chlorobenzene and the like; ethers such as tetrahydrofuran, 1,4-dioxane, diethyl ether and the like; alcohols such as methanol, ethanol, isopropyl alcohol and the like; halogenated hydrocarbons such as chloroform, dichloromethane and the like; nitriles such as acetonitrile, propionitrile and the like; amides such as N,N-dimethylformamide and the like; organic acids such as acetic acid, trifluoroacetic acid and the like; mineral acids such as sulfuric acid and the like; water and the like can be mentioned. Two or more kinds of these solvents may be mixed and used at an appropriate ratio.

The reaction time is generally 15 min to 60 hr, preferably 30 min to 24 hr. The reaction temperature is −78° C. to 150° C., preferably −20° C. to 100° C.

The obtained compound (18) can be used directly as a reaction mixture, or as a crude product, for the next reaction. It can also be isolated from the reaction mixture according to a conventional method, and can be easily purified by a separation means such as washing, recrystallization, distillation, chromatography and the like.

Compound (17) may be a commercially available reagent or can be produced according to a method known per se.

<Step E>

In Step E, compound (20) is obtained by reacting about 1.0 to 10.0 mol, preferably 1.0 to 5.0 mol, of compound (19) per 1 mol of compound (18). This reaction can be accelerated by using an acid.

As the acid, for example, organic acids such as acetic acid, trifluoroacetic acid, p-toluenesulfonic acid and the like; mineral acids such as hydrochloric acid, sulfuric acid and the like; Lewis acids such as titanium(IV) tetraisopropoxide and the like can be mentioned. The amount of the acid to be used is generally about 1.0 to 10.0 mol, preferably about 1.0 to 5.0 mol, per 1 mol of compound (18).

This reaction is preferably performed using a solvent inert to the reaction. While such solvent is not particularly limited as long as the reaction proceeds, for example, aromatic hydrocarbons such as benzene, toluene, xylene and the like; ethers such as tetrahydrofuran, 1,4-dioxane, diethyl ether and the like; halogenated hydrocarbons such as chloroform, dichloromethane and the like; nitriles such as acetonitrile, propionitrile and the like; amides such as N,N-dimethylformamide, N,N-dimethylacetamide and the like; sulfoxides such as dimethyl sulfoxide and the like, acetic acid and the like can be mentioned. Two or more kinds of these solvents may be mixed and used at an appropriate ratio.

The reaction time is generally 15 min to 60 hr, to preferably 15 min to 24 hr. The reaction temperature is generally 0° C. to 200° C., preferably from room temperature to 150° C.

The obtained compound (20) can also be used as a reaction mixture or a crude product for the next reaction.

Compound (19) may be a commercially available reagent, or can be produced according to a method known per se.
<Step F>

In Step F, compound (3) is obtained by reacting about 1.0 to 10.0 mol, preferably 1.0 to 5.0 mol, of phosphorous acid ester, per 1 mol of compound (20). Such phosphorous acid ester may also be used as a solvent.

As the phosphorous acid ester, for example, trimethyl phosphite, triethyl phosphite, triisopropyl phosphite and the like can be mentioned.

This reaction is preferably performed using a solvent inert to the reaction. While such solvent is not particularly limited as long as the reaction proceeds, for example, aromatic hydrocarbons such as benzene, toluene, xylene and the like; ethers such as tetrahydrofuran, 1,4-dioxane, diethyl ether and the like; ketones such as acetone, 2-butanone and the like; halogenated hydrocarbons such as chloroform, dichloromethane and the like; nitriles such as acetonitrile, propionitrile and the like; amides such as N,N-dimethylformamide, N,N-dimethylacetamide and the like; sulfoxides such as dimethyl sulfoxide and the like, and the like can be mentioned. Two or more kinds of these solvents may be mixed and used at an appropriate ratio.

The reaction time is generally 15 min to 60 hr, preferably 15 min to 24 hr. The reaction temperature is generally 0° C. to 200° C., preferably from room temperature to 150° C.

The obtained compound (3) can be used directly as a reaction mixture, or as a crude product, for the next reaction. It can also be isolated from the reaction mixture according to a conventional method, and can be easily purified by a separation means such as washing, recrystallization, distillation, chromatography and the like.

In each reaction of the aforementioned schemes, when a starting compound has hydroxy, amino (including —NH—, —NH$_2$), carboxy, carbonyl or mercapto as a substituent, a protecting group generally used in the peptide chemistry and the like may be introduced into these groups. By removing the protecting group as necessary after the reaction, the objective compound can be obtained.

Examples of the hydroxyl-protecting group include $C_{1-6}$ alkyl (e.g., methyl, ethyl, propyl, isopropyl, butyl, tert-butyl), phenyl, trityl, $C_{1-10}$ aralkyl (e.g., benzyl), formyl, $C_{1-6}$ alkyl-carbonyl (e.g., acetyl, propionyl), benzoyl, $C_{7-10}$ aralkyl-carbonyl (e.g., benzylcarbonyl), 2-tetrahydropyranyl, 2-tetrahydrofuranyl, silyl (e.g., trimethylsilyl, triethylsilyl, dimethylphenylsilyl, tert-butyldimethylsilyl, tert-butyldiethylsilyl), $C_{2-6}$alkenyl (e.g., 1-allyl) and the like. These groups are optionally substituted by 1 to 3 substituents selected from a halogen atom (e.g., a fluorine atom, a chlorine atom, a bromine atom, an iodine atom), $C_{1-6}$ alkyl (e.g., methyl, ethyl, propyl), $C_{1-6}$alkoxy (e.g., methoxy, ethoxy, propoxy), nitro and the like.

Examples of the amino-protecting group include formyl, $C_{1-6}$alkyl-carbonyl (e.g., acetyl, propionyl), $C_{1-6}$alkoxy-carbonyl (e.g., methoxycarbonyl, ethoxycarbonyl, tert-butoxycarbonyl), benzoyl, $C_{7-10}$ aralkyl-carbonyl (e.g., benzylcarbonyl), $C_{7-14}$ aralkyloxy-carbonyl (e.g., benzyloxycarbonyl, 9-fluorenylmethoxycarbonyl), $C_{7-10}$ aralkyl (e.g., benzyl, 4-methoxybenzyl), trityl, phthaloyl, N,N-dimethylaminomethylene, silyl (e.g., trimethylsilyl, triethylsilyl, dimethylphenylsilyl, tert-butyldimethylsilyl, tert-butyldiethylsilyl), $C_{2-6}$alkenyl (e.g., 1-allyl) and the like. These groups are optionally substituted by 1 to 3 substituents selected from a halogen atom (e.g., a fluorine atom, a chlorine atom, a bromine atom, an iodine atom), $C_{1-6}$ alkoxy (e.g., methoxy, ethoxy, propoxy), nitro and the like.

Examples of the carboxy-protecting group include $C_{1-6}$ alkyl (e.g., methyl, ethyl, propyl, isopropyl, butyl, tert-butyl), $C_{7-11}$ aralkyl (e.g., benzyl), phenyl, trityl, silyl (e.g., trimethylsilyl, triethylsilyl, dimethylphenylsilyl, tert-butyldimethylsilyl, tert-butyldiethylsilyl, tert-butyldiphenylsilyl), $C_{2-6}$alkenyl (e.g., 1-allyl) and the like. These groups are optionally substituted by 1 to 3 substituents selected from a halogen atom (e.g., a fluorine atom, a chlorine atom, a bromine atom, an iodine atom), $C_{1-6}$alkoxy (e.g., methoxy, ethoxy, propoxy), nitro and the like.

Examples of the carbonyl-protecting group include cyclic acetal (e.g., 1,3-dioxane), acyclic acetal (e.g., di-$C_{1-6}$alkyl acetal) and the like.

Examples of the mercapto-protecting group include a $C_{1-6}$ alkyl group, a phenyl group, a trityl group, a $C_{7-10}$ aralkyl group (e.g., benzyl), a $C_{1-6}$alkyl-carbonyl group, a benzoyl group, a $C_{7-10}$ aralkyl-carbonyl group (e.g., benzylcarbonyl), a $C_{1-6}$alkoxy-carbonyl group, a $C_{6-14}$ aryloxy-carbonyl group (e.g., phenyloxycarbonyl), a $C_{7-14}$ aralkyloxy-carbonyl group (e.g., benzyloxycarbonyl, 9-fluorenylmethoxycarbonyl), a 2-tetrahydropyranyl group, a $C_{1-6}$alkylamino-carbonyl group (e.g., methylaminocarbonyl, ethylaminocarbonyl) and the like. These groups are optionally substituted by 1 to 3 substituents selected from a halogen atom, a $C_{1-6}$alkyl group, a $C_{1-6}$alkoxy group and a nitro group.

The above-mentioned protecting groups can be removed by a method known per se, for example, the method described in Protective Groups in Organic Synthesis, John Wiley & Sons, Inc. (1980) and the like. For example, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide etc.) and the like, a reduction method and the like are used.

Inasmuch as compound (I) and a prodrug thereof (hereinafter abbreviated as the compound of the present invention) has an excellent MCH receptor (particularly, MCH receptor 1) antagonistic action, it is useful as an agent for the prophylaxis or treatment of diseases caused by MCH.

In addition, the compound of the present invention also shows low toxicity (e.g., cardiac toxicity (e.g., hERG inhibitory activity), PLsis inducing potential, acute toxicity, chronic toxicity, genetic toxicity, reproductive toxicity, drug interaction, carcinogenicity, phototoxicity).

Moreover, the compound of the present invention is excellent in oral absorbability.

Furthermore, the compound of the present invention is excellent in brain transfer function.

The compound of the present invention is excellent in metabolic stability.

Accordingly, the compound of the present invention is safely administered as an agent for the prophylaxis or treatment of diseases caused by MCH, and the like to mammals (e.g., rat, mouse, guinea pig, rabbit, sheep, horse, pig, cow, monkey, human).

The diseases caused by MCH include, for example, obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity and the like], hyperphagia, emotional disorder, sexual dysfunction, depression, anxiety and the like.

The compound of the present invention is also useful as a drug for the prophylaxis or treatment of a lifestyle-related diseases such as diabetes (e.g., type 1 diabetes, type 2 diabetes, gestational diabetes, obese diabetes, borderline diabetes), impaired glucose tolerance (IGT), diabetic complications (e.g., diabetic retinopathy, diabetic neuropathy, diabetic nephropathy), hyperlipidemia (e.g., hypertriglyceridemia, hypercholesterolemia, high LDL-cholesterolemia, low HDL-cholesterolemia, postprandial hyperlipemia), arteriosclerosis, arthritis in knee, metabolic syndrome and the like.

Moreover, the compound of the present invention is also useful as an anorexigenic agent.

The compound of the present invention can also be concurrently used with diet therapy (e.g., diet therapy for diabetes), or an exercise therapy.

The compound of the present invention can be used for the prophylaxis or treatment of pigmentation disorder based on abnormality of melanin or melanocyte. Here, as the pigmentation disorder, pigment proliferation, pigment decrease and the like can be mentioned. As the pigment proliferation, drug pigmentation caused by antitumor agent and the like; chromatosis and incompetence of pigment associated with diseases such as endocrine metabolism disorder (e.g., Addison's disease), genetic diseases, chronic hepatopathy, kidney failure, acanthosis nigricans, systemic scleroderma and the like; and the like can be mentioned. As the pigment decrease, phenylketonuria, systemic or localized albinism, foliaceous leukoderma or leukoderma vulgaris associated with tuberous sclerosis; depigmentation associated with systemic scleroderma and the like can be mentioned.

The compound of the present invention can be used for the prophylaxis or treatment of dyspigmentation due to chloasma, ephelides, sunburn and the like; and further, hyperpigmentation or hypopigmentation for cosmetic purposes.

The compound of the present invention is used as it is or as a pharmaceutical composition (sometimes to be abbreviated as the "medicament of the present invention" in the present specification) formulated as a preparation together with a pharmacologically acceptable carrier by a method known per se, for example, the method described in the Japanese Pharmacopoeia.

Examples of the pharmacologically acceptable carrier include various organic or inorganic carrier substances conventionally used as a preparation material and, for example, excipient, lubricant, binder and disintegrant for solid preparations; solvent, solubilizing agent, suspending agent, isotonic agent, buffer and soothing agent for liquid preparations and the like can be mentioned. Where necessary, additives such as preservatives, antioxidizing agents, colorants, sweetening agents, adsorbent, wetting agent and the like can be used during formulation of a preparation.

Examples of the excipient include lactose, sucrose, D-mannitol, starch, cornstarch, crystalline cellulose and light anhydrous silicic acid.

Examples of the lubricant include magnesium stearate, calcium stearate, talc and colloidal silica.

Examples of the binder include crystalline cellulose, sucrose, D-mannitol, dextrin, hydroxypropylcellulose, hydroxypropylmethylcellulose, polyvinylpyrrolidone, starch, sucrose, gelatin, methylcellulose and sodium carboxymethylcellulose.

Examples of the disintegrant include starch, carboxymethylcellulose, calcium carboxymethylcellulose, croscarmellose sodium, sodium carboxymethylstarch and low-substituted hydroxypropylcellulose (L-HPC).

Examples of the solvent include water for injection, alcohol, propylene glycol, macrogol, sesame oil and corn oil.

Examples of the solubilizing agent include polyethylene glycol, propylene glycol, D-mannitol, benzyl benzoate, ethanol, trisaminomethane, cholesterol, triethanolamine, sodium carbonate and sodium citrate.

Examples of the suspending agent include surfactants such as stearyltriethanolamine, sodium lauryl sulfate, laurylaminopropionic acid, lecithin, benzalkonium chloride, benzethonium chloride, glycerol monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like.

Examples of the isotonic agent include glucose, D-sorbitol, sodium chloride, glycerol and D-mannitol.

Examples of the buffer include buffers such as phosphate, acetate, carbonate, citrate and the like.

Examples of the soothing agent include benzyl alcohol.

Examples of the preservative include p-hydroxybenzoates, chlorobutanol, benzyl alcohol, phenethyl alcohol, dehydroacetic acid and sorbic acid.

Examples of the antioxidizing agent include sulfite and ascorbic acid.

Examples of the colorant include water-soluble food tar color (e.g., food colors such as Food Color Red No. 2 and No. 3, Food Color Yellow No. 4 and No. 5, Food Color Blue No. 1 and No. 2 and the like), water-insoluble lake dye (e.g., aluminum salt of the aforementioned water-soluble food tar color), and natural dye (e.g., β-carotene, chlorophyll, ferric oxide red).

Examples of the sweetening agent include saccharin sodium, dipotassium glycyrrhizinate, aspartame and stevia.

Examples of the adsorbent include porous starch, calcium silicate (trade name: Florite RE), magnesium aluminometasilicate (trade name: Neusilin) and light anhydrous silicic acid (trade name: Sylysia).

Examples of the wetting agent include propylene glycol monostearate, sorbitan monooleate, diethylene glycol monolaurate and polyoxyethylene lauryl ether.

Examples of the dosage form of the medicament of the present invention include tablet (including sugar-coated tablet, film-coated tablet, sublingual tablet, orally disintegrating tablet, buccal tablet etc.), pill, powder, granule, capsule (including soft capsule, microcapsule), troche, syrup, liquid, emulsion, suspension, controlled-release preparation (e.g., immediate-release preparation, sustained-release preparation, sustained-release microcapsule), aerosol, film (e.g., orally disintegrable film, oral mucosal patch film), injection (e.g., subcutaneous injection, intravenous injection, intramuscular injection, intraperitoneal injection, drip infusion), transdermal absorption type preparation, ointment, lotion, adhesive preparation, suppository (e.g., rectal suppository, vaginal suppository), pellet, nasal preparation, pulmonary preparation (inhalant), eye drop and the like, and they can be administered safely by oral or parenteral administration (e.g., intravenous, intramuscular, subcutaneous, intraorgan, intranasal, intradermal, ocular instillation, intracerebral, rectal, vaginal, intraperitoneal and intratumor administrations, administration to the vicinity of tumor etc. and direct administration to the lesion).

The content of the compound of the present invention in the medicament of the present invention is, for example, about 0.1 to 100 wt % of the entire medicament of the present invention.

The dose of the compound of the present invention is appropriately determined according to the subject of administration, administration route, disease and the like.

For example, the daily dose of the compound of the present invention for oral administration to an adult patient (body weight about 60 kg) with obesity is about 0.1 to about 500 mg, preferably about 1 to about 100 mg, more preferably to about 5 to about 100 mg. This amount can be administered at once or in several portions (e.g., 1-3 times) for one day.

In an attempt to enhance the action (therapeutic effect for obesity, diabetes, depression, anxiety etc.) of the compound of the present invention and decrease the amount of the compound of the present invention to be used and the like, as well as prevent or treat complications and improve prognosis, for example, the compound of the present invention can be used in combination with a pharmaceutically active ingredient (hereinafter sometimes to be referred to as "concomitant drug") that does not adversely influence the compound of the present invention. Examples of such concomitant drug include "therapeutic agent for diabetes", "therapeutic agent for diabetic complications", "anti-obesity agent", "therapeutic agent for hypertension", "therapeutic agent for hyperlipidemia", "antiarteriosclerotic agent", "antithrombotic agent", "diuretic agent", "therapeutic agent for arthritis", "antianxiety agent", "antidepressant", "psychoneurotic agent", "sleep-inducing agent" and the like. These concomitant drugs may be low-molecular-weight compounds, or high-molecular-weight proteins, polypeptides, antibodies, vaccines or the like.

Examples of the above-mentioned "therapeutic agent for diabetes" include insulin preparations (e.g., animal insulin preparations extracted from pancreas of bovine and swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compound described in WO2007/013694, WO2007/018314, WO2008/093639 or WO2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues (e.g., sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof), dipeptidyl peptidase IV inhibitors (e.g., Alogliptin or a salt thereof (preferably, benzoate), Vildagliptin, Sitagliptin, Saxagliptin, BI1356, GRC8200, MP-513, PF-00734200, PHX1149, SK-0403, ALS2-0426, TA-6666, TS-021, KRP-104, Trelagliptin or a salt thereof (preferably, succinate), β3 agonist (e.g., N-5984), GPR40 agonist (e.g., fasiglifam or hydrate thereof (preferably, 0.5 hydrate), compound described in WO 2004/041266, WO 2004/106276, WO 2005/063729, WO 2005/063725, WO 2005/087710, WO 2005/095338, WO 2007/013689 or WO 2008/001931), GLP-1 receptor agonists (e.g., GLP-1, GLP-1MR agent, Liraglutide, Exenatide, AVE-0010, BIM-51077, Aib(8,35) hGLP-1(7,37)NH$_2$, CJC-1131, Albiglutide), amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, FBPase inhibitors), SGLT2 (sodium-glucose cotransporter 2) inhibitors (e.g., Depagliflozin, AVE2268, TS-033, YM543, TA-7284, Remogliflozin, ASP1941), SGLT1 inhibitors, 11β-hydroxysteroid dehydrogenase inhibitors (e.g., BVT-3498, INCB-13739), adiponectin or an agonist thereof, IKK inhibitors (e.g., AS-2868), leptin resistance-improving drugs, somatostatin receptor agonists, glucokinase activators (e.g., Piragliatin, AZD1656, AZD6370, TTP-355, compound described in WO2006/112549, WO2007/028135, WO2008/047821, WO2008/050821, WO2008/136428 or WO2008/156757), GIP (Glucose-dependent insulinotropic peptide), GPR119 agonists (e.g., PSN821), FGF21, FGF analogue and the like.

Examples of the above-mentioned "therapeutic agent for diabetic complications" include aldose reductase inhibitors (e.g., tolrestat, epalrestat, zopolrestat, fidarestat, CT-112, ranirestat (AS-3201), lidorestat), neurotrophic factor and increasing drugs thereof (e.g., NGF, NT-3, BDNF and neurotrophin production/secretion promoting agents described in WO01/14372 (e.g., 4-(4-chlorophenyl)-2-(2-methyl-1-imidazolyl)-5-[3-(2-methylphenoxy)propyl]oxazole), the compound described in WO2004/039365), PKC inhibitors (e.g., ruboxistaurin mesylate), AGE inhibitors (e.g., ALT946, N-phenacylthiazolium bromide (ALT766), EXO-226, Pyridorin, pyridoxamine), GABA receptor agonists (e.g., gabapentin, pregabalin), serotonin-noradrenaline reuptake inhibitors (e.g., duloxetine), sodium channel inhibitors (e.g., lacosamide), active oxygen scavengers (e.g., thioctic acid), cerebral vasodilators (e.g., tiapride, mexiletine), somatostatin receptor agonists (e.g., BIM23190), apoptosis signal regulating kinase-1 (ASK-1) inhibitor and the like.

Examples of the above-mentioned "anti-obesity agent" include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptor antagonists, GABA-modulating agents (e.g., topiramate), neuropeptide γ antagonists (e.g., velneperit), cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetyl CoA carboxylase (ACC) inhibitors, stearoyl-CoA desaturation enzyme inhibitors, microsomal triglyceride transfer protein inhibitors (e.g., R-256918), Na-glucose cotransport carrier inhibitors (e.g., JNJ-28431754, remogliflozin), NF-κB inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparation extracted from pancreas of bovine and swine; human GLP-1 preparations genetically synthesized using *Escherichia coli*, yeast; fragment or derivative of GLP-1 (e.g., exenatide, liraglutide)), amylin preparations (e.g., pramlintide, AC-2307), neuropeptide Y agonists (e.g., PYY3-36, derivative of PYY3-36, obinepitide, TM-30339, TM-30335), oxyntomodulin preparations: FGF21 preparations (e.g., animal FGF21 preparation extracted from pancreas of bovine and swine; human FGF21 preparations genetically synthesized using *Escherichia coli*, yeast; fragment or derivative of FGF21)), anorexigenic agents (e.g., P-57) and the like.

Examples of the above-mentioned "therapeutic agent for hypertension" include angiotensin converting enzyme inhibitors (e.g., captopril, enalapril, delapril), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, amlodipine, efonidipine, nicardipine, cilnidipine), (blockers (e.g., metoprolol, atenolol, propranolol, carvedilol, pindolol), clonidine and the like.

Examples of the above-mentioned "therapeutic agent for hyperlipidemia" include HMG-CoA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., the compound described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidin-4-acetic acid), fibrate compounds (e.g., bezafibrate, clofibrate, simfibrate, clinofibrate), anion exchange resins (e.g., colestyramine), probucol, nicotinic acid drugs (e.g., nicomol, niceritrol, niaspan), ethyl icosapentate, phytosterol (e.g., soysterol, γ-oryzanol), cholesterol absorption inhibitors (e.g., Zetia), CETP inhibitors (e.g., dalcetrapib, anacetrapib), ω-3 fatty acid preparations (e.g., ω-3-acid ethyl esters 90) and the like.

Examples of the above-mentioned "antiarteriosclerotic agent" include acyl coenzyme A cholesterol acyltransferase (ACAT) inhibitors (e.g., K-604), LpPLA2 inhibitors (e.g., darapladib, rilapladib), FLAP inhibitors (e.g., AM103, AM803 and the like), 5LO inhibitors (e.g., VIA-2291), sPLA2 inhibitors (e.g., A-002), apoAI mimetic peptides (e.g., D4F), HDL preparations (e.g., CSL-111) and the like.

Examples of the above-mentioned "antithrombotic agent" include heparin (e.g., heparin sodium, heparin calcium, enoxaparin sodium, dalteparin sodium), warfarin (e.g., warfarin potassium), anti-thrombin drugs (e.g., argatroban, dabigatran), FXa inhibitors (e.g., rivaroxaban, apixaban, edoxaban, YM150, the compound described in WO02/06234, WO2004/048363, WO2005/030740, WO2005/058823 or WO2005/113504), thrombolytic agents (e.g., urokinase, tisokinase, alteplase, nateplase, monteplase, pamiteplase), platelet aggregation inhibitors (e.g., ticlopidine hydrochloride, clopidogrel, prasugrel, E5555, SHC530348, cilostazol, ethyl icosapentate, beraprost sodium, sarpogrelate hydrochloride) and the like.

Examples of the above-mentioned "diuretic agent" include xanthine derivatives (e.g., theobromine sodium salicylate, theobromine calcium salicylate), thiazide preparations (e.g., ethiazide, cyclopenthiazide, trichlormethiazide, hydrochlorothiazide, hydroflumethiazide, benzylhydrochlorothiazide, penflutizide, polythiazide, methyclothiazide), antialdosterone preparations (e.g., spironolactone, triamterene), carbonic anhydrase inhibitors (e.g., acetazolamide), chlorobenzenesulfonamide preparations (e.g., chlorthalidone, mefruside, indapamide), azosemide, isosorbide, ethacrynic acid, piretanide, bumetanide, furosemide and the like.

Examples of the above-mentioned "therapeutic agent for arthritis" include ibuprofen and the like.

Examples of the above-mentioned "antianxiety agent" include alprazolam, etizolam, oxazolam, tandospirone, cloxazolam, clotiazepam, clorazepate dipotassium, chlordiazepoxide, diazepam, fludiazepam, flutazolam, flutoprazepam, prazepam, bromazepam, mexazolam, medazepam, ethyl loflazepate, lorazepam and the like.

Examples of the above-mentioned "antidepressant" include tricyclic antidepressants (e.g., imipramine, trimipramine, clomipramine, amitriptyline, nortriptyline, amoxapine, lofepramine, dosulepin, desipramine), tetracyclic antidepressants (e.g., maprotiline, mianserin, setiptiline), selective serotonin uptake inhibitors (e.g., fluoxetine, fluvoxamine, paroxetine, sertraline, escitalopram), serotonin-noradrenaline uptake inhibitors (e.g., milnacipran, duloxetine, venlafaxine), trazodone, mirtazapine, moclobemide and the like.

Examples of the above-mentioned "psychoneurotic agent" include typical antipsychotic agents (e.g., clocapramine, chlorpromazine, phenobarbital, sultopride, tiapride, thioridazine, floropipamide, mosapramine, moperone, oxypertine, carpipramine, spiperone, sulpiride, zotepine, timiperone, nemonapride, haloperidol, pimozide, prochlorperazine, propericiazine, bromperidol, perphenazine, fluphenazine maleate, mizoribine, levomepromazine), atypical antipsychotic agents (e.g., perospirone, olanzapine, quetiapine, risperidone, clozapine, aripiprazole, ziprasidone, blonanserin, lurasidone) and the like.

Examples of the above-mentioned "sleep-inducing agent" include Ramelteon, GABAergic hypnotics (e.g., brotizolam, estazolam, flurazepam, nitrazepam, triazolam, flunitrazepam, lormetazepam, rilmazafone, quazepam, zopiclone, eszopiclone, zolpidem, zaleplon, indiplon, gabaxadol); non-GABAergic hypnotics (e.g., eplivanserin, pruvanserin, diphenhydramine, trazodone, doxepin) and the like.

The administration time of the aforementioned concomitant drug is not limited, and the compound of the present invention and the concomitant drug can be administered to an administration subject simultaneously, or may be administered at staggered times. The dosage of the concomitant drug may be determined according to the dose clinically used, and can be appropriately selected depending on an administration subject, administration route, disease, combination and the like.

The administration mode of the concomitant drug is not particularly limited, and the compound of the present invention and the concomitant drug only need to be combined on administration. Examples of such administration mode include the following:

1) administration of a single preparation obtained by simultaneously processing the compound of the present invention and the concomitant drug,
2) simultaneous administration of two kinds of preparations of the compound of the present invention and the concomitant drug, which have been separately produced, by the same administration route,
3) administration of two kinds of preparations of the compound of the present invention and the concomitant drug, which have been separately produced, by the same administration route in a staggered manner,
4) simultaneous administration of two kinds of preparations of the compound of the present invention and the concomitant drug, which have been separately produced, by different administration routes,
5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The compounding ratio of the compound of the present invention to the concomitant drug can be appropriately selected depending on the administration subject, administration route, diseases and the like.

EXAMPLES

The present invention is explained in detail in the following by referring to Examples, Experimental Examples and Formulation Examples. However, the examples do not limit the present invention and the present invention can be modified within the scope of the present invention.

The "room temperature" in the following Examples is generally about 10° C. to about 35° C. The ratio for a mixed solvent is, unless otherwise specified, a volume mixing ratio and % means wt % unless otherwise specified.

In silica gel column chromatography, the indication of NH means use of aminopropylsilane-bonded silica gel. In HPLC (high performance liquid chromatography), the indication of C18 means use of octadecyl-bonded silica gel. The ratio of elution solvents is, unless otherwise specified, a volume mixing ratio.

In the following Examples, the following abbreviations are used.
DMSO: dimethyl sulfoxide
$CDCl_3$: deuterated chloroform
DMF: N,N-dimethylformamide
DMA: N,N-dimethylacetamide
$^1$H NMR (proton nuclear magnetic resonance spectrum) was measured by Fourier-transform NMR. For the analysis, ACD/SpecManager (trade name) and the like were used. Very mild peaks showing protons of hydroxy group, amino group and the like are not described.

MS (mass spectrum) was measured by LC/MS (liquid chromatography mass spectrometer). As the ionization method, ESI (ElectroSpray Ionization) method or APCI (Atmospheric Pressure Chemical Ionization) method was used as an ionization method. The data show measured values (found).

Example 1

4-[(4-chlorobenzyl)oxy]-1-(2,3-dimethyl-2H-indazol-5-yl)pyridin-2(1H)-one

A) 5-bromo-2,3-dimethyl-2H-indazole

To a solution of 5-bromo-3-methyl-1H-indazole (4.25 g) in ethyl acetate (100 ml) was added trimethyloxonium tetrafluoroborate (4.47 g) at room temperature, and the mixture was stirred at the same temperature for 5 hr. To the obtained reaction mixture was added 1 M aqueous sodium hydroxide solution, and the mixture was extracted with ethyl acetate. The organic layer was washed with saturated brine, dried over anhydrous magnesium sulfate, and concentrated under reduced pressure to give the title compound (3.65 g).

$^1$H NMR (400 MHz, DMSO-$d_6$) δ 2.58 (3H, s), 4.04 (3H, s), 7.25 (1H, d, J=9.0 Hz), 7.47 (1H, d, J=9.0 Hz), 7.94 (1H, s).

B) 4-[(4-chlorobenzyl)oxy]-1-(2,3-dimethyl-2H-indazol-5-yl)pyridin-2(1H)-one

A suspension of 5-bromo-2,3-dimethyl-2H-indazole (287 mg), 4-[(4-chlorobenzyl)oxy]pyridin-2(1H)-one (300 mg), potassium carbonate (528 m g), copper(I) iodide (242 mg) and N,N'-dimethylethylenediamine (112 mg) in DMSO (10 ml) was stirred at 150° C. for 3 hr. The reaction mixture was cooled to room temperature, added to 28% aqueous ammonia, and extracted with a 1:1 mixed solvent of ethyl acetate and tetrahydrofuran. The organic layer was washed with saturated brine, dried over anhydrous magnesium sulfate, and concentrated under reduced pressure. The obtained residue was purified by silica gel column chromatography (ethyl acetate/methanol) to give the title compound (150 mg).

MS (ESI+): [M+H]$^+$ 380.3.

$^1$H NMR (400 MHz, DMSO-$d_6$) δ 2.61 (3H, s), 4.07 (3H, s), 5.15 (2H, s), 5.97 (1H, d, J=2.3 Hz), 6.09 (1H, dd, J=7.6, 2.3 Hz), 7.10 (1H, d, J=9.2 Hz), 7.47-7.55 (5H, m), 7.60 (1H, d, J=7.5 Hz), 7.65 (1H, s).

Example 2

4-[(4-chlorobenzyl)oxy]-1-(2-ethyl-3-methyl-2H-indazol-5-yl)pyridin-2(1H)-one

A) 5-bromo-2-ethyl-3-methyl-2H-indazole

To a solution of 5-bromo-3-methyl-1H-indazole (8.44 g) in ethyl acetate (100 ml) was added dropwise triethyloxonium tetrafluoroborate (1 M dichloromethane solution, 60 ml) at room temperature, and the mixture was stirred at the same temperature overnight. To the reaction mixture was added a 1 M aqueous sodium hydroxide solution, and the mixture was extracted with ethyl acetate. The organic layer was washed with saturated brine, dried over anhydrous magnesium sulfate, and concentrated under reduced pressure. The obtained residue was purified by silica gel column chromatography (NH, hexane/ethyl acetate) to give the title compound (1.3 g).

MS (ESI+): [M+H]$^+$ 240.0.

B) 4-[(4-chlorobenzyl)oxy]-1-(2-ethyl-3-methyl-2H-indazol-5-yl)pyridin-2(1H)-one To a solution of 5-bromo-2-ethyl-3-methyl-2H-indazole (200 mg), 4-[(4-chlorobenzyl)oxy]pyridin-2(1H)-one (158 mg) and potassium carbonate (347 mg) in 1,4-dioxane (10 ml) were added copper(I) iodide (64 mg) and trans-N,N'-dimethylcyclohexane-1,2-diamine (47 mg), and the mixture was stirred at 110° C. for 16 hr. The reaction mixture was cooled to room temperature, and concentrated under reduced pressure. To the residue were added dichloromethane and water, and the organic layer was washed with saturated brine, dried over anhydrous sodium sulfate, and concentrated under reduced pressure. The obtained residue was purified by silica gel column chromatography (dichloromethane/methanol) to give the title compound (36 mg).

MS (ESI+): [M+H]$^+$ 394.2.

$^1$H NMR (400 MHz, DMSO-$d_6$) δ 1.43 (3H, t, J=7.2 Hz), 2.62 (3H, s), 4.39 (2H, q, J=7.2 Hz), 5.15 (2H, s), 5.96 (1H, d, J=2.6 Hz), 6.08 (1H, dd, J=7.6, 2.7 Hz), 7.09 (1H, dd, J=9.1, 1.9 Hz), 7.50 (4H, s), 7.55 (1H, d, J=9.1 Hz), 7.55 (1H, d, J=7.6 Hz), 7.65 (1H, d, J=1.6 Hz).

Example 3

4-[(4-chlorobenzyl)oxy]-1-(3-methyl-2-propyl-2H-indazol-5-yl)pyridin-2(1H)-one

A) 5-bromo-3-methyl-2-propyl-2H-indazole

To a suspension of 60% sodium hydride (85 mg) in N,N-dimethylformamide (10 ml) was added a solution of 5-bromo-3-methyl-1H-indazole (500 mg) in N,N-dimethylformamide (1 ml) at 0° C., and the mixture was stirred at the same temperature for 30 min. To the obtained reaction mixture was added propyl iodide (0.35 ml), and the mixture was stirred at room temperature for 3 hr. To the reaction mixture was added saturated aqueous ammonium chloride solution, and the mixture was extracted with ethyl acetate. The organic layer was washed with saturated brine, dried over anhydrous sodium sulfate, and concentrated under reduced pressure.

The obtained residue was purified by silica gel column chromatography (hexane/ethyl acetate) to give the title compound (100 mg).

$^1$H NMR (400 MHz, DMSO-$d_6$) δ 0.83-0.87 (3H, m), 1.84-1.91 (2H, m), 2.59 (3H, s), 4.29 (2H, t, J=7.0 Hz), 7.25 (1H, dd, J=9.0, 1.8 Hz), 7.48 (1H, d, J=9.0 Hz), 7.94 (1H, d, J=1.6 Hz).

B) 4-[(4-chlorobenzyl)oxy]-1-(3-methyl-2-propyl-2H-indazol-5-yl)pyridin-2(1H)-one To a solution of 5-bromo-3-methyl-2-propyl-2H-indazole (110 mg), 4-[(4-chlorobenzyl)oxy]pyridin-2(1H)-one (82 mg) and potassium carbonate (179 mg) in 1,4-dioxane (5 ml) were added copper(I) iodide (32 mg) and trans-N,N'-dimethylcyclohexane-1,2-diamine (24 mg), and the mixture was stirred at 110° C. for 16 hr. The reaction mixture was cooled to room temperature, and concentrated under reduced pressure. To the residue were added dichloromethane and water, and the organic layer was washed with saturated brine, dried over anhydrous sodium sulfate, and concentrated under reduced pressure. The obtained residue was purified by silica gel column chromatography (dichloromethane/methanol) to give the title compound (60 mg).

MS (ESI+): [M+H]$^+$ 408.0.

$^1$H NMR (400 MHz, DMSO-$d_6$) δ 0.86 (3H, t, J=7.4 Hz), 1.86-1.92 (2H, m), 2.62 (3H, s), 4.32 (2H, t, J=6.9 Hz), 5.15 (2H, s), 5.96 (1H, d, J=2.6 Hz), 6.08 (1H, dd, J=7.6, 2.7 Hz), 7.09 (1H, dd, J=9.0, 1.8 Hz), 7.50 (4H, s), 7.55 (1H, d, J=9.1 Hz), 7.60 (1H, d, J=7.6 Hz), 7.65 (1H, d, J=1.4 Hz).

Example 4

1-[(5-{4-[(4-chlorobenzyl)oxy]-2-oxopyridin-1(2H)-yl}-3-methyl-2H-indazol-2-yl)methyl]cyclopropanecarbonitrile A) (1-cyanocyclopropyl)methyl 4-methylbenzenesulfonate To a solution of 1-(hydroxymethyl)cyclopropanecarbonitrile (1.0 g) in dichloromethane (15 ml) was added pyridine (4.1 ml) at 0° C., and the mixture was stirred at the same temperature for 15 min. To the obtained reaction mixture was added dropwise p-toluenesulfonyl chloride (3.9 g), and the mixture was stirred at room temperature for 16 hr. The reaction mixture was concentrated under reduced pressure, water was added, and the mixture was extracted with dichloromethane. The organic layer was washed with saturated brine, dried over anhydrous sodium sulfate, and concentrated under reduced pressure. The obtained residue was purified by silica gel column chromatography (hexane/ethyl acetate) to give the title compound (1 g).

$^1$H NMR (400 MHz, CDCl$_3$) δ 1.06 (2H, dd, J=7.6, 5.7 Hz), 1.33-1.37 (2H, m), 2.45 (3H, s), 3.98 (2H, s), 7.36 (2H, d, J=8.1 Hz), 7.81 (2H, d, J=8.2 Hz).

B) 1-[(5-bromo-3-methyl-2H-indazol-2-yl)methyl]cyclopropanecarbonitrile

To a suspension of 60% sodium hydride (143 mg) in N,N-dimethylformamide (3 ml) was added a solution of 5-bromo-3-methyl-1H-indazole (500 mg) in N,N-dimethylformamide (1 ml) at 0° C., and the mixture was stirred at the same temperature for 30 min. To the obtained reaction mixture was added (1-cyanocyclopropyl)methyl 4-methylbenzenesulfonate (420 mg), and the mixture was stirred at room temperature for 16 hr. To the reaction mixture was added saturated aqueous ammonium chloride solution, and the mixture was extracted with dichloromethane. The organic layer was washed with saturated brine, dried over anhydrous sodium sulfate, and concentrated under reduced pressure. The obtained residue was purified by silica gel column chromatography (hexane/ethyl acetate) to give the title compound (60 mg).

MS (ESI+): [M+H]$^+$ 290.4.

C) 1-[(5-{4-[(4-chlorobenzyl)oxy]-2-oxopyridin-1(2H)-yl}-3-methyl-2H-indazol-2-yl)methyl]cyclopropanecarbonitrile The title compound was obtained according to Example 2, Step B and using 1-[(5-bromo-3-methyl-2H-indazol-2-yl)methyl]cyclopropanecarbonitrile.

MS (ESI+): [M+H]$^+$ 445.2.

Example 5

4-[(4-chlorobenzyl)oxy]-1-(2-cyclopropyl-3-methyl-2H-indazol-5-yl)pyridin-2(1H)-one A) 5-bromo-2-cyclopropyl-3-methyl-2H-indazole To a solution of 1-(5-bromo-2-nitrophenyl)ethanone (4.0 g) in toluene (41 ml) were added cyclopropylamine (2.3 ml) and titanium(IV) tetraisopropoxide (14.4 ml) at room temperature, and the mixture was stirred at 60° C. for 17 hr. The reaction mixture was concentrated, triethyl phosphite (8.4 ml) was added to the residue, and the mixture was stirred at 150° C. for 5 hr. The reaction mixture was cooled, and diluted with ethyl acetate, and 1 M aqueous sodium hydroxide solution was added. The resulting insoluble solid was filtered off, and the filtrate was extracted with ethyl acetate. The organic layer was washed with saturated brine, dried over anhydrous magnesium sulfate, and concentrated under reduced pressure. The obtained residue was purified by silica gel column chromatography (hexane/ethyl acetate) to give the title compound (2.6 g).

$^1$H NMR (400 MHz, DMSO-$d_6$) δ 1.13 (2H, d, J=5.3 Hz), 1.25 (2H, brs), 2.67 (3H, s), 3.87-3.97 (1H, m), 7.25 (1H, d, J=9.0 Hz), 7.46 (1H, d, J=9.0 Hz), 7.94 (1H, s).

B) 4-[(4-chlorobenzyl)oxy]-1-(2-cyclopropyl-3-methyl-2H-indazol-5-yl)pyridin-2(1H)-one To a suspension of 5-bromo-2-cyclopropyl-3-methyl-2H-indazole (320 mg), 4-[(4-chlorobenzyl)oxy]pyridin-2(1H)-one (200 mg) and potassium carbonate (352 mg) in DMSO (20 ml) were added copper(I) iodide (162 mg) and N,N'-dimethylethylenediamine (112 mg), and the mixture was reacted at 150° C. for 1 hr under microwave irradiation. The reaction mixture was added to 28% aqueous ammonia, and the mixture was extracted with ethyl acetate. The organic layer was washed with saturated brine, dried over anhydrous magnesium sulfate, and concentrated under reduced pressure. The obtained residue was purified by silica gel column chromatography (ethyl acetate/methanol) and recrystallized from ethyl acetate to give the title compound (134 mg).

MS (ESI+): [M+H]$^+$ 406.3.

$^1$H NMR (300 MHz, DMSO-$d_6$) δ 1.09-1.18 (2H, m), 1.22-1.30 (2H, m), 2.70 (3H, s), 3.96 (1H, dt, J=7.4, 3.6 Hz), 5.15 (2H, s), 5.97 (1H, d, J=2.6 Hz), 6.09 (1H, dd, J=7.6, 2.7

Hz), 7.09 (1H, dd, J=9.1, 2.0 Hz), 7.49-7.55 (5H, m), 7.58 (1H, d, J=7.6 Hz), 7.65 (1H, dd, J=2.0, 0.7 Hz).

Example 6

1-(2-cyclopropyl-3-methyl-2H-indazol-5-yl)-4-[(4-fluorobenzyl)oxy]pyridin-2(1H)-one To a suspension of 5-bromo-2-cyclopropyl-3-methyl-2H-indazole (2.0 g), 4-[(4-fluorobenzyl)oxy]pyridin-2(1H)-one (1.7 g) and potassium carbonate (3.3 g) in DMSO (20 ml) were added copper(I) iodide (1.5 g) and N,N'-dimethylethylenediamine (0.7 g), and the mixture was stirred at 150° C. for 3 hr. The reaction mixture was added to 28% aqueous ammonia, and the mixture was extracted with ethyl acetate. The organic layer was washed with saturated brine, dried over anhydrous magnesium sulfate, and concentrated under reduced pressure. The obtained residue was purified by silica gel column chromatography (ethyl acetate/methanol) and recrystallized from ethyl acetate to give the title compound (2.17 g).
MS (ESI+): [M+H]$^+$ 390.3.
$^1$H NMR (400 MHz, DMSO-d$_6$) δ 1.14 (2H, d, J=5.3 Hz), 1.27 (2H, brs), 2.70 (3H, s), 3.95 (1H, d, J=3.5 Hz), 5.13 (2H, s), 5.98 (1H, brs), 6.08 (1H, d, J=7.2 Hz), 7.09 (1H, d, J=8.9 Hz), 7.26 (2H, t, J=8.6 Hz), 7.49-7.61 (4H, m), 7.65 (1H, s).

Example 7

4-(benzyloxy)-1-(2-cyclopropyl-3-methyl-2H-indazol-5-yl)pyridin-2(1H)-one

To a suspension of 5-bromo-2-cyclopropyl-3-methyl-2H-indazole (187 mg), 4-(benzyloxy)pyridin-2(1H)-one (100 mg) and potassium carbonate (206 mg) in DMSO (20 ml) were added copper(I) iodide (95 mg) and N,N'-dimethylethylenediamine (65.7 mg), and the mixture was stirred at 150° C. for 3 hr. The reaction mixture was added to 28% aqueous ammonia, and the mixture was extracted with ethyl acetate. The organic layer was washed with saturated brine, dried over anhydrous magnesium sulfate, and concentrated under reduced pressure. The obtained residue was purified by silica gel column chromatography (ethyl acetate/methanol) and recrystallized from ethyl acetate to give the title compound (25 mg).
MS (ESI+): [M+H]$^+$ 372.3.
$^1$H NMR (400 MHz, DMSO-d$_6$) δ 1.10-1.19 (2H, m), 1.26 (2H, d, J=3.5 Hz), 2.70 (3H, s), 3.96 (1H, dt, J=7.1, 3.5 Hz), 5.15 (2H, s), 5.97 (1H, d, J=2.4 Hz), 6.09 (1H, dd, J=7.6, 2.6 Hz), 7.10 (1H, dd, J=9.1, 1.8 Hz), 7.33-7.50 (5H, m), 7.52 (1H, d, J=9.0 Hz), 7.58 (1H, d, J=7.5 Hz), 7.65 (1H, s).

Example 8

4-[(5-chlorothiophen-2-yl)methoxy]-1-(2-cyclopropyl-3-methyl-2H-indazol-5-yl)pyridin-2(1H)-one A) 1-(2-cyclopropyl-3-methyl-2H-indazol-5-yl)-4-hydroxypyridin-2(1H)-one To a solution of 4-(benzyloxy)-1-(2-cyclopropyl-3-methyl-2H-indazol-5-yl)pyridin-2(1H)-one (256 mg) in methanol (5 ml) was added 10% palladium carbon (100 mg) at room temperature, and the mixture was stirred under a hydrogen atmosphere at the same temperature for 1 hr. The insoluble material was filtered off through celite, and the filtrate was concentrated under reduced pressure. The obtained residue was recrystallized from ethyl acetate to give the title compound (182 mg).
MS (ESI+): [M+H]$^+$ 282.3.

B) 4-[(5-chlorothiophen-2-yl)methoxy]-1-(2-cyclopropyl-3-methyl-2H-indazol-5-yl)pyridin-2(1H)-one To a solution of 1-(2-cyclopropyl-3-methyl-2H-indazol-5-yl)-4-hydroxypyridin-2(1H)-one (70 mg) in tetrahydrofuran (5 ml) were added (5-chlorothiophen-2-yl)methanol (74 mg), 1,1'-(azodicarbonyl)dipiperidine (188 mg) and tributylphosphine (151 mg) at room temperature, and the mixture was stirred at the same temperature for 3 hr. The reaction mixture was purified by silica gel column chromatography (methanol/ethyl acetate) to give the title compound (21 mg).
MS (ESI+): [M+H]$^+$ 412.3.
$^1$H NMR (400 MHz, DMSO-d$_6$) δ 1.09-1.18 (2H, m), 1.26 (2H, d, J=3.0 Hz), 2.70 (3H, s), 3.96 (1H, dt, J=7.1, 3.4 Hz), 5.29 (2H, s), 5.99-6.07 (2H, m), 7.03-7.13 (2H, m), 7.16 (1H, d, J=3.6 Hz), 7.52 (1H, d, J=9.2 Hz), 7.58 (1H, d, J=7.5 Hz), 7.65 (1H, s).

Example 9

4-(benzyloxy)-1-(2,3-dimethyl-2H-indazol-5-yl)pyridin-2(1H)-one

A suspension of 5-bromo-2,3-dimethyl-2H-indazole (1.85 g), 4-(benzyloxy)pyridin-2(1H)-one (1.65 g), potassium carbonate (3.41 g), copper(I) iodide (1.57 g) and N,N'-dimethylethylenediamine (0.73 g) in DMSO (30 ml) was stirred at 150° C. for 3 hr. The reaction mixture was cooled to room temperature, and added to 28% aqueous ammonia, and the obtained precipitates were collected by filtration. The obtained solid was washed with water and diisopropyl ether, and dried under reduced pressure to give the title compound (1.85 g).
MS (ESI+): [M+H]$^+$ 346.3.
$^1$H NMR (400 MHz, DMSO-d$_6$) δ 2.61 (3H, s), 4.07 (3H, s), 5.15 (2H, s), 5.98 (1H, d, J=2.3 Hz), 6.09 (1H, dd, J=7.5, 2.2 Hz), 7.11 (1H, d, J=9.0 Hz), 7.32-7.50 (5H, m), 7.53 (1H, d, J=9.2 Hz), 7.59 (1H, d, J=7.5 Hz), 7.65 (1H, s).

Example 10

1-(2,3-dimethyl-2H-indazol-5-yl)-4-{[5-(trifluoromethyl)thiophen-2-yl]methoxy}pyridin-2(1H)-one A) 1-(2,3-dimethyl-2H-indazol-5-yl)-4-hydroxypyridin-2(1H)-one To a solution of 4-(benzyloxy)-1-(2,3-dimethyl-2H-indazol-5-yl)pyridin-2(1H)-one (1.8 g) in ethanol (40 ml) was added 10% palladium carbon (0.56 g), and the mixture was stirred under a hydrogen atmosphere at room temperature for 3 hr. The insoluble material was filtered off, and the obtained filtrate was concentrated under reduced pressure to give the title compound (1.04 g).
$^1$H NMR (400 MHz, DMSO-d$_6$) δ 2.60 (3H, s), 4.07 (3H, s), 5.64 (1H, d, J=1.9 Hz), 5.94 (1H, dd, J=7.5, 2.1 Hz), 7.09 (1H, dd, J=9.0, 1.5 Hz), 7.52 (2H, d, J=8.3 Hz), 7.62 (1H, s), 10.80 (1H, brs).

B) 1-(2,3-dimethyl-2H-indazol-5-yl)-4-{[5-(trifluoromethyl)thiophen-2-yl]methoxy}pyridin-2(1H)-one To a suspension of 1-(2,3-dimethyl-2H-indazol-5-yl)-4-hydroxypyridin-2(1H)-one (100 mg), [5-(trifluoromethyl)

thiophen-2-yl]methanol (143 mg) and triphenylphosphine (308 mg) in tetrahydrofuran (5 ml) was added bis(2-methoxyethyl)azodicarboxylate (275 mg) at 60° C., and the mixture was stirred at the same temperature for 3 hr. The reaction mixture was diluted with ethyl acetate, washed with water and saturated brine, dried over anhydrous magnesium sulfate, and concentrated under reduced pressure. The obtained residue was purified by silica gel column chromatography (ethyl acetate/methanol) to give the title compound (71 mg).

MS (ESI+): [M+H]+ 420.3.

$^1$H NMR (400 MHz, DMSO-$d_6$) δ 2.61 (3H, s), 4.07 (3H, s), 5.44 (2H, s), 6.03-6.14 (2H, m), 7.11 (1H, dd, J=9.0, 2.0 Hz), 7.36-7.41 (1H, m), 7.54 (1H, d, J=8.9 Hz), 7.59-7.71 (3H, m).

Example 11

4-[(4-chlorobenzyl)oxy]-1-{3-methyl-2-[(3-methyloxetan-3-yl)methyl]-2H-indazol-5-yl}pyridin-2(1H)-one A) 5-bromo-3-methyl-2-[(3-methyloxetan-3-yl)methyl]-2H-indazole The title compound was obtained according to Example 4, Step B and using (3-methyloxetan-3-yl)methyl 4-methylbenzenesulfonate.

MS (ESI+): [M+H]+ 295.2.

B) 4-[(4-chlorobenzyl)oxy]-{3-methyl-2-[(3-methyloxetan-3-yl)methyl]-2H-indazol-5-yl}pyridin-2(1H)-one The title compound was obtained according to Example 2, Step B and using 5-bromo-3-methyl-2-[(3-methyloxetan-3-yl)methyl]-2H-indazole.

MS (ESI+): [M+H]+ 450.0.

Example 12

4-[(3-chlorobenzyl)oxy]-1-(2,3-dimethyl-2H-indazol-5-yl)pyridin-2(1H)-one

To a suspension of 1-(2,3-dimethyl-2H-indazol-5-yl)-4-hydroxypyridin-2(1H)-one (50 mg), (3-chlorophenyl)methanol (56 mg) and triphenylphosphine (154 mg) in tetrahydrofuran (5 ml) was added bis(2-methoxyethyl)azodicarboxylate (138 mg) at room temperature, and the mixture was stirred at the same temperature for 3 hr. The reaction mixture was diluted with ethyl acetate, washed with water and saturated brine, dried over anhydrous magnesium sulfate, and concentrated under reduced pressure. The obtained residue was purified by silica gel column chromatography (ethyl acetate/methanol) to give the title compound (36 mg).

MS (ESI+): [M+H]+ 380.1.

$^1$H NMR (400 MHz, DMSO-$d_6$) δ 2.61 (3H, s), 4.07 (3H, s), 5.17 (2H, s), 5.97 (1H, d, J=2.0 Hz), 6.12 (1H, dd, J=7.5, 2.3 Hz), 7.11 (1H, d, J=8.9 Hz), 7.40-7.50 (3H, m), 7.54 (2H, d, J=11.3 Hz), 7.60 (1H, d, J=7.5 Hz), 7.66 (1H, s).

Example 13

4-{[5-(difluoromethyl)thiophen-2-yl]methoxy}-1-(2,3-dimethyl-2H-indazol-5-yl)pyridin-2(1H)-one A) methyl 5-(difluoromethyl)thiophene-2-carboxylate To a solution of methyl 5-formylthiophene-2-carboxylate (4.15 g) in toluene (100 ml) was added dropwise N,N-diethylaminosulfur trifluoride (4.83 ml) at 0° C., and the mixture was stirred at room temperature overnight. To the reaction mixture was added saturated aqueous sodium hydrogen carbonate solution, and the mixture was extracted with ethyl acetate. The organic layer was washed with saturated brine, dried over anhydrous magnesium sulfate, and concentrated under reduced pressure. The obtained residue was purified by silica gel column chromatography (hexane/ethyl acetate) to give the title compound (2.23 g).

$^1$H NMR (400 MHz, CDCl$_3$) δ 3.91 (3H, s), 6.83 (1H, t, J=55.8 Hz), 7.27 (1H, brs), 7.69-7.77 (1H, m).

B) [5-(difluoromethyl)thiophen-2-yl]methanol

To a mixed solution of methyl 5-(difluoromethyl)thiophene-2-carboxylate (2.23 g) in tetrahydrofuran (60 ml) and methanol (15 ml) was added sodium borohydride (2.2 g) at room temperature, and the mixture was stirred at 60° C. for 1 hr. The reaction mixture was cooled to room temperature, saturated aqueous ammonium chloride solution was added, and the mixture was extracted with ethyl acetate. The organic layer was washed with saturated brine, dried over anhydrous magnesium sulfate, and concentrated under reduced pressure. The obtained residue was purified by silica gel column chromatography (hexane/ethyl acetate) to give the title compound (1.94 g).

$^1$H NMR (400 MHz, CDCl$_3$) δ 1.86 (1H, t, J=6.0 Hz), 4.85 (2H, d, J=5.5 Hz), 6.62-6.99 (2H, m), 7.16 (1H, brs).

C) 4-{[5-(difluoromethyl)thiophen-2-yl]methoxy}-1-(2,3-dimethyl-2H-indazol-5-yl)pyridin-2(1H)-one The title compound was obtained according to Example 10, Step B and using [5-(difluoromethyl)thiophen-2-yl]methanol.

MS (ESI+): [M+H]+ 402.3.

Example 14

4-[(2-chlorobenzyl)oxy]-1-(2,3-dimethyl-2H-indazol-5-yl)pyridin-2(1H)-one

The title compound was obtained according to Example 10, Step B and using (2-chlorophenyl)methanol.

MS (ESI+): [M+H]+ 380.3.

Example 15

4-[(3,4-dichlorobenzyl)oxy]-1-(2,3-dimethyl-2H-indazol-5-yl)pyridin-2(1H)-one

The title compound was obtained according to Example 10, Step B and using (3,4-dichlorophenyl)methanol.

MS (ESI+): [M+H]+ 414.3.

Example 16

4-(1-benzofuran-2-ylmethoxy)-1-(2,3-dimethyl-2H-indazol-5-yl)pyridin-2(1H)-one

To a suspension of 1-(2,3-dimethyl-2H-indazol-5-yl)-4-hydroxypyridin-2(1H)-one (50 mg), 1-benzofuran-2-ylmethanol (58 mg) and triphenylphosphine (154 mg) in tetrahydrofuran (5 ml) was added bis(2-methoxyethyl) azodicarboxylate (138 mg) at room temperature, and the mixture was stirred at the same temperature for 3 hr. The reaction mixture was diluted with ethyl acetate, washed with water and saturated brine, dried over anhydrous magnesium sulfate, and concentrated under reduced pressure. The obtained residue was purified by silica gel column chromatography (ethyl acetate/methanol) to give the title compound (16 mg).
MS (ESI+): [M+H]$^+$ 386.3.
$^1$H NMR (400 MHz, DMSO-d$_6$) δ 2.61 (3H, s), 4.07 (3H, s), 5.33 (2H, s), 6.05-6.18 (2H, m), 7.06-7.18 (2H, m), 7.23-7.42 (2H, m), 7.50-7.75 (5H, m).

Example 17

4-(1-benzothiophen-2-ylmethoxy)-1-(2,3-dimethyl-2H-indazol-5-yl)pyridin-2(1H)-one The title compound was obtained according to Example 10, Step B and using 1-benzothiophen-2-ylmethanol.
MS (ESI+): [M+H]$^+$ 402.1.

Example 18

4-[(5-chloropyridin-2-yl)methoxy]-1-(2-cyclopropyl-3-methyl-2H-indazol-5-yl)pyridin-2(1H)-one To a solution of 1-(2-cyclopropyl-3-methyl-2H-indazol-5-yl)-4-hydroxypyridin-2(1H)-one (30 mg) in tetrahydrofuran (2 ml) were added (5-chloropyridin-2-yl)methanol (31 mg), bis(2-methoxyethyl)azodicarboxylate (55 mg) and trimethylphosphine (1 M tetrahydrofuran solution, 235 µl) at room temperature, and the mixture was stirred at the same temperature for 2 hr. The mixture was diluted with ethyl acetate, and washed with water, 1 M aqueous sodium hydroxide solution and saturated brine. The organic layer was dried over anhydrous magnesium sulfate, and concentrated under reduced pressure. The obtained residue was purified by silica gel column chromatography (NH, hexane/ethyl acetate) and recrystallized from ethyl acetate to give the title compound (22 mg).
MS (ESI+): [M+H]$^+$ 407.3.
$^1$H NMR (400 MHz, DMSO-d$_6$) δ 1.09-1.18 (2H, m), 1.26 (2H, d, J=3.4 Hz), 2.70 (3H, s), 3.92-4.00 (1H, m), 5.23 (2H, s), 5.96 (1H, d, J=2.4 Hz), 6.13 (1H, dd, J=7.5, 2.5 Hz), 7.09 (1H, dd, J=9.1, 1.7 Hz), 7.52 (1H, d, J=9.2 Hz), 7.60 (2H, d, J=7.7 Hz), 7.65 (1H, s), 8.03 (1H, dd, J=8.4, 2.4 Hz), 8.67 (1H, d, J=2.3 Hz).

Example 19

1-(2-cyclopropyl-3-methyl-2H-indazol-5-yl)-4-[(5-fluoropyridin-2-yl)methoxy]pyridin-2(1H)-one The title compound was obtained according to Example 18 and using (5-fluoropyridin-2-yl)methanol.
MS (ESI+): [M+H]$^+$ 391.3.

Example 20

4-[(4-chlorobenzyl)oxy]-1-{2-[2-(2-methoxyethoxy)ethyl]-3-methyl-2H-indazol-5-yl}pyridin-2(1H)-one A) 5-bromo-2-(2-{[tert-butyl(dimethyl)silyl]oxy}ethyl)-3-methyl-2H-indazole To a solution of 5-bromo-3-methyl-1H-indazole (2.0 g) in N,N-dimethylformamide (20 ml) were added (2-bromoethoxy)(tert-butyl)dimethylsilane (2.5 g) and 60% sodium hydride (682 mg) at 0° C., and the mixture was stirred at room temperature for 3 hr. The reaction mixture was added to water, and the mixture was extracted with ethyl acetate. The organic layer was washed with water and saturated brine, dried over anhydrous magnesium sulfate, and concentrated under reduced pressure. The obtained residue was purified by silica gel column chromatography (hexane/ethyl acetate) to give the title compound (492 mg).
$^1$H NMR (400 MHz, CDCl$_3$) δ 0.94 (9H, s), 1.72 (6H, s), 2.77 (3H, s), 4.26 (2H, t, J=5.2 Hz), 4.60 (2H, t, J=5.2 Hz), 7.44-7.48 (1H, m), 7.66 (1H, d, J=9.2 Hz), 7.87 (1H, s).

B) 1-[2-(2-{[tert-butyl(dimethyl)silyl]oxy}ethyl)-3-methyl-2H-indazol-5-yl]-4-[(4-chlorobenzyl)oxy]pyridin-2(1H)-one The title compound was obtained according to Example 5, Step B, and using 5-bromo-2-(2-{[tert-butyl(dimethyl)silyl]oxy}ethyl)-3-methyl-2H-indazole and 4-[(4-chlorobenzyl)oxy]pyridin-2(1H)-one.
$^1$H NMR (400 MHz, DMSO-d$_6$) δ −0.04-0.02 (6H, m), 0.90 (9H, s), 2.77 (3H, s), 4.18 (2H, t, J=5.0 Hz), 4.59 (2H, t, J=5.1 Hz), 5.29 (2H, s), 6.10 (1H, d, J=2.4 Hz), 6.22 (1H, dd, J=7.6, 2.6 Hz), 7.20-7.28 (1H, m), 7.63 (4H, s), 7.68 (1H, d, J=9.2 Hz), 7.72 (1H, d, J=7.5 Hz), 7.79 (1H, s).

C) 4-[(4-chlorobenzyl)oxy]-1-[2-(2-hydroxyethyl)-3-methyl-2H-indazol-5-yl]pyridin-2(1H)-one To a solution of 1-[2-(2-{[tert-butyl(dimethyl)silyl]oxy}ethyl)-3-methyl-2H-indazol-5-yl]-4-[(4-chlorobenzyl)oxy]pyridin-2(1H)-one (295 mg) in tetrahydrofuran (5 ml) was added tetra-n-butylammonium fluoride (1 M tetrahydrofuran solution, 1.13 ml) at 0° C., and the mixture was stirred at room temperature for 1 hr. The reaction mixture was added to water, and the mixture was extracted with ethyl acetate. The organic layer was washed with water and saturated brine, dried over anhydrous magnesium sulfate, and concentrated under reduced pressure. The residue was purified by silica gel column chromatography (NH, ethyl acetate/methanol) to give the title compound (221 mg).
MS (ESI+): [M+H]$^+$ 410.3.

D) 4-[(4-chlorobenzyl)oxy]-1-{2-[2-(2-methoxyethoxy)ethyl]-3-methyl-2H-indazol-5-yl}pyridin-2(1H)-one To a solution of 4-[(4-chlorobenzyl)oxy]-1-[2-(2-hydroxyethyl)-3-methyl-2H-indazol-5-yl]pyridin-2(1H)-one (30 mg) in N,N-dimethylformamide (2 ml) was added 60% sodium hydride (3.51 mg) at 0° C., and the mixture was stirred at room temperature for 30 min. To the obtained reaction mixture was added (2-bromoethyl)methyl ether (15.3 mg), and the mixture was stirred at room temperature for 2 hr. The reaction mixture was added to water, and the mixture was extracted with ethyl acetate. The organic layer was washed with water and saturated brine, dried over anhydrous magnesium sulfate, and concentrated under reduced pressure. The residue was purified by silica gel column chromatography (NH, hexane/ethyl acetate) to give the title compound (28.1 mg).
MS (ESI+): [M+H]$^+$ 468.4.

Example 21

4-[(4-chlorobenzyl)oxy]-1-[2-(2-methoxyethyl)-3-methyl-2H-indazol-5-yl]pyridin-2(1H)-one The title compound was obtained according to Example 20, Step D, and using methyl iodide.
MS (ESI+): [M+H]$^+$ 424.4.

Example 22

1-(2,3-dimethyl-2H-indazol-5-yl)-4-{[5-(trifluoromethyl)thiophen-3-yl]methoxy}pyridin-2(1H)-one

A) methyl 5-(trifluoromethyl)thiophene-3-carboxylate

To a suspension of methyl 5-iodothiophene-3-carboxylate (97 g), copper(I) iodide (137 g) and hexamethylphosphoric triamide (251 ml) in N,N-dimethylformamide (1 L) was added methyl difluoro(fluorosulfonyl)acetate (182 ml) at room temperature, and the mixture was stirred under a nitrogen atmosphere at 80° C. for 16 hr. The reaction mixture was cooled to room temperature, and the insoluble material was filtered off. The obtained filtrate was neutralized with saturated aqueous sodium hydrogen carbonate solution. The resulting insoluble material was filtered off through celite, and the filtrate was extracted with ethyl acetate. The organic layer was washed with saturated brine, dried over anhydrous magnesium sulfate, and concentrated under reduced pressure. The obtained residue was purified by silica gel column chromatography (hexane/toluene) to give the title compound (71.2 g) as a yellow oil.

$^1$H NMR (400 MHz, CDCl$_3$) δ 3.90 (3H, s) 7.86 (1H, s) 8.23 (1H, d, J=1.3 Hz).

B) [5-(trifluoromethyl)thiophen-3-yl]methanol

To a suspension of lithium borohydride (15.9 g) in tetrahydrofuran (550 ml) was added dropwise a solution of methyl 5-(trifluoromethyl)thiophene-3-carboxylate (55.1 g) in tetrahydrofuran (50 ml) at 0° C., and the obtained mixture was stirred at 50° C. overnight. The reaction mixture was cooled to 0° C., poured into 2 M hydrochloric acid, and the mixture was extracted with ethyl acetate. The organic layer was washed with saturated brine, dried over anhydrous magnesium sulfate, and concentrated under reduced pressure. The obtained residue was purified by silica gel column chromatography (hexane/ethyl acetate) to give the title compound (37.3 g).

$^1$H NMR (400 MHz, CDCl$_3$) δ 4.70 (2H, s), 7.39 (1H, d, J=0.6 Hz), 7.44 (1H, s).

C) 1-(2,3-dimethyl-2H-indazol-5-yl)-4-{[5-(trifluoromethyl)thiophen-3-yl]methoxy}pyridin-2(1H)-one To a suspension of 1-(2,3-dimethyl-2H-indazol-5-yl)-4-hydroxypyridin-2(1H)-one (50 mg), [5-(trifluoromethyl)thiophen-3-yl]methanol (71 mg) and triphenylphosphine (154 mg) in tetrahydrofuran (5 ml) was added bis(2-methoxyethyl)azodicarboxylate (138 mg) at room temperature, and the mixture was stirred at the same temperature for 3 hr. To the reaction mixture was added water, and the mixture was extracted with ethyl acetate. The organic layer was washed with saturated brine, dried over anhydrous magnesium sulfate, and concentrated under reduced pressure. The obtained residue was purified by silica gel column chromatography (hexane/ethyl acetate/methanol) and recrystallized from ethanol-hexane to give the title compound (35 mg).

MS (ESI+): [M+H]$^+$ 420.3.

$^1$H NMR (400 MHz, DMSO-d$_6$) δ 2.61 (3H, s) 4.07 (3H, s) 5.16 (2H, s) 6.01 (1H, s) 6.09 (1H, d, J=7.7 Hz) 7.11 (1H, d, J=9.3 Hz) 7.54 (1H, d, J=8.9 Hz) 7.60 (1H, d, J=7.5 Hz) 7.65 (1H, s) 7.81 (1H, s) 8.06 (1H, s).

Example 23

4-[(5-bromopyridin-2-yl)methoxy]-1-(2,3-dimethyl-2H-indazol-5-yl)pyridin-2(1H)-one To a suspension of 1-(2,3-dimethyl-2H-indazol-5-yl)-4-hydroxypyridin-2(1H)-one (50 mg), (5-bromopyridin-2-yl)methanol (74 mg) and triphenylphosphine (154 mg) in tetrahydrofuran (5 ml) was added bis(2-methoxyethyl) azodicarboxylate (138 mg) at room temperature, and the mixture was stirred at the same temperature for 3 hr. To the reaction mixture was added water, and the mixture was extracted with ethyl acetate. The organic layer was washed with saturated brine, dried over anhydrous magnesium sulfate, and concentrated under reduced pressure. The obtained residue was washed with ethyl acetate, and recrystallized from ethanol-hexane to give the title compound (51 mg).

MS (ESI+): [M+H]$^+$ 425.3.

$^1$H NMR (400 MHz, DMSO-d$_6$) δ 2.61 (3H, s), 4.07 (3H, s), 5.21 (2H, s), 5.96 (1H, d, J=2.4 Hz), 6.13 (1H, dd, J=7.7, 2.3 Hz), 7.02-7.16 (1H, m), 7.54 (2H, dd, J=8.5, 5.1 Hz), 7.61 (1H, d, J=7.5 Hz), 7.66 (1H, s), 8.15 (1H, dd, J=8.3, 2.3 Hz), 8.75 (1H, d, J=2.0 Hz).

Example 24

4-[(4-tert-butylbenzyl)oxy]-1-(2,3-dimethyl-2H-indazol-5-yl)pyridin-2(1H)-one To a solution of 1-(2,3-dimethyl-2H-indazol-5-yl)-4-hydroxypyridin-2(1H)-one (100 mg) in N,N-dimethylformamide (2 ml) were added 1-(bromomethyl)-4-(tert-butyl)benzene (98 mg) and potassium carbonate (108 mg) at room temperature, and the mixture was stirred at the same temperature for 18 hr. The reaction mixture was added to water, and the mixture was extracted with ethyl acetate. The organic layer was washed with water and saturated brine, dried over anhydrous magnesium sulfate, and concentrated under reduced pressure. The residue was purified by silica gel column chromatography (NH, ethyl acetate/methanol) and recrystallized from ethyl acetate to give the title compound (40 mg).

MS (ESI+): [M+H]$^+$ 402.4.

Example 25

4-[(4-bromobenzyl)oxy]-1-(2,3-dimethyl-2H-indazol-5-yl)pyridin-2(1H)-one

To a solution of 1-(2,3-dimethyl-2H-indazol-5-yl)-4-hydroxypyridin-2(1H)-one (150 mg) in tetrahydrofuran (3 ml) were added (4-bromophenyl)methanol (110 mg), bis(2-methoxyethyl)azodicarboxylate (179 mg) and triphenylphosphine (200 mg) at room temperature, and the mixture was stirred at the same temperature for 17 hr. To the reaction mixture was added water, and the mixture was extracted with ethyl acetate. The organic layer was washed with water and saturated brine, dried over anhydrous magnesium sulfate, and concentrated under reduced pressure. The residue was purified by silica gel column chromatography (hexane/ethyl acetate) and recrystallized from ethyl acetate to give the title compound (98 mg).

MS (ESI+): [M+H]$^+$ 424.3.

$^1$H NMR (400 MHz, DMSO-d$_6$) δ 2.61 (3H, s), 4.07 (3H, s), 5.14 (2H, s), 5.96 (1H, d, J=2.4 Hz), 6.09 (1H, dd, J=7.5, 2.5 Hz), 7.10 (1H, dd, J=9.1, 1.7 Hz), 7.43 (2H, d, J=8.3 Hz), 7.53 (1H, d, J=9.0 Hz), 7.57-7.69 (4H, m).

Example 26

1-(2,3-dimethyl-2H-indazol-5-yl)-4-[(4-isopropyl-benzyl)oxy]pyridin-2(1H)-one

The title compound was obtained according to Example 24, and using 1-(bromomethyl)-4-(isopropyl)benzene.
MS (ESI+): [M+H]+ 388.3.

Example 27

4-[(5-bromothiophen-2-yl)methoxy]-1-(2,3-dimethyl-2H-indazol-5-yl)pyridin-2(1H)-one To a suspension of 1-(2,3-dimethyl-2H-indazol-5-yl)-4-hydroxypyridin-2(1H)-one (50 mg), (5-bromothiophen-2-yl) methanol (76 mg) and triphenylphosphine (154 mg) in tetrahydrofuran (5 ml) was added bis(2-methoxyethyl) azodicarboxylate (138 mg) at room temperature, and the mixture was stirred at the same temperature for 3 hr. The reaction mixture was diluted with ethyl acetate, washed with water and saturated brine, dried over anhydrous magnesium sulfate, and concentrated under reduced pressure. The obtained residue was purified by silica gel column chromatography (ethyl acetate/methanol) to give the title compound (13 mg).
MS (ESI+): [M+H]+ 430.2.
$^1$H NMR (400 MHz, DMSO-$d_6$) δ 2.61 (3H, s), 4.07 (3H, s), 5.31 (2H, s), 6.00-6.09 (2H, m), 7.07-7.16 (2H, m), 7.19 (1H, d, J=3.5 Hz), 7.53 (1H, d, J=9.0 Hz), 7.59 (1H, d, J=7.4 Hz), 7.66 (1H, s).

Example 28

4-[(5-bromopyridin-2-yl)methoxy]-1-(2-cyclopropyl-3-methyl-2H-indazol-5-yl)pyridin-2(1H)-one To a suspension of 1-(2-cyclopropyl-3-methyl-2H-indazol-5-yl)-4-hydroxypyridin-2(1H)-one (50 mg), (5-bromopyridin-2-yl)methanol (67 mg) and triphenylphosphine (140 mg) in tetrahydrofuran (6 ml) was added bis(2-methoxyethyl)azodicarboxylate (125 mg) at room temperature, and the mixture was stirred at the same temperature for 3 hr. To the reaction mixture was added water, and the mixture was extracted with ethyl acetate. The organic layer was washed with saturated brine, dried over anhydrous magnesium sulfate, and concentrated under reduced pressure. The obtained residue was purified by silica gel column chromatography (hexane/ethyl acetate/methanol) and recrystallized from ethanol-hexane to give the title compound (34 mg).
MS (ESI+): [M+H]+ 452.3.
$^1$H NMR (400 MHz, DMSO-$d_6$) δ 1.14 (2H, d, J=4.9 Hz), 1.27 (2H, brs), 2.70 (3H, s), 3.96 (1H, brs), 5.21 (2H, s), 5.95 (1H, s), 6.13 (1H, d, J=6.8 Hz), 7.09 (1H, d, J=8.5 Hz), 7.53 (2H, t, J=8.7 Hz), 7.60 (1H, d, J=7.7 Hz), 7.65 (1H, s), 8.14 (1H, d, J=8.3 Hz), 8.75 (1H, s).

Example 29

4-[(4-chlorophenoxy)methyl]-1-(2,3-dimethyl-2H-indazol-5-yl)pyridin-2(1H)-one

A) methyl 1-(2,3-dimethyl-2H-indazol-5-yl)-2-oxo-1,2-dihydropyridine-4-carboxylate The title compound was obtained according to Example 2, Step B, and using 5-bromo-2,3-dimethyl-2H-indazole and methyl 2-oxo-1,2-dihydropyridine-4-carboxylate.
MS (ESI+): [M+H]+ 298.2.

B) 1-(2,3-dimethyl-2H-indazol-5-yl)-4-(hydroxymethyl)pyridin-2(1H)-one

To a solution of methyl 1-(2,3-dimethyl-2H-indazol-5-yl)-2-oxo-1,2-dihydropyridine-4-carboxylate (450 mg) in dichloromethane (40 ml) was added diisobutylaluminum hydride (1 M toluene solution, 7.5 ml) at −78° C., and the mixture was stirred at the same temperature for 2 hr. To the reaction mixture were added methanol and water at the same temperature, and the mixture was filtered through celite, and concentrated under reduced pressure. The obtained residue was purified by silica gel column chromatography (dichloromethane/methanol) to give the title compound (220 mg).
MS (ESI+): [M+H]+ 270.0.

C) [1-(2,3-dimethyl-2H-indazol-5-yl)-2-oxo-1,2-dihydropyridin-4-yl]methyl methanesulfonate To a solution of 1-(2,3-dimethyl-2H-indazol-5-yl)-4-(hydroxymethyl)pyridin-2(1H)-one (100 mg) in dichloromethane (5 ml) was added triethylamine (0.153 ml) at 0° C., and the mixture was stirred at the same temperature for 30 min. To the obtained reaction mixture was added methanesulfonyl chloride (0.057 ml) at 0° C., and the mixture was stirred at room temperature for 4 hr. The reaction mixture was concentrated under reduced pressure, water was added, and the mixture was extracted with dichloromethane. The organic layer was washed with saturated brine, dried over anhydrous sodium sulfate, and concentrated under reduced pressure. The obtained residue was purified by silica gel column chromatography (hexane/ethyl acetate) to give the title compound (120 mg).
MS (ESI+): [M+H]+ 348.4.

D) 4-[(4-chlorophenoxy)methyl]-1-(2,3-dimethyl-2H-indazol-5-yl)pyridin-2(1H)-one To a solution of [1-(2,3-dimethyl-2H-indazol-5-yl)-2-oxo-1,2-dihydropyridin-4-yl]methyl methanesulfonate (140 mg) and 4-chlorophenol (77 mg) in N,N-dimethylformamide (5 ml) was added potassium carbonate (120 mg) at room temperature, and the mixture was stirred at 80° C. for 4 hr. The reaction mixture was concentrated under reduced pressure, and the obtained residue was purified by silica gel column chromatography (dichloromethane/methanol). The obtained residue was purified by HPLC to give the title compound (20 mg).
MS (ESI+): [M+H]+ 380.2.

Example 30

4-[(4-bromo-1,3-thiazol-2-yl)methoxy]-1-(2,3-dimethyl-2H-indazol-5-yl)pyridin-2(1H)-one To a suspension of 1-(2,3-dimethyl-2H-indazol-5-yl)-4-hydroxypyridin-2(1H)-one (50 mg), (4-bromo-1,3-thiazol-2-yl)methanol (76 mg) and triphenylphosphine (154 mg) in tetrahydrofuran (6 ml) was added bis(2-methoxyethyl)azodicarboxylate (138 mg) at room temperature, and the mixture was stirred at the same temperature for 3 hr. To the reaction mixture was added water, and the mixture was extracted with ethyl acetate. The organic layer was washed with saturated brine, dried over anhydrous magnesium sulfate, and concentrated under reduced pressure. The obtained residue was purified by silica gel column chromatography (hexane/ethyl acetate/methanol) and recrystallized from ethanol-hexane to give the title compound (45 mg).
MS (ESI+): [M+H]⁺ 432.2.
¹H NMR (400 MHz, DMSO-$d_6$) δ 2.61 (3H, s), 4.07 (3H, s), 5.50 (2H, s), 6.05 (1H, brs), 6.14 (1H, d, J=6.2 Hz), 7.11 (1H, d, J=9.4 Hz), 7.54 (1H, d, J=9.2 Hz), 7.60-7.71 (2H, m), 7.95 (1H, s).

Example 31

4-[(4-chlorobenzyl)oxy]-1-(6-fluoro-2,3-dimethyl-2H-indazol-5-yl)pyridin-2(1H)-one A) 5-bromo-6-fluoro-3-methyl-1H-indazole To a solution of 1-(5-bromo-2,4-difluorophenyl)ethanone (4.9 g) in ethylene glycol (15 ml) was added hydrazine monohydrate (1.2 g) at room temperature, and the mixture was stirred at 160° C. for 26 hr. The reaction mixture was cooled to room temperature, and the insoluble material was removed. The filtrate was added to water, and the mixture was extracted with ethyl acetate. The organic layer was washed with saturated aqueous ammonium chloride solution, saturated aqueous sodium hydrogen carbonate solution and saturated brine, dried over anhydrous magnesium sulfate, and concentrated under reduced pressure. The residue was purified by silica gel column chromatography (hexane/ethyl acetate) to give the title compound (3.2 g).
MS (ESI+): [M+H]⁺ 229.9.

B) 5-bromo-6-fluoro-2,3-dimethyl-2H-indazole

The title compound was obtained according to Example 1, Step A, and using 5-bromo-6-fluoro-3-methyl-1H-indazole.
MS (ESI+): [M+H]⁺243.0.

C) 4-[(4-chlorobenzyl)oxy]-1-(6-fluoro-2,3-dimethyl-2H-indazol-5-yl)pyridin-2(1H)-one The title compound was obtained according to Example 5, Step B, and using 5-bromo-6-fluoro-2,3-dimethyl-2H-indazole.
MS (ESI+): [M+H]⁺ 398.3.

Example 32

4-[(4-chlorobenzyl)oxy]-1-(4-fluoro-2,3-dimethyl-2H-indazol-5-yl)pyridin-2(1H)-one A) 1-(3-bromo-2,6-difluorophenyl)ethanol To a solution of 3-bromo-2,6-difluorobenzaldehyde (5 g) in tetrahydrofuran (50 ml) was added dropwise methylmagnesium bromide (1 M tetrahydrofuran solution, 24.9 ml) at 0° C., and the mixture was stirred for 30 min. The reaction mixture was added to water, and the mixture was extracted with ethyl acetate. The organic layer was washed with saturated aqueous ammonium chloride solution and saturated brine, dried over anhydrous magnesium sulfate, and concentrated under reduced pressure. The residue was purified by silica gel column chromatography (hexane/ethyl acetate) to give the title compound (4.91 g).
¹H NMR (400 MHz, CDCl₃) δ 1.64 (3H, d, J=6.7 Hz), 2.19 (1H, d, J=8.4 Hz), 5.26 (1H, quin, J=7.1 Hz), 6.81 (1H, t, J=9.3 Hz), 7.37-7.50 (LH, m).

B) 1-(3-bromo-2,6-difluorophenyl)ethanone

To a solution of 1-(3-bromo-2,6-difluorophenyl)ethanol (3.91 g) in acetonitrile (50 ml) was added manganese dioxide (2.87 g) at room temperature, and the mixture was heated under reflux for 20 hr. The reaction mixture was cooled, the insoluble material was filtered off, and the obtained filtrate was concentrated under reduced pressure. The residue was purified by silica gel column chromatography (hexane/ethyl acetate) to give the title compound (3.48 g).
¹H NMR (400 MHz, CDCl₃) δ 2.61 (3H, s), 6.90 (LH, t, J=8.9 Hz), 7.53-7.66 (1H, m).

C) 5-bromo-4-fluoro-2,3-dimethyl-2H-indazole

To a solution of 1-(3-bromo-2,6-difluorophenyl)ethanone (4.25 g) in n-butanol (50 ml) was added hydrazine monohydrate (1.06 ml) at room temperature, and the mixture was heated under reflux for 20 hr. The reaction mixture was cooled, and added to water, and the mixture was extracted with ethyl acetate. The obtained organic layer was washed with saturated aqueous sodium hydrogen carbonate solution and saturated brine, dried over anhydrous magnesium sulfate, and concentrated under reduced pressure. The residue was purified by silica gel column chromatography (hexane/ethyl acetate). The residue was dissolved in ethyl acetate (50 ml), trimethyloxonium tetrafluoroborate (4.01 g) was added at room temperature, and the mixture was stirred at the same temperature for 3 hr. The reaction mixture was added dropwise to water, and the mixture was extracted with ethyl acetate. The organic layer was washed with water and saturated brine, dried over anhydrous magnesium sulfate, and concentrated under reduced pressure. The residue was purified by silica gel column chromatography (hexane/ethyl acetate) to give the title compound (224 mg).
MS (ESI+): [M+H]⁺243.0.

D) 4-[(4-chlorobenzyl)oxy]-1-(4-fluoro-2,3-dimethyl-2H-indazol-5-yl)pyridin-2(1H)-one To a suspension of 5-bromo-4-fluoro-2,3-dimethyl-2H-indazole (142 mg), 4-[(4-chlorobenzyl)oxy]pyridin-2(1H)-one (138 mg) and potassium carbonate (242 mg) in DMSO (3 ml) were added copper(I) iodide (111 mg) and N,N'-dimethylethylenediamine (103 mg) at room temperature, and the mixture was reacted at 150° C. for 1 hr under microwave irradiation. The reaction mixture was added to 28% aqueous ammonia, and the mixture was extracted with ethyl acetate. The organic layer was washed with saturated brine, dried over anhydrous magnesium sulfate, and concentrated under reduced pressure. The obtained residue was purified by silica gel column chromatography (ethyl acetate/methanol) and recrystallized from ethyl acetate to give the title compound (6.8 mg).
MS (ESI+): [M+H]⁺ 398.3.
¹H NMR (400 MHz, CDCl₃) δ 2.72 (3H, s), 4.09 (3H, s), 5.01 (2H, s), 6.02-6.09 (2H, m), 7.08 (1H, t, J=8.0 Hz), 7.21 (1H, d, J=7.7 Hz), 7.32-7.48 (5H, m).

Example 33

1-(2-cyclopropyl-3-methyl-2H-indazol-5-yl)-4-{[4-(trifluoromethyl)-1,3-thiazol-2-yl]methoxy}pyridin-2(1H)-one To a suspension of 1-(2-cyclopropyl-3-methyl-2H-indazol-5-yl)-4-hydroxypyridin-2(1H)-one (50 mg), [4-(trifluoromethyl)-1,3-thiazol-2-yl]methanol (65 mg) and triphenylphosphine (140 mg) in tetrahydrofuran (6 ml) was added bis(2-methoxyethyl)azodicarboxylate (125 mg) at room temperature, and the mixture was stirred at the same temperature for 3 hr.

The reaction mixture was added to water, and the mixture was extracted with ethyl acetate. The organic layer was washed with saturated brine, dried over anhydrous magnesium sulfate, and concentrated under reduced pressure. The obtained residue was purified by silica gel column chromatography (hexane/ethyl acetate/methanol) and recrystallized from 2-propanol-diisopropyl ether to give the title compound (18 mg).

MS (ESI+): [M+H]$^+$ 447.3.

$^1$H NMR (400 MHz, DMSO-d$_6$) δ 1.15 (2H, d, J=5.4 Hz), 1.27 (2H, brs), 2.70 (3H, s), 3.96 (1H, brs), 5.56 (2H, s), 6.07 (1H, brs), 6.16 (1H, d, J=7.0 Hz), 7.11 (1H, d, J=8.8 Hz), 7.53 (1H, d, J=8.8 Hz), 7.58-7.73 (2H, m), 8.61 (1H, s).

Example 34

4-(benzyloxy)-1-(2-ethyl-3-methyl-2H-indazol-5-yl) pyridin-2(1H)-one

The title compound was obtained according to Example 1, Step B, and using 5-bromo-2-ethyl-3-methyl-2H-indazole and 4-(benzyloxy)pyridin-2(1H)-one.

MS (ESI+): [M+H]$^+$ 360.2.

Example 35

1-(2-ethyl-3-methyl-2H-indazol-5-yl)-4-{[4-(pentafluoro-λ$^6$-sulfanyl)benzyl]oxy}pyridin-2(1H)-one To a solution of 4-bromo-1-(2-ethyl-3-methyl-2H-indazol-5-yl)pyridin-2(1H)-one (200 mg) in toluene (10 ml) were added potassium tert-butoxide (203 mg) and [4-(pentafluoro-X$^6$-sulfanyl)phenyl]methanol (211 mg) at 80° C., and the mixture was stirred at the same temperature for 1 hr. The reaction mixture was cooled to room temperature, water was added, and the mixture was extracted with ethyl acetate. The organic layer was washed with saturated aqueous sodium hydrogen carbonate solution and saturated brine, dried over anhydrous magnesium sulfate, and concentrated under reduced pressure. The obtained residue was purified by silica gel column chromatography (NH, hexane/ethyl acetate) to give the title compound (82 mg).

MS (ESI+): [M+H]$^+$ 486.3.

Example 36

1-(2-ethyl-3-methyl-2H-indazol-5-yl)-4-{[4-(trifluoromethyl)-1,3-thiazol-2-yl]methoxy}pyridin-2(1H)-one A) 1-(2-ethyl-3-methyl-2H-indazol-5-yl)-4-hydroxypyridin-2(1H)-one A suspension of 4-(benzyloxy)-1-(2-ethyl-3-methyl-2H-indazol-5-yl)pyridin-2(1H)-one (1.5 g) and 10% palladium carbon (444 mg) in methanol (30 ml) was stirred under a hydrogen atmosphere at room temperature for 3 hr. The insoluble material was filtered off, and the obtained filtrate was concentrated under reduced pressure to give the title compound (1.07 g).

MS (ESI+): [M+H]$^+$ 270.1.

B) 4-bromo-1-(2-ethyl-3-methyl-2H-indazol-5-yl) pyridin-2(1H)-one

To a solution of 1-(2-ethyl-3-methyl-2H-indazol-5-yl)-4-hydroxypyridin-2(1H)-one (1.07 g) in N,N-dimethylformamide (20 ml) was added phosphorus oxybromide (1.37 g) at room temperature, and the mixture was stirred at 50° C. overnight. The reaction mixture was cooled to room temperature, saturated aqueous sodium hydrogen carbonate solution was added, and the mixture was extracted with ethyl acetate. The organic layer was washed with saturated brine, dried over anhydrous magnesium sulfate, and concentrated under reduced pressure. The obtained residue was recrystallized from ethanol-hexane to give the title compound (680 mg).

MS (ESI+): [M+H]$^+$ 333.1.

C) ethyl 4-(trifluoromethyl)-1,3-thiazole-2-carboxylate

A solution of ethyl amino(thioxo)acetate (4 g) and 3-bromo-1,1,1-trifluoroacetone (3.1 ml) in ethanol (150 ml) was heated under reflux overnight. The reaction mixture was concentrated under reduced pressure, and the residue was diluted with water and extracted with ethyl acetate. The organic layer was washed with saturated brine, dried over anhydrous magnesium sulfate, and concentrated under reduced pressure. The obtained residue was purified by silica gel column chromatography (NH, hexane/ethyl acetate) to give the title compound (3.56 g).

$^1$H NMR (400 MHz, CDCl$_3$) δ 1.46 (3H, t, J=7.1 Hz), 4.52 (2H, q, J=7.1 Hz), 8.03 (1H, s).

D) [4-(trifluoromethyl)-1,3-thiazol-2-yl]methanol

Sodium tetrahydroborate (840 mg) was added to a solution of ethyl 4-(trifluoromethyl)-1,3-thiazole-2-carboxylate (2.5 g) in methanol (15 ml) at 0° C., and the mixture was stirred at the same temperature for 2 hr. The reaction mixture was concentrated under reduced pressure, and the residue was diluted with water and extracted with ethyl acetate. The organic layer was washed with saturated brine, dried over anhydrous magnesium sulfate, and concentrated under reduced pressure. The obtained residue was purified by silica gel column chromatography (NH, hexane/ethyl acetate) to give the title compound (1.7 g).

$^1$H NMR (400 MHz, DMSO-d$_6$) δ 4.78 (2H, d, J=5.5 Hz), 6.28 (1H, t, J=5.6 Hz), 8.41 (1H, s).

E) 1-(2-ethyl-3-methyl-2H-indazol-5-yl)-4-{[4-(trifluoromethyl)-1,3-thiazol-2-yl]methoxy}pyridin-2 (1H)-one To a solution of 4-bromo-1-(2-ethyl-3-methyl-2H-indazol-5-yl)pyridin-2(1H)-one (350 mg) and [4-(trifluoromethyl)-1,3-thiazol-2-yl]methanol (289 mg) in toluene (5 ml) was added potassium tert-butoxide (355 mg) at room temperature, and the mixture was stirred at 100° C. for 2 hr. The reaction mixture was cooled to room temperature, water was added, and the mixture was extracted with ethyl acetate. The organic layer was washed with saturated brine, dried over anhydrous magnesium sulfate, and concentrated under reduced pressure. The obtained residue was purified by silica gel column chromatography (NH, hexane/ethyl acetate) and recrystallized from ethanol-water to give the title compound (75 mg).

MS (ESI+): [M+H]$^+$ 435.1.

$^1$H NMR (400 MHz, DMSO-d$_6$) δ 1.44 (3H, t, J=7.3 Hz), 2.63 (3H, s), 4.29-4.46 (2H, m), 5.56 (2H, s), 6.08 (1H, s), 6.16 (1H, d, J=5.0 Hz), 7.11 (1H, d, J=9.0 Hz), 7.56 (LH, d, J=9.0 Hz), 7.61-7.71 (2H, m), 8.61 (1H, s).

Example 37

1-(2-ethyl-3-methyl-2H-indazol-5-yl)-4-[(4-fluorobenzyl)oxy]pyridin-2(1H)-one

The title compound was obtained according to Example 36, Step E, and using 4-fluorobenzyl alcohol.
MS (ESI+): [M+H]$^+$ 378.1.

Example 38

1-(2,3-dimethyl-2H-indazol-5-yl)-4-{[4-(trifluoromethyl)-1,3-thiazol-2-yl]methoxy}pyridin-2(1H)-one To a suspension of 1-(2,3-dimethyl-2H-indazol-5-yl)-4-hydroxypyridin-2(1H)-one (65 mg), [4-(trifluoromethyl)-1,3-thiazol-2-yl]methanol (73 mg) and triphenylphosphine (156 mg) in tetrahydrofuran (6 ml) was added bis(2-methoxyethyl)azodicarboxylate (140 mg) at room temperature, and the mixture was stirred at the same temperature for 3 hr. To the reaction mixture was added water, and the mixture was extracted with ethyl acetate. The organic layer was washed with saturated brine, dried over anhydrous magnesium sulfate, and concentrated under reduced pressure. The obtained residue was purified by silica gel column chromatography (hexane/ethyl acetate/methanol) and recrystallized from 2-propanol-diisopropyl ether to give the title compound (42 mg).
MS (ESI+): [M+H]$^+$ 421.3.
$^1$H NMR (400 MHz, DMSO-d$_6$) δ 2.61 (3H, s), 4.07 (3H, s), 5.56 (2H, s), 6.08 (1H, s), 6.16 (1H, d, J=9.8 Hz), 7.11 (1H, d, J=8.9 Hz), 7.54 (1H, d, J=8.9 Hz), 7.66 (2H, d, J=11.7 Hz), 8.61 (1H, s).

Example 39

1-(2,3-dimethyl-2H-indazol-5-yl)-4-{[2-(trifluoromethyl)-1,3-thiazol-4-yl]methoxy}pyridin-2(1H)-one To a suspension of 1-(2,3-dimethyl-2H-indazol-5-yl)-4-hydroxypyridin-2(1H)-one (63 mg), [2-(trifluoromethyl)-1,3-thiazol-4-yl]methanol (90 mg) and triphenylphosphine (193 mg) in tetrahydrofuran (6 ml) was added bis(2-methoxyethyl)azodicarboxylate (173 mg) at room temperature, and the mixture was stirred at the same temperature for 3 hr. The reaction mixture was diluted with ethyl acetate, washed with water and saturated brine, dried over anhydrous magnesium sulfate, and concentrated under reduced pressure. The obtained residue was purified by silica gel column chromatography (ethyl acetate/methanol) to give the title compound (13 mg).
MS (ESI+): [M+H]$^+$ 421.3.
$^1$H NMR (400 MHz, DMSO-d$_6$) δ 2.61 (3H, s), 4.07 (3H, s), 5.32 (2H, s), 6.05-6.14 (2H, m), 7.11 (1H, d, J=8.9 Hz), 7.54 (1H, d, J=9.2 Hz), 7.61 (1H, d, J=7.4 Hz), 7.66 (1H, s), 8.33 (1H, s).

Example 40

1-(2,3-dimethyl-2H-indazol-5-yl)-4-{[5-(trifluoromethyl)pyrazin-2-yl]methoxy}pyridin-2(1H)-one A) 2-(bromomethyl)-5-(trifluoromethyl)pyrazine To a solution of 2-methyl-5-(trifluoromethyl)pyrazine (1 g) in trifluoromethylbenzene (10 ml) was added N-bromosuccinimide (1.21 g) at room temperature, and the mixture to was stirred at 90° C. for 30 min. To the obtained reaction mixture was added azobisisobutyronitrile (0.051 g), and the mixture was stirred at the same temperature for 7 hr. The reaction mixture was cooled and concentrated under reduced pressure, and the residue was purified by silica gel column chromatography (hexane/ethyl acetate) to give the title compound (404 mg).
$^1$H NMR (400 MHz, DMSO-d$_6$) δ 4.88 (2H, s), 9.03 (1H, s), 9.20 (1H, s).

B) 1-(2,3-dimethyl-2H-indazol-5-yl)-4-{[5-(trifluoromethyl)pyrazin-2-yl]methoxy}pyridin-2(1H)-one The title compound was obtained according to Example 24 and using 1-(2,3-dimethyl-2H-indazol-5-yl)-4-hydroxypyridin-2(1H)-one and 2-(bromomethyl)-5-(trifluoromethyl)pyrazine.
MS (ESI+): [M+H]$^+$ 416.1.

Example 41

1-(2,3-dimethyl-2H-indazol-5-yl)-4-{[4-(trifluoromethyl)thiophen-2-yl]methoxy}pyridin-2(1H)-one To a suspension of 1-(2,3-dimethyl-2H-indazol-5-yl)-4-hydroxypyridin-2(1H)-one (70 mg), [4-(trifluoromethyl)thiophen-2-yl]methanol (50 mg) and triphenylphosphine (144 mg) in tetrahydrofuran (3 ml) was added bis(2-methoxyethyl)azodicarboxylate (129 mg) at room temperature, and the mixture was stirred at the same temperature for 3 hr. The reaction mixture was diluted with ethyl acetate, washed with water and saturated brine, dried over anhydrous magnesium sulfate, and concentrated under reduced pressure. The obtained residue was purified by silica gel column chromatography (ethyl acetate/methanol) to give the title compound (15 mg).
MS (ESI+): [M+H]$^+$ 420.3.
$^1$H NMR (400 MHz, DMSO-d$_6$) δ 2.61 (3H, s), 4.07 (3H, s), 5.38 (2H, s), 6.04-6.11 (2H, m), 7.11 (1H, dd, J=9.1, 2.0 Hz), 7.50-7.63 (3H, m), 7.63-7.68 (1H, m), 8.29-8.37 (1H, m).

Example 42

1-(2,3-dimethyl-2H-indazol-5-yl)-4-[(4-fluorobenzyl)oxy]pyridin-2(1H)-one

To a suspension of 1-(2,3-dimethyl-2H-indazol-5-yl)-4-hydroxypyridin-2(1H)-one (500 mg), (4-fluorophenyl)methanol (494 mg) and triphenylphosphine (1.54 g) in tetrahydrofuran (40 ml) was added bis(2-methoxyethyl)azodicarboxylate (1.38 g) at room temperature, and the mixture was stirred at the same temperature overnight. The reaction mixture was diluted with ethyl acetate, washed with water and saturated brine, dried over anhydrous magnesium sulfate, and concentrated under reduced pressure. The obtained residue was purified by silica gel column chromatography (ethyl acetate/methanol) to give the title compound (712 mg).
MS (ESI+): [M+H]$^+$ 364.1.
$^1$H NMR (400 MHz, DMSO-d$_6$) δ 2.62 (3H, s), 4.14 (3H, s), 5.03 (2H, s), 6.06 (1H, dd, J=7.5, 2.6 Hz), 6.09 (1H, d, J=2.5 Hz), 7.12 (2H, t, J=8.6 Hz), 7.21 (1H, dd, J=9.1, 1.7 Hz), 7.32 (LH, d, J=7.5 Hz), 7.43 (2H, dd, J=8.2, 5.5 Hz), 7.54 (1H, d, J=1.0 Hz), 7.70 (1H, d, J=9.0 Hz).

Example 43

1-(2-cyclopropyl-3-methyl-2H-indazol-5-yl)-4-{[4-(trifluoromethyl)thiophen-2-yl]methoxy}pyridin-2(1H)-one A) 2-(chloromethyl)-4-(trifluoromethyl)thiophene Thionyl chloride (4.89 g) was added to [4-(trifluoromethyl)thiophen-2-yl]methanol (500 mg) at room temperature, and the mixture was stirred for 3 hr. The reaction mixture was concentrated, and the obtained residue was purified by silica gel column chromatography (hexane/ethyl acetate) to give the title compound (275 mg).
$^1$H NMR (400 MHz, CDCl$_3$) δ 4.76 (2H, s), 7.22 (1H, s), 7.69 (1H, s).

B) 1-(2-cyclopropyl-3-methyl-2H-indazol-5-yl)-4-{[4-(trifluoromethyl)thiophen-2-yl]methoxy}pyridin-2(1H)-one To a mixture of 1-(2-cyclopropyl-3-methyl-2H-indazol-5-yl)-4-hydroxypyridin-2(1H)-one (200 mg) and 2-(chloromethyl)-4-(trifluoromethyl)thiophene (171 mg) in DMF (4 ml) was added potassium carbonate (118 mg) at room temperature, and the mixture was stirred at the same temperature overnight. The reaction mixture was diluted with ethyl acetate, washed with water and saturated brine, dried over anhydrous magnesium sulfate, and concentrated under reduced pressure. The residue was fractionated by HPLC (C18, mobile phase: water/acetonitrile (containing 0.1% NH$_4$HCO$_3$)), and saturated aqueous sodium hydrogen carbonate solution was added to the obtained fraction. The mixture was extracted with ethyl acetate, dried over anhydrous magnesium sulfate, and concentrated under reduced pressure. The residue was crystallized from methanol-water to give the title compound (152 mg).
MS (ESI+): [M+H]$^+$ 446.3.
$^1$H NMR (400 MHz, DMSO-d$_6$) δ 1.11-1.19 (2H, m), 1.23-1.30 (2H, m), 2.70 (3H, s), 3.88-4.02 (1H, m), 5.38 (2H, s), 6.02-6.11 (2H, m), 7.10 (1H, d, J=9.0 Hz), 7.53 (1H, d, J=9.2 Hz), 7.56-7.62 (2H, m), 7.66 (1H, s), 8.33 (1H, s).

Example 44

1-(2-cyclopropyl-3-methyl-2H-indazol-5-yl)-4-{[5-(trifluoromethyl)thiophen-3-yl]methoxy}pyridin-2(1H)-one A) 4-chloro-1-(2-cyclopropyl-3-methyl-2H-indazol-5-yl)pyridin-2(1H)-one To a suspension of 1-(2-cyclopropyl-3-methyl-2H-indazol-5-yl)-4-hydroxypyridin-2(1H)-one (118 g) in DMF (2 L) was added phosphorus oxychloride (46.9 ml) at room temperature, and the mixture was stirred under an argon atmosphere at an inside temperature of 45° C. for 22 hr. The reaction mixture was poured into ethyl acetate (3 L), and washed with saturated aqueous sodium hydrogen carbonate (1.5 L). The obtained aqueous layer was extracted twice with ethyl acetate (2 L and 1 L). The organic layer was washed with aqueous sodium sulfite solution and saturated brine, dried over anhydrous magnesium sulfate, and concentrated under reduced pressure. The residue was dissolved in a 1:1 mixed solvent (1.1 L) of ethyl acetate and tetrahydrofuran with heating, and the mixture was filtered through NH silica gel (750 g). The eluate was concentrated under reduced pressure, and the obtained residue was solidified with diisopropyl ether to give the title compound (73.2 g).
MS (ESI+): [M+H]$^+$ 300.2.

B) 1-(2-cyclopropyl-3-methyl-2H-indazol-5-yl)-4-{[5-(trifluoromethyl)thiophen-3-yl]methoxy}pyridin-2(1H)-one To a solution of [5-(trifluoromethyl)thiophen-3-yl]methanol (100 g) in DMA (1363 ml) was added potassium tert-butoxide (61.3 g) at 5° C., and the mixture was stirred at the same temperature for 30 min. To the obtained mixture was added 4-chloro-1-(2-cyclopropyl-3-methyl-2H-indazol-5-yl)pyridin-2(1H)-one (136.5 g), and the mixture was stirred at an inside temperature of 70° C. for 1.5 hr. The reaction mixture was cooled to room temperature, water (1.4 L) was added, and the obtained suspension was stirred overnight. The precipitated solid was collected by filtration, and washed with water (2.8 L), ethanol (540 ml) and diisopropyl ether (500 ml) to give the title compound (168.6 g).
MS (ESI+): [M+H]$^+$ 446.0.
$^1$H NMR (400 MHz, DMSO-d$_6$) δ 1.10-1.19 (2H, m), 1.22-1.31 (2H, m), 2.70 (3H, s), 3.96 (1H, tt, J=7.4, 3.7 Hz), 5.16 (2H, s), 6.01 (1H, d, J=2.6 Hz), 6.09 (1H, dd, J=7.6, 2.6 Hz), 7.10 (1H, dd, J=9.1, 1.9 Hz), 7.53 (1H, d, J=9.1 Hz), 7.59 (1H, d, J=7.6 Hz), 7.64-7.67 (1H, m), 7.79-7.83 (1H, m), 8.06 (1H, d, J=1.5 Hz).

Example 45

1-(2-cyclopropyl-3-methyl-2H-indazol-5-yl)-4-{[5-(trifluoromethyl)thiophen-2-yl]methoxy}pyridin-2(1H)-one A) 2-(chloromethyl)-5-(trifluoromethyl)thiophene Thionyl chloride (4.89 g) was added to [5-(trifluoromethyl)thiophen-2-yl]methanol (500 mg) at room temperature, and the mixture was stirred for 3 hr. The reaction mixture was concentrated, and the obtained residue was purified by silica gel column chromatography (hexane/ethyl acetate) to give the title compound (289 mg).
$^1$H NMR (400 MHz, CDCl$_3$) δ 4.77 (2H, s), 7.02-7.06 (1H, m), 7.28-7.32 (1H, m).

B) 1-(2-cyclopropyl-3-methyl-2H-indazol-5-yl)-4-{[5-(trifluoromethyl)thiophen-2-yl]methoxy}pyridin-2(1H)-one To a mixture of 1-(2-cyclopropyl-3-methyl-2H-indazol-5-yl)-4-hydroxypyridin-2(1H)-one (200 mg) and 2-(chloromethyl)-5-(trifluoromethyl)thiophene (171 mg) in DMF (4 ml) was added potassium carbonate (118 mg) at room temperature, and the mixture was stirred at the same temperature overnight. The reaction mixture was diluted with ethyl acetate, washed with water and saturated brine, dried over anhydrous magnesium sulfate, and concentrated under reduced pressure. The residue was fractionated by HPLC (C18, mobile phase: water/acetonitrile (containing 0.1% NH$_4$HCO$_3$)), and saturated aqueous sodium hydrogen carbonate solution was added to the obtained fraction. The mixture was extracted with ethyl acetate, dried over anhydrous magnesium sulfate, and concentrated under reduced pressure. The residue was crystallized from methanol-water to give the title compound (138 mg).
MS (ESI+): [M+H]$^+$ 446.2.

¹H NMR (400 MHz, DMSO-d₆) δ 1.11-1.18 (2H, m), 1.25-1.30 (2H, m), 2.70 (3H, s), 3.96 (1H, tt, J=7.3, 3.8 Hz), 5.44 (2H, s), 6.04-6.11 (2H, m), 7.10 (1H, dd, J=9.2, 1.8 Hz), 7.38 (1H, d, J=3.1 Hz), 7.53 (1H, d, J=9.0 Hz), 7.60 (1H, d, J=7.5 Hz), 7.66 (1H, d, J=1.6 Hz), 7.68 (1H, d, J=3.4 Hz).

Example 46

1-(2-cyclopropyl-3-methyl-2H-indazol-5-yl)-4-{[2-(trifluoromethyl)-1,3-thiazol-4-yl]methoxy}pyridin-2(1H)-one A) 4-(chloromethyl)-2-(trifluoromethyl)thiazole Thionyl chloride (4.89 g) was added to [2-(trifluoromethyl)thiazol-4-yl]methanol (512 mg) at room temperature, and the mixture was stirred for 3 hr. The reaction mixture was concentrated to give the title compound (342 mg).
¹H NMR (400 MHz, CDCl₃) δ 4.75 (2H, s), 7.59 (1H, s).

B) 1-(2-cyclopropyl-3-methyl-2H-indazol-5-yl)-4-{[2-(trifluoromethyl)-1,3-thiazol-4-yl]methoxy}pyridin-2(1H)-one To a mixture of 1-(2-cyclopropyl-3-methyl-2H-indazol-5-yl)-4-hydroxypyridin-2(1H)-one (200 mg) and 4-(chloromethyl)-2-(trifluoromethyl)thiazole (172 mg) in DMF (4 ml) was added potassium carbonate (118 mg) at room temperature, and the mixture was stirred at the same temperature overnight. The reaction mixture was diluted with ethyl acetate, washed with water and saturated brine, dried over anhydrous magnesium sulfate, and concentrated under reduced pressure. The residue was fractionated by HPLC (C18, mobile phase: water/acetonitrile (containing 0.1% NH₄HCO₃)), and saturated aqueous sodium hydrogen carbonate solution was added to the obtained fraction. The mixture was extracted with ethyl acetate, dried over anhydrous magnesium sulfate, and concentrated under reduced pressure. The residue was crystallized from methanol-water to give the title compound (141 mg).
MS (ESI+): [M+H]⁺ 447.2.
¹H NMR (400 MHz, DMSO-d₆) δ 1.10-1.19 (2H, m), 1.21-1.30 (2H, m), 2.70 (3H, s), 3.97 (1H, td, J=7.4, 3.4 Hz), 5.32 (2H, s), 6.04-6.16 (2H, m), 7.10 (1H, dd, J=8.9, 1.6 Hz), 7.53 (1H, d, J=9.2 Hz), 7.60 (1H, d, J=7.5 Hz), 7.66 (1H, s), 8.33 (1H, s).

Example 47

1-(2-cyclopropyl-3-methyl-2H-indazol-5-yl)-4-{[5-(trifluoromethyl)thiophen-3-yl]methoxy}pyridin-2(1H)-one 1-(2-Cyclopropyl-3-methyl-2H-indazol-5-yl)-4-{[5-(trifluoromethyl)thiophen-3-yl]methoxy}pyridin-2(1H)-one (337.3 g) obtained by the method shown in Example 44 was dissolved in DMSO (1690 ml) and ethanol (840 ml) at an inside temperature of 70-75° C., and water (840 ml) was added at the same temperature. The obtained suspension was cooled to 35° C., and the obtained solid was collected by filtration. The obtained solid was dissolved in methyl ethyl ketone (5323 ml) at an inside temperature of 70° C., heptane (2500 ml) was added at the same temperature, and the mixture was cooled to room temperature. The obtained solid was collected by filtration, and dried under reduced pressure to give the title compound (268 g).

The obtained solid (266.2 g) was passed through a sieve having a mesh opening of 1 mm, and pulverized by JET MILL 70AS (Powrex) to give 236 g of the title compound.
MS (ESI+): [M+H]⁺ 446.0.
¹H NMR (400 MHz, DMSO-d₆) δ 1.10-1.19 (2H, m), 1.22-1.31 (2H, m), 2.70 (3H, s), 3.96 (1H, tt, J=7.4, 3.7 Hz), 5.16 (2H, s), 6.01 (1H, d, J=2.6 Hz), 6.09 (1H, dd, J=7.6, 2.6 Hz), 7.10 (1H, dd, J=9.1, 1.9 Hz), 7.53 (1H, d, J=9.1 Hz), 7.59 (1H, d, J=7.6 Hz), 7.64-7.67 (1H, m), 7.79-7.83 (1H, m), 8.06 (1H, d, J=1.5 Hz).
Anal calcd for C₂₂H₁₈F₃N₃O₂S: C, 59.32; H, 4.07; N, 9.43. Found C, 59.39; H, 4.22; N, 9.52.
X-ray powder diffraction pattern with specific peaks at d value (or d-spacing)=19.62±0.5, 5.86±0.1, 5.68±0.1, 5.39±0.1, 5.26±0.1, 4.88±0.1, 4.34±0.1, 4.16±0.1, 3.89±0.1, 3.78±0.1, 3.41±0.1, 2.94±0.1 and 2.78±0.1 Å.
Melting point: 216-219° C. (DSC, heating rate: 5° C./min)

Example 48

1-(2-cyclopropyl-3-methyl-2H-indazol-5-yl)-4-{[5-(trifluoromethyl)thiophen-3-yl]methoxy}pyridin-2(1H)-one To a solution of [5-(trifluoromethyl)thiophen-3-yl]methanol (158 g) in DMA (1500 ml) was added potassium tert-butoxide (97 g) at an inside temperature of 10° C., and the mixture was stirred at the same temperature for 15 min. To the obtained mixture were added 4-chloro-1-(2-cyclopropyl-3-methyl-2H-indazol-5-yl)pyridin-2(1H)-one (216 g) and DMA (0.5 ml), and the mixture was stirred at an inside temperature of 70° C. for 1 hr. The reaction mixture was cooled to room temperature and water (2.0 L) was added dropwise. The obtained suspension was stirred overnight. The precipitated solid was collected by filtration, and washed with water (1.5 L), ethanol (800 ml) and diisopropyl ether (1000 ml) to give a crude product (282 g). The obtained crude product was dissolved in DMSO (1400 ml) and ethanol (700 ml) at an inside temperature of 70° C., and water (700 ml) was added at the same temperature. The obtained suspension was cooled to 35° C., and the obtained solid was collected by filtration and washed successively with a DMSO/water mixed solvent (2:8), water, ethanol and diisopropyl ether to give a white solid (264 g).

The solid (358.8 g) obtained by the above-mentioned method was dissolved in methyl ethyl ketone (7894 ml) at an inside temperature of 75° C., and cooled to room temperature by stirring overnight. The obtained suspension was stirred under ice-cooling for 1 hr, and the obtained solid was collected by filtration. The obtained solid was washed successively with methyl ethyl ketone (300 ml) and heptane (500 ml), and dried under reduced pressure to give the title compound (311 g).

The obtained solid (310.7 g) was passed through a sieve having a mesh opening of 1 mm, and pulverized by JET MILL 70AS (Powrex) to give 290.3 g of the title compound.
MS (ESI+): [M+H]⁺ 446.0.
¹H NMR (400 MHz, DMSO-d₆) δ 1.12-1.19 (2H, m), 1.27 (2H, brs), 2.70 (3H, s), 3.96 (1H, d, J=3.3 Hz), 5.16 (2H, s), 6.01 (1H, s), 6.09 (1H, d, J=7.7 Hz), 7.10 (1H, d, J=9.0 Hz), 7.53 (1H, d, J=9.2 Hz), 7.59 (1H, d, J=7.4 Hz), 7.65 (1H, s), 7.81 (1H, s), 8.06 (1H, s).
Anal calcd for C₂₂H₁₈F₃N₃O₂S: C, 59.32; H, 4.07; N, 9.43. Found C, 59.36; H, 4.05; N, 9.46.
X-ray powder diffraction pattern with specific peaks at d value (or d-spacing)=20.34±0.5, 12.51±0.1, 11.41±0.1, 8.52±0.1, 6.86±0.1, 6.28±0.1, 5.15±0.1, 4.94±0.1, 4.29±0.1, 4.21±0.1, 4.12±0.1, 4.08±0.1, 3.72±0.1, 3.43±0.1 and 2.57±0.1 Å.
Melting point: 216-219° C. (DSC, heating rate: 5° C./min)

TABLE 1-A

| Ex. No. | IUPAC Name | Structure | MS |
|---|---|---|---|
| 1 | 4-[(4-chlorobenzyl)oxy]-1-(2,3-dimethyl-2H-indazol-5-yl)pyridin-2(1H)-one | 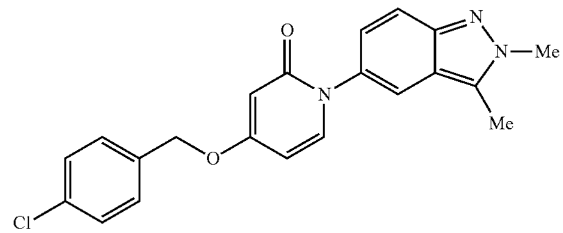 [SMILES: Cc1c2cc(-n3ccc(OCc4ccc(Cl)cc4)cc3=O)ccc2nn1C] | 380.3 |
| 2 | 4-[(4-chlorobenzyl)oxy]-1-(2-ethyl-3-methyl-2H-indazol-5-yl)pyridin-2(1H)-one | 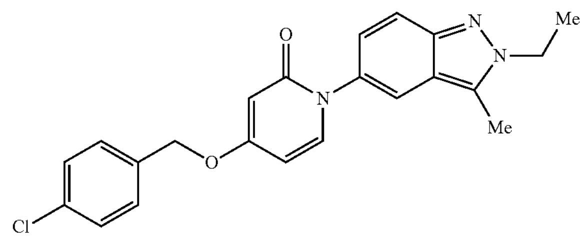 [SMILES: CCn1nc2ccc(-n3ccc(OCc4ccc(Cl)cc4)cc3=O)cc2c1C] | 394.2 |
| 3 | 4-[(4-chlorobenzyl)oxy]-1-(3-methyl-2-propyl-2H-indazol-5-yl)pyridin-2(1H)-one | 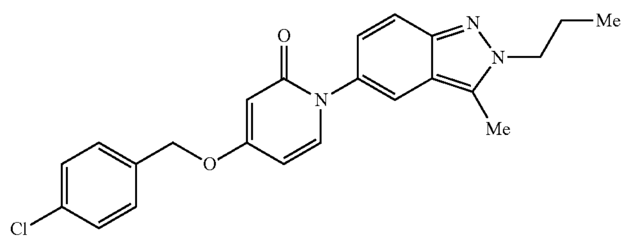 [SMILES: CCCn1nc2ccc(-n3ccc(OCc4ccc(Cl)cc4)cc3=O)cc2c1C] | 408.0 |
| 4 | 1-[(5-{4-[(4-chlorobenzyl)oxy]-2-oxopyridin-1(2H)-yl}-3-methyl-2H-indazol-2-yl)methyl]cyclopropanecarbonitrile | 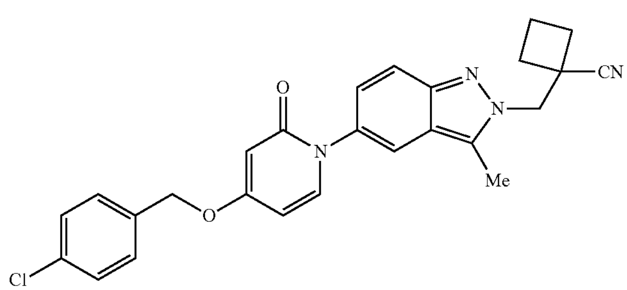 [SMILES: Cc1c2cc(-n3ccc(OCc4ccc(Cl)cc4)cc3=O)ccc2nn1CC1(C#N)CCC1] | 445.2 |
| 5 | 4-[(4-chlorobenzyl)oxy]-1-(2-cyclopropyl-3-methyl-2H-indazol-5-yl)pyridin-2(1H)-one | 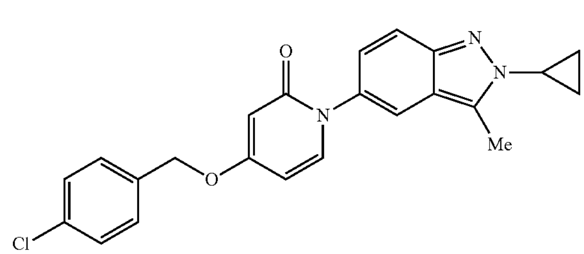 | 406.3 |

TABLE 1-B

| Ex. No. | IUPAC Name | Structure | MS |
|---|---|---|---|
| 6 | 1-(2-cyclopropyl-3-methyl-2H-indazol-5-yl)-4-[(4-fluorobenzyl)oxy]-pyridin-2(1H)-one | 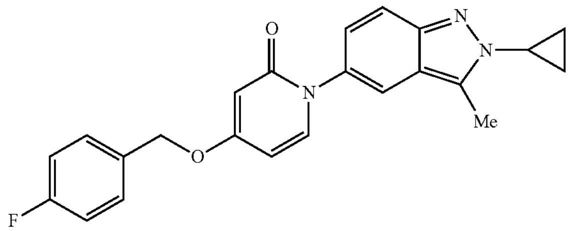 | 390.3 |
| 7 | 4-(benzyloxy)-1-(2-cyclopropyl-3-methyl-2H-indazol-5-yl)pyridin-2(1H)-one | 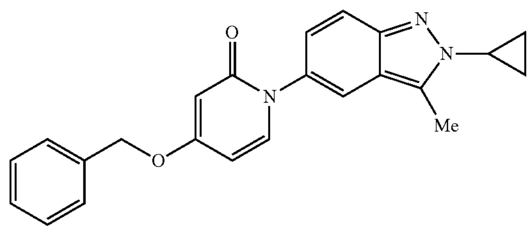 [SMILES: Cc1c2cc(-n3ccc(OCc4ccccc4)cc3=O)ccc2nn1C1CC1] | 372.3 |
| 8 | 4-[(5-chlorothiophen-2-yl)methoxy]-1-(2-cyclopropyl-3-methyl-2H-indazol-5-yl)pyridin-2(1H)-one | 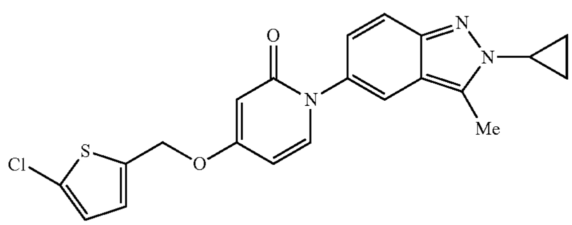 [SMILES: Cc1c2cc(-n3ccc(OCc4ccc(Cl)s4)cc3=O)ccc2nn1C1CC1] | 412.3 |
| 9 | 4-(benzyloxy)-1-(2,3-dimethyl-2H-indazol-5-yl)pyridin-2(1H)-one | 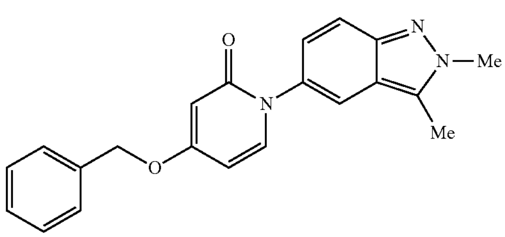 [SMILES: Cc1c2cc(-n3ccc(OCc4ccccc4)cc3=O)ccc2nn1C] | 346.3 |
| 10 | 1-(2,3-dimethyl-2H-indazol-5-yl)-4-{[5-(trifluoromethyl)-thiophen-2-yl]methoxy}pyridin-2(1H)-one | 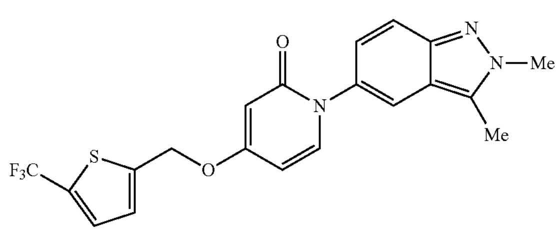 [SMILES: Cc1c2cc(-n3ccc(OCc4ccc(C(F)(F)F)s4)cc3=O)ccc2nn1C] | 420.3 |

TABLE 1-C

| Ex. No. | IUPAC Name | Structure | MS |
|---|---|---|---|
| 11 | 4-[(4-chlorobenzyl)oxy]-1-{3-methyl-2-[(3-methyloxetan-3-yl)methyl]-2H-indazol-5-yl}pyridin-2(1H)-one | 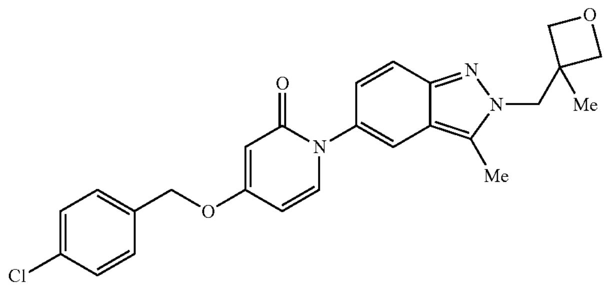 [SMILES: Cc1c2cc(-n3ccc(OCc4ccc(Cl)cc4)cc3=O)ccc2nn1CC1(C)COC1] | 450.0 |
| 12 | 4-[(3-chlorobenzyl)oxy]-1-(2,3-dimethyl-2H-indazol-5-yl)pyridin-2(1H)-one | 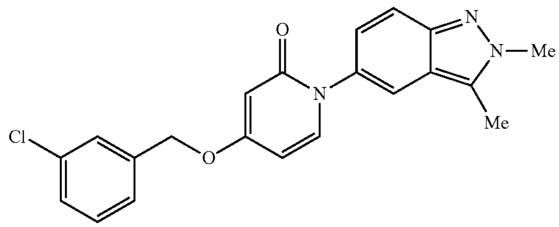 [SMILES: Cc1c2cc(-n3ccc(OCc4cccc(Cl)c4)cc3=O)ccc2nn1C] | 380.1 |
| 13 | 4-{[5-(difluoromethyl)-thiophen-2-yl]methoxy}-1-(2,3-dimethyl-2H-indazol-5-yl)pyridin-2(1H)-one | 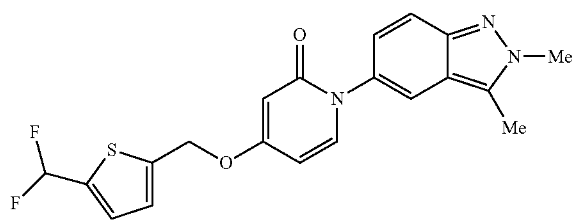 [SMILES: Cc1c2cc(-n3ccc(OCc4ccc(C(F)F)s4)cc3=O)ccc2nn1C] | 402.3 |
| 14 | 4-[(2-chlorobenzyl)oxy]-1-(2,3-dimethyl-2H-indazol-5-yl)pyridin-2(1H)-one | 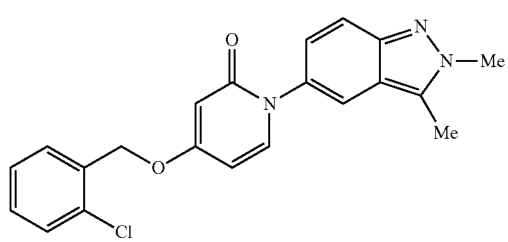 [SMILES: Cc1c2cc(-n3ccc(OCc4ccccc4Cl)cc3=O)ccc2nn1C] | 380.3 |
| 15 | 4-[(3,4-dichlorobenzyl)oxy]-1-(2,3-dimethyl-2H-indazol-5-yl)pyridin-2(1H)-one | 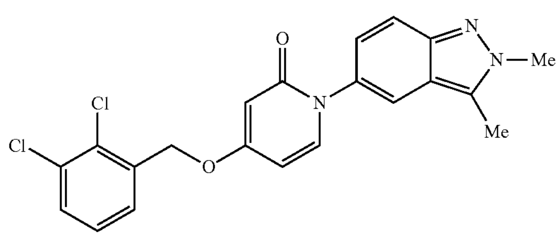 [SMILES: Cc1c2cc(-n3ccc(OCc4cccc(Cl)c4Cl)cc3=O)ccc2nn1C] | 414.3 |

TABLE 1-D

| Ex. No. | IUPAC Name | Structure | MS |
|---|---|---|---|
| 16 | 4-(1-benzofuran-2-ylmethoxy)-1-(2,3-dimethyl-2H-indazol-5-yl)pyridin-2(1H)-one | 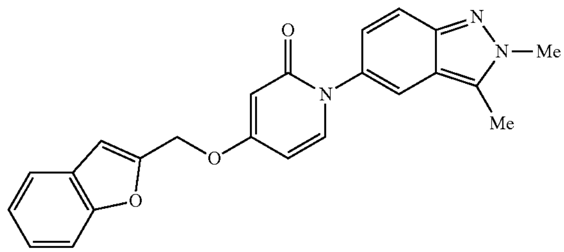 | 386.3 |
| 17 | 4-(1-benzothiophen-2-ylmethoxy)-1-(2,3-dimethyl-2H-indazol-5-yl)pyridin-2(1H)-one | 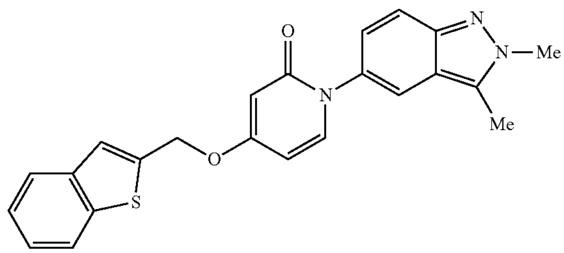 [SMILES: Cc1c2cc(-n3ccc(OCc4cc5ccccc5o4)cc3=O)ccc2nn1C] | 402.1 |
| 18 | 4-[(5-chloropyridin-2-yl)methoxy]-1-(2-cyclopropyl-3-methyl-2H-indazol-5-yl)pyridin-2(1H)-one | 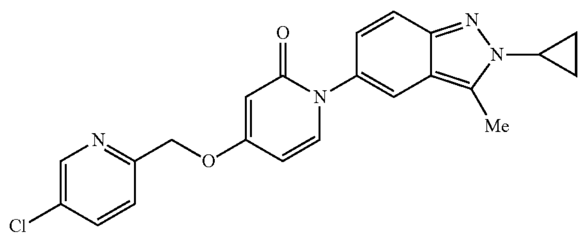 [SMILES: Cc1c2cc(-n3ccc(OCc4ccc(Cl)cn4)cc3=O)ccc2nn1C1CC1] | 407.3 |
| 19 | 1-(2-cyclopropyl-3-methyl-2H-indazol-5-yl)-4-[(5-fluoropyridin-2-yl)methoxy]pyridin-2(1H)-one | 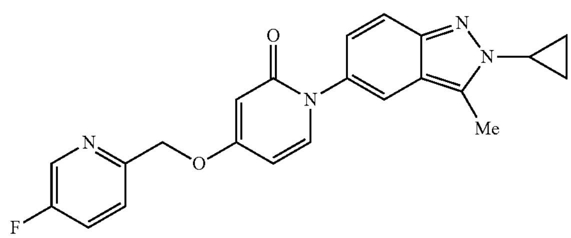 [SMILES: Cc1c2cc(-n3ccc(OCc4ccc(F)cn4)cc3=O)ccc2nn1C1CC1] | 391.3 |
| 20 | 4-[(4-chlorobenzyl)oxy]-1-{2-[2-(2-methoxyethoxy)ethyl]-3-methyl-2H-indazol-5-yl}pyridin-2(1H)-one | 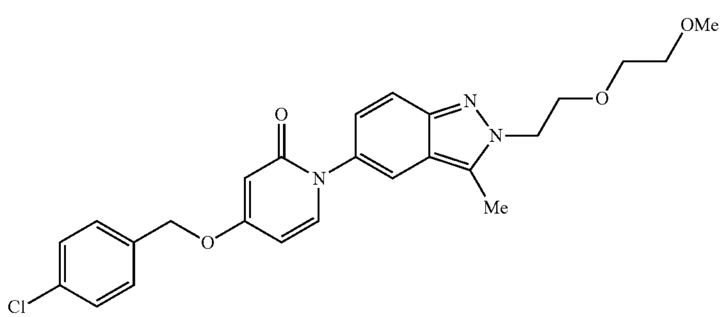 [SMILES: COCCOCCn1nc2ccc(-n3ccc(OCc4ccc(Cl)cc4)cc3=O)cc2c1C] | 468.4 |

TABLE 1-E

| Ex. No. | IUPAC Name | Structure | MS |
|---|---|---|---|
| 21 | 4-[(4-chlorobenzyl)oxy]-1-[2-(2-methoxyethyl)-3-methyl-2H-indazol-5-yl]pyridin-2(1H)-one | 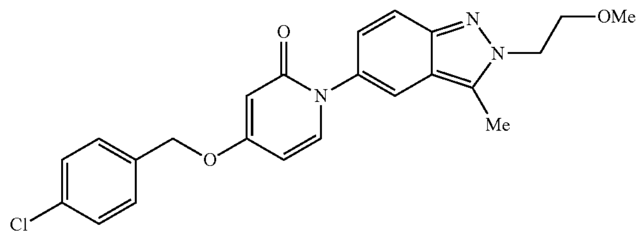 [SMILES: COCCn1nc2ccc(-n3ccc(OCc4ccc(Cl)cc4)cc3=O)cc2c1C] | 424.4 |
| 22 | 1-(2,3-dimethyl-2H-indazol-5-yl)-4-{[5-(trifluoromethyl)-thiophen-3-yl]methoxy}pyridin-2(1H)-one | 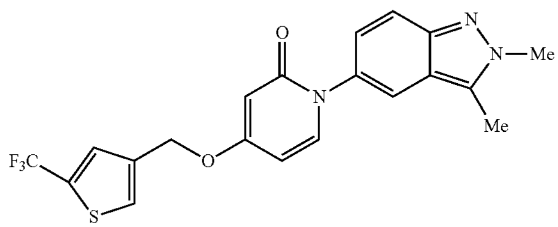 [SMILES: Cc1c2cc(-n3ccc(OCc4csc(C(F)(F)F)c4)cc3=O)ccc2nn1C] | 420.3 |
| 23 | 4-[(5-bromopyridin-2-yl)methoxy]-1-(2,3-dimethyl-2H-indazol-5-yl)pyridin-2(1H)-one | 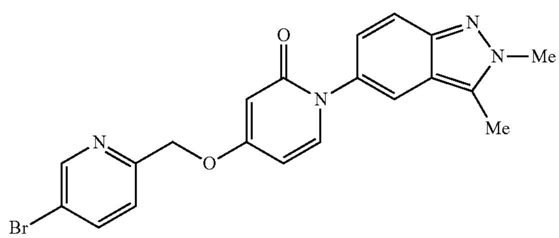 | 425.3 |
| 24 | 4-[(4-tert-butylbenzyl)oxy]-1-(2,3-dimethyl-2H-indazol-5-yl)pyridin-2(1H)-one | 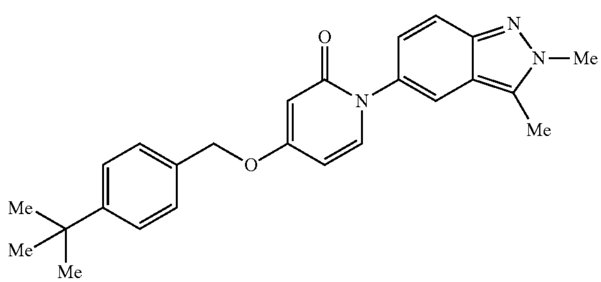 [SMILES: Cc1c2cc(-n3ccc(OCc4ccc(C(C)(C)C)cc4)cc3=O)ccc2nn1C] | 402.4 |
| 25 | 4-[(4-bromobenzyl)oxy]-1-(2,3-dimethyl-2H-indazol-5-yl)pyridin-2(1H)-one | 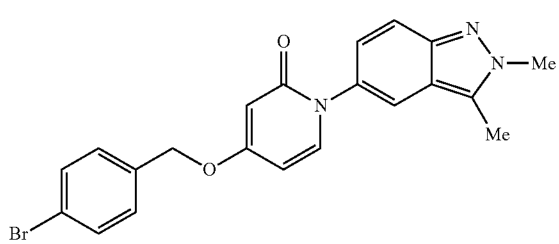 | 424.3 |

TABLE 1-F

| Ex. No. | IUPAC Name | Structure | MS |
|---|---|---|---|
| 26 | 1-(2,3-dimethyl-2H-indazol-5-yl)-4-[(4-isopropylbenzyl)oxy]-pyridin-2(1H)-one | 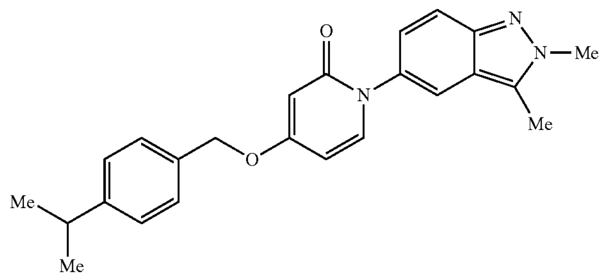 [SMILES: Cc1c2cc(-n3ccc(OCc4ccc(C(C)C)cc4)cc3=O)ccc2nn1C] | 388.3 |
| 27 | 4-[(5-bromothiophen-2-yl)methoxy]-1-(2,3-dimethyl-2H-indazol-5-yl)pyridin-2(1H)-one | 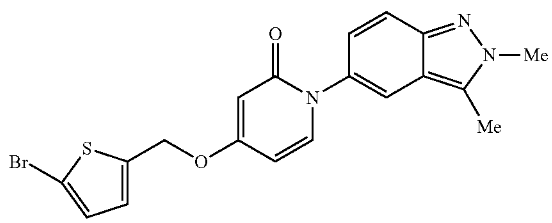 [SMILES: Cc1c2cc(-n3ccc(OCc4ccc(Br)s4)cc3=O)ccc2nn1C] | 430.2 |
| 28 | 4-[(5-bromopyridin-2-yl)methoxy]-1-(2-cyclopropyl-3-methyl-2H-indazol-5-yl)pyridin-2(1H)-one | 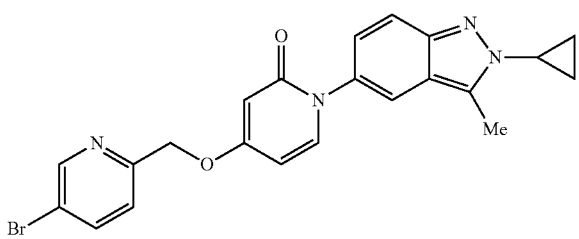 | 452.3 |
| 29 | 4-[(4-chlorophenoxy)methyl]-1-(2,3-dimethyl-2H-indazol-5-yl)pyridin-2(1H)-one | 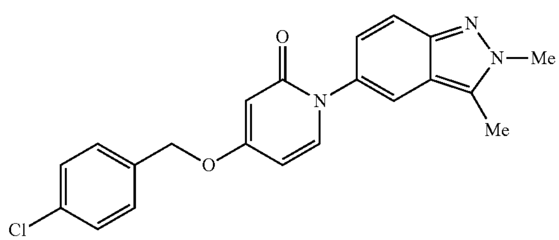 [SMILES: Cc1c2cc(-n3ccc(OCc4ccc(Cl)cc4)cc3=O)ccc2nn1C] | 380.2 |
| 30 | 4-[(4-bromo-1,3-thiazol-2-yl)methoxy]-1-(2,3-dimethyl-2H-indazol-5-yl)pyridin-2(1H)-one | 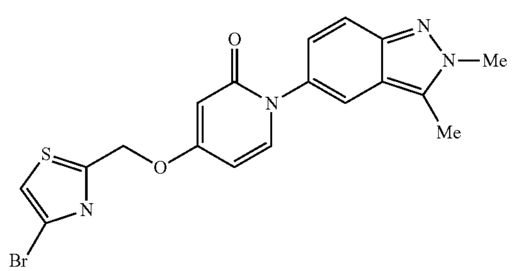 | 432.2 |

TABLE 1-G

| Ex. No. | IUPAC Name | MS |
|---|---|---|
| 31 | 4-[(4-chlorobenzyl)oxy]-1-(6-fluoro-2,3-dimethyl-2H-indazol-5-yl)pyridin-2(1H)-one | 398.3 |
| 32 | 4-[(4-chlorobenzyl)oxy]-1-(4-fluoro-2,3-dimethyl-2H-indazol-5-yl)pyridin-2(1H)-one | 398.3 |
| 33 | 1-(2-cyclopropyl-3-methyl-2H-indazol-5-yl)-4-{[4-(trifluoromethyl)-1,3-thiazol-2-yl]methoxy}pyridin-2(1H)-one | 447.3 |
| 34 | 4-(benzyloxy)-1-(2-ethyl-3-methyl-2H-indazol-5-yl)pyridin-2(1H)-one | 360.2 |
| 35 | 1-(2-ethyl-3-methyl-2H-indazol-5-yl)-4-{[4-(pentafluoro-$\lambda^6$-sulfanyl)benzyl]oxy}-pyridin-2(1H)-one | 486.3 |

TABLE 1-H

| Ex. No. | IUPAC Name | Structure | MS |
|---|---|---|---|
| 36 | 1-(2-ethyl-3-methyl-2H-indazol-5-yl)-4-{[4-(trifluoromethyl)-1,3-thiazol-2-yl]methoxy}pyridin-2(1H)-one | 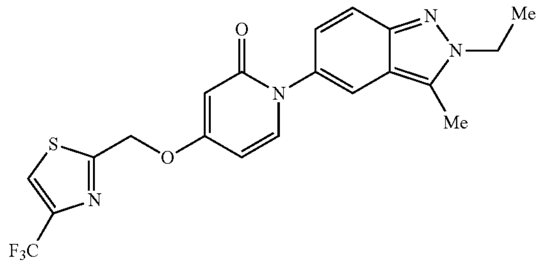 [SMILES: CCn1nc2ccc(-n3ccc(OCc4nc(C(F)(F)F)cs4)cc3=O)cc2c1C] | 435.1 |
| 37 | 1-(2-ethyl-3-methyl-2H-indazol-5-yl)-4-[(4-fluorobenzyl)oxy]-pyridin-2(1H)-one | 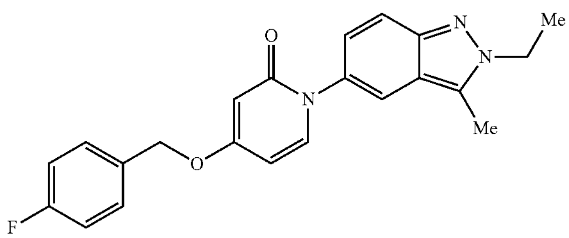 [SMILES: CCn1nc2ccc(-n3ccc(OCc4ccc(F)cc4)cc3=O)cc2c1C] | 378.1 |
| 38 | 1-(2,3-dimethyl-2H-indazol-5-yl)-4-{[4-(trifluoromethyl)-1,3-thiazol-2-yl]methoxy}pyridin-2(1H)-one | 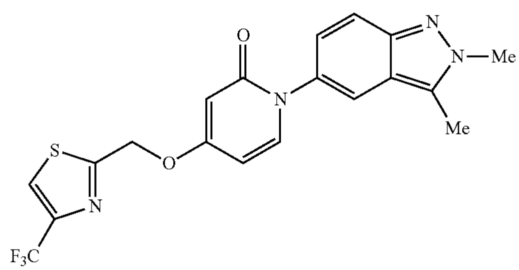 [SMILES: Cc1c2cc(-n3ccc(OCc4nc(C(F)(F)F)cs4)cc3=O)ccc2nn1C] | 421.3 |
| 39 | 1-(2,3-dimethyl-2H-indazol-5-yl)-4-{[2-(trifluoromethyl)-1,3-thiazol-4-yl]methoxy}pyridin-2(1H)-one | 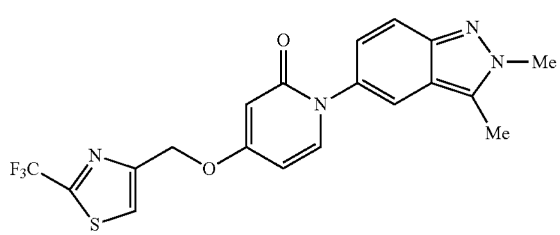 [SMILES: Cc1c2cc(-n3ccc(OCc4csc(C(F)(F)F)n4)cc3=O)ccc2nn1C] | 421.3 |
| 40 | 1-(2,3-dimethyl-2H-indazol-5-yl)-4-{[5-(trifluoromethyl)-pyrazin-2-yl]methoxy}pyridin-2(1H)-one | 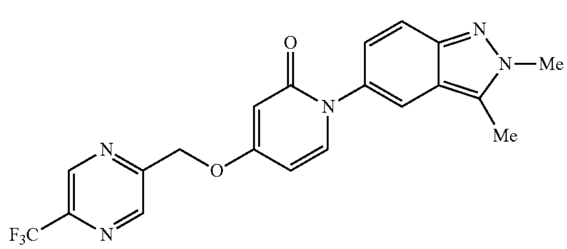 [SMILES: Cc1c2cc(-n3ccc(OCc4cnc(C(F)(F)F)cn4)cc3=O)ccc2nn1C] | 416.1 |

TABLE 1-I

| Ex. No. | IUPAC Name | Structure | MS |
|---|---|---|---|
| 41 | 1-(2,3-dimethyl-2H-indazol-5-yl)-4-{[4-(trifluoromethyl)-thiophen-2-yl]methoxy}pyridin-2(1H)-one | 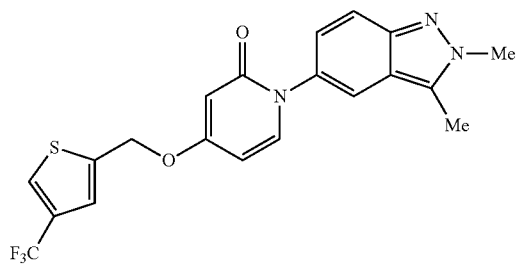 [SMILES: Cc1c2cc(-n3ccc(OCc4cc(C(F)(F)F)cs4)cc3=O)ccc2nn1C] | 420.3 |
| 42 | 1-(2,3-dimethyl-2H-indazol-5-yl)-4-[(4-fluorobenzyl)oxy]-pyridin-2(1H)-one | 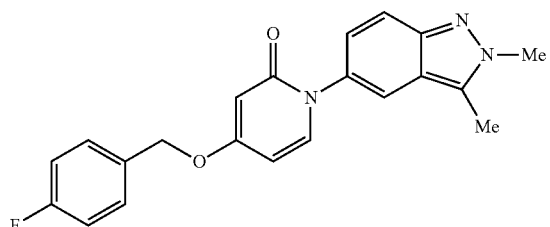 | 364.1 |
| 43 | 1-(2-cyclopropyl-3-methyl-2H-indazol-5-yl)-4-{[4-(trifluoromethyl)-thiophen-2-yl]methoxy}pyridin-2(1H)-one | 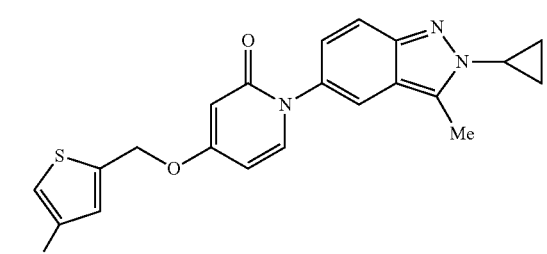 | 446.3 |
| 44 | 1-(2-cyclopropyl-3-methyl-2H-indazol-5-yl)-4-{[5-(trifluoromethyl)-thiophen-3-yl]methoxy}pyridin-2(1H)-one | 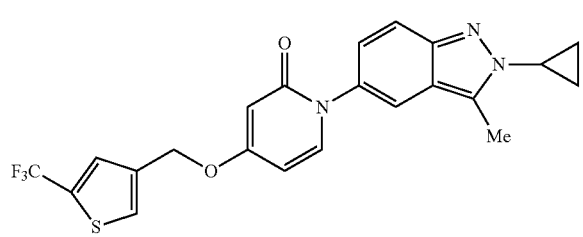 [SMILES: Cc1c2cc(-n3ccc(OCc4csc(C(F)(F)F)c4)cc3=O)ccc2nn1C1CC1] | 446.0 |
| 45 | 1-(2-cyclopropyl-3-methyl-2H-indazol-5-yl)-4-{[5-(trifluoromethyl)-thiophen-2-yl]methoxy}pyridin-2(1H)-one | 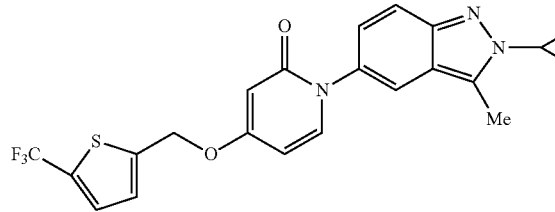 | 446.2 |

TABLE 1-J

| Ex. No. | IUPAC Name | Structure | MS |
|---|---|---|---|
| 46 | 1-(2-cyclopropyl-3-methyl-2H-indazol-5-yl)-4-{[2-(trifluoromethyl)-1,3-thiazol-4-yl]methoxy}pyridin-2(1H)-one | 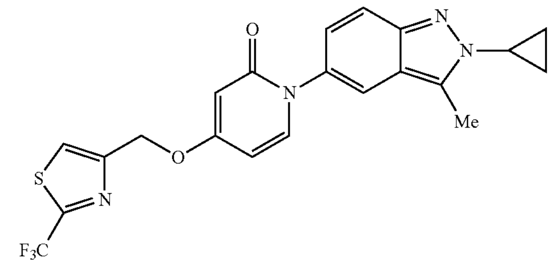 [SMILES: Cc1c2cc(-n3ccc(OCc4csc(C(F)(F)F)n4)cc3=O)ccc2nn1C1CC1] | 447.2 |
| 47 | 1-(2-cyclopropyl-3-methyl-2H-indazol-5-yl)-4-{[5-(trifluoromethyl)-thiophen-3-yl]methoxy}pyridin-2(1H)-one | 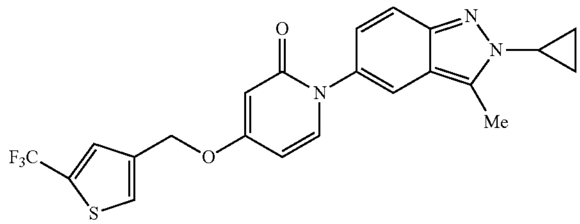 [SMILES: Cc1c2cc(-n3ccc(OCc4csc(C(F)(F)F)c4)cc3=O)ccc2nn1C1CC1] | 446.0 |
| 48 | 1-(2-cyclopropyl-3-methyl-2H-indazol-5-yl)-4-{[5-(trifluoromethyl)-thiophen-3-yl]methoxy}pyridin-2(1H)-one | 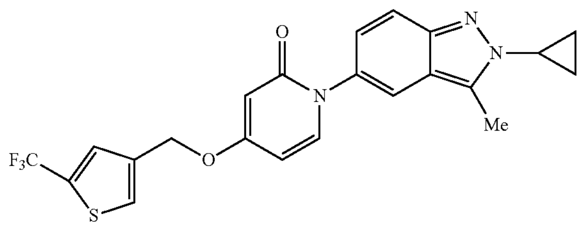 [SMILES: Cc1c2cc(-n3ccc(OCc4csc(C(F)(F)F)c4)cc3=O)ccc2nn1C1CC1] | 446.0 |

Experimental Example 1

Determination of Human MCH Receptor 1 (MCHR1) Competitive Inhibitory Activity of Test Compound Using Binding Assay 1. Preparation of Membrane Fraction Using human MCHR1(=SLC-1 receptor)-expressing CHO cell clone 57 described in WO01/82925, MCHR1-expressing CHO cellular membrane fractions were prepared by the following method.

In phosphate buffered saline (pH 7.4) supplemented with 5 mM EDTA (ethylenediaminetetraacetic acid) were respectively suspended human MCHR1-expressing CHO cells ($1 \times 10^8$ cells) and centrifuged. Homogenate buffer (10 mL, 10 mM NaHCO$_3$, 5 mM EDTA, pH 7.5, 0.5 mM PMSF (phenylmethylsulfonyl fluoride), 20 mg/L leupeptin, 4 mg/L E-64, 1 mg/L pepstatin A) was added to the pellets of the cells and, using Polytron Homogenizer, the mixture was homogenated. The supernatant obtained after centrifugation at 400×g for 10 min was further centrifuged at 100,000×g for 1 hr to give precipitate of the membrane fraction. The precipitate was suspended in 2 mL of assay buffer [20 mM Tris-HCl (pH 7.5), 5 mM EDTA, 0.5 mM PMSF, 20 mg/L leupeptin, 4 mg/L E-64, 1 mg/L pepstatin A]. The membrane fractions were suspended in assay buffer to a protein concentration of 2 mg/mL, and after dispensing, preserved at −80° C. and used upon thawing each time when in use.

2. Binding Assay

The MCHR1 ligand binding inhibitory activity of the test compound was determined as follows.

An MCHR1-expressing CHO cellular membrane fraction (173 μL) diluted with an assay buffer was dispensed to a 96 well polypropylene plate (3363, Corning). DMSO solution (2 μL), 33 μM cold MCH (1-19) diluted with DMSO solution (2 μL), or a test compound solution diluted with DMSO solution to various concentrations (2 μL) was added, and lastly, [$^{125}$I]-MCH (4-19) diluted with assay buffer (hereinafter, sometimes to be referred to as "hot MCH", 25 μL) was added to each well. The mixture was reacted with stirring at room temperature for 1 hr, and the plate was set on FilterMate Harvester (PerkinElmer). Using a polyethyleneimine-treated glass filter plate (GF/C, PerkinElmer), which had been previously set, the plate was suction-filtered and washed three times with washing buffer (50 mM Tris-HCl buffer pH 7.5). The glass filter plate was dried, MicroScint 0 (PerkinElmer) was added at 25 μL/well, and the resulting radioactivity was measured by TopCount liquid scintillation counter (PerkinElmer). The binding inhibition rate of the test compound was calculated by the following formula.

Binding inhibition(%)=100−(radioactivity upon addition of test compound and hot MCH−radioactivity upon addition of cold MCH and hot MCH solution)/(radioactivity upon addition of DMSO solution and hot MCH−radioactivity upon addition of cold MCH and hot MCH solution)×100

The binding inhibition rates (%) of test compounds (0.1 μM) as measured using human MCHR1-expressing CHO cells are shown in Table 2.

TABLE 2

| compound No. | Binding inhibition rate % (0.1 μM) |
|---|---|
| Example 1 | 72 |
| Example 2 | 43 |
| Example 3 | 37 |
| Example 5 | 78 |
| Example 6 | 72 |
| Example 7 | 44 |
| Example 8 | 68 |
| Example 9 | 36 |
| Example 10 | 39 |
| Example 12 | 42 |
| Example 16 | 47 |
| Example 18 | 45 |
| Example 22 | 51 |
| Example 23 | 57 |
| Example 25 | 57 |
| Example 27 | 60 |
| Example 28 | 68 |
| Example 30 | 34 |
| Example 32 | 54 |
| Example 33 | 76 |
| Example 36 | 37 |
| Example 38 | 45 |
| Example 39 | 33 |
| Example 41 | 55 |
| Example 42 | 46 |
| Example 43 | 71 |
| Example 44 | 77 |
| Example 45 | 49 |
| Example 46 | 50 |

As is clear from Table 2, the compound of the present invention has an excellent MCH receptor 1 competitive inhibitory activity.

Experimental Example 2

Measurement of MCH Receptor 1 Antagonistic Activity of Test Compound Using $Ca^{2+}$ Mobilization Assay Using an expression vector plasmid introduced with human MCHR1 gene for expression in animal cells, human MCHR1 gene was introduced into CHO cells (CHO dhfr−) by Lipofectamine LTX (Invitrogen). The cells were cultured in selection MEMα medium [445 mL of MEMα medium without nucleic acid and added with 5 mL of Penicillin-Streptomycin (Invitrogen) and 50 mL of dialyzed fetal bovine serum]. Colony 24 clones grown in the selection medium, which were human MCHR1 gene-expressing CHO cell candidates, were selected. From these clones, clone #4 which showed the highest response to the change of $Ca^{2+}$ concentration on stimulation by the addition of 25 nM ligand MCH (4-19) was selected by $Ca^{2+}$ mobilization assay. In the following test, this human MCHR1-expressing CHO cell (clone #4) was used. An integrated dispensing function fluorometer (CellLux, PerkinElmer) was used for $Ca^{2+}$ mobilization assay. The CHO cells were plated in a 96 well plate (type 3904, Corning) with a black wall and clear well bottom at a density of 20000 cells/well, and cultured in an incubator for about 24 hr at 5% $CO_2$, 37° C. The medium was removed, and the cells were washed with phosphate buffered saline (PBS). A $Ca^{2+}$ indicator dye reagent (DOJINDO LABORATORIES, Ca screening no-wash kit Fluo4) was added at 100 μL/well, and the dye was allowed to penetrate into the cells for 30 min in an incubator at 5% $CO_2$, 37° C. The plate was set on a plate reader. First, a test compound solution diluted with an assay buffer [10 mM HEPES (pH 7.4), 1× assay buffer containing 0.1% BSA (DOJINDO LABORATORIES, attached to Ca screening no-wash kit Fluo4)] or DMSO solution was added at 50 μL/well, and then ligand MCH (4-19) peptide (final concentration 2 nM) diluted with assay buffer or DMSO was added at 50 μL/well, during which changes in intracellular fluorescence were measured at 2 second intervals. The antagonistic activity of the test compound was calculated by the following formula and shown as an inhibition rate (%) wherein the intracellular fluorescence activity resulting from the stimulation by the addition of ligand MCH (4-19) peptide was 100% and that of the well added with DMSO solution alone was 0%.

inhibitory rate(%)=100−[fluorescence activity upon addition of test compound and MCH(4-19)peptide solution− fluorescence activity upon addition of DMSO solution only]/[fluorescence activity upon addition of DMSO solution and MCH(4-19)peptide solution−fluorescence activity upon addition of DMSO solution only]×100

The inhibition rates (%) of test compounds (0.1 μM) as antagonist activity measured using human MCHR1-expressing CHO cells (clone #4) are shown in the following Table 3.

TABLE 3

| compound No. | Inhibition rate % (0.1 μM) |
|---|---|
| Example 1 | 83 |
| Example 2 | 73 |
| Example 5 | 86 |
| Example 6 | 70 |
| Example 7 | 66 |
| Example 8 | 55 |
| Example 10 | 51 |
| Example 12 | 38 |
| Example 16 | 57 |
| Example 18 | 63 |
| Example 22 | 69 |
| Example 23 | 77 |
| Example 25 | 84 |
| Example 27 | 92 |
| Example 28 | 93 |
| Example 30 | 89 |
| Example 33 | 96 |
| Example 36 | 83 |
| Example 38 | 78 |
| Example 39 | 71 |
| Example 41 | 70 |
| Example 42 | 65 |
| Example 43 | 72 |
| Example 44 | 55 |
| Example 45 | 43 |
| Example 46 | 78 |

As is clear from Table 3, the compound of the present invention has an excellent MCH receptor 1 antagonistic activity.

Experimental Example 3

Evaluation of Anorectic Effect Using Male Diet-Induced Obese F344/Jcl Rats

Male diet-induced obese F344/Jcl rats (41-52 weeks old) fed with a high-fat diet (D12451: Research Diets) from 5 weeks old were used. From before the start of experiment, the rats were singly housed, given a powder high-fat diet (D12451M: Research Diets), and habituated to oral administration with tap water. The food intake from the evening of the day before the start of experiment to the next morning was measured, and the rats were grouped based on both the food intake and the body weight of the previous day. In the evening of the day of the start of experiment and the next day, 0.5% methylcellulose solution was orally administered to the control group, and 0.5% methylcellulose suspension of the test compound (5 mg/mL) was orally administered to the compound administration group at 2 mL/kg (6 per group for both control group and compound administration group). The food intake for 2 days from the initial administration was measured. The food intake inhibition rate of each compound administration group to the control group was calculated. The results are shown in Table 4.

TABLE 4

| compound No. | Food intake suppression rate (%) |
|---|---|
| Example 1 | 32.1 |
| Example 6 | 26.4 |
| Example 22 | 50.7 |
| Example 25 | 59.8 |
| Example 44 | 30.6 |
| Example 46 | 13.3 |

As is clear from Table 4, the compound of the present invention was shown to have an excellent anoretic effect.

Experimental Example 4 hERG Activity Measurement by IonWorks Quattro

A cell strain CYL3038 having hERG stably expressed in CHO cells was purchased from Millipore LIMITED. A subculture of CYL3038 was prepared using Ham's F-12 medium containing 10% FBS and 500 µg/mL Geneticin, under the presence of 5% $CO_2$ at 32° C. hERG current inhibition was measured by PPC mode of IonWorks Quattro (Molecular Devices, Inc.). As an extracellular fluid, PBS (+) was used. As an intracellular fluid, 20 mM HEPES buffer (pH 7.3) containing 140 mM KCl, 2 mM $MgCl_2$ and 1 mM EGTA was used, and the cell was perforated by amphotericin. As the voltage protocol, holding potential was set to −80 mV, prepulsevoltage was set to 40 mV (2 seconds) and test pulsevoltage was set to −50 mV (2 seconds). Current values before and after addition of compound are respectively recorded as pre-compound hERG current and post-compound hERG current. Exposure time for the compound was set to 5 minutes. hERG current inhibition rate (%) was calculated based on the equation as shown below. The results are shown in Table 5.

% hERG inhibition=100−(post-compound hERG current/pre-compound hERG current)×100

TABLE 5

| compound No. | % hERG inhibition (10 µM) |
|---|---|
| Example 1 | 22.1 |
| Example 44 | 5.7 |
| Example 46 | 16.8 |

As is clear from Table 5, the compounds showed hERG inhibitory activity of as low as less than 25% in this measurement, and were confirmed to be low toxic.

Formulation Example 1

| (1) | Compound of Example 1 | 50 mg |
| (2) | Lactose | 34 mg |
| (3) | Cornstarch | 10.6 mg |
| (4) | Cornstarch (paste) | 5 mg |
| (5) | Magnesium stearate | 0.4 mg |
| (6) | Calcium carboxymethylcellulose | 20 mg |
| | Total | 120 mg |

The above-mentioned (1) to (6) are mixed according to a conventional method and the mixture is tableted by a tableting machine to give a tablet.

Formulation Example 2

| (1) | Compound of Example 1 | 30 mg |
| (2) | Crystalline cellulose | 10 mg |
| (3) | Lactose | 19 mg |
| (4) | Magnesium stearate | 1 mg |
| | Total | 60 mg |

(1), (2), (3) and (4) are mixed and filled in a gelatin capsule to give a capsule.

INDUSTRIAL APPLICABILITY

Compound (I) has a melanin-concentrating hormone (MCH) receptor antagonistic action, and is low toxic. Therefore, the compound is highly useful as an anorexigenic agent and an agent for the prophylaxis or treatment of obesity and the like.

This application is based on a patent application No. 2013-143940 filed in Japan, the contents of which are incorporated by reference in full herein.

The invention claimed is:
1. A compound represented by formula (I):

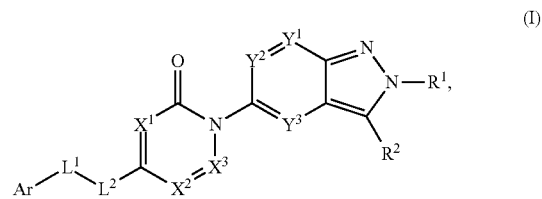

wherein ring Ar is an aromatic ring optionally further substituted;
$L^1$ is O, $S(O)_{m1}$, $NR^{3A}$ or $CR^{3B}R^{3C}$;
$L^2$ is O, $S(O)_{m2}$, $NR^{4A}$ or $CR^{4B}R^{4C}$;
(excluding the combination of $L^1$ being other than $CR^{3B}R^{3C}$ and $L^2$ being other than $CR^{4B}R^{4C}$)
m1 and m2 are each independently an integer of 0 to 2;
$R^{3A}$ and $R^{4A}$ are each independently a hydrogen atom or an optionally substituted hydrocarbon group;
$R^{3B}$, $R^{3C}$, $R^{4B}$ and $R^{4C}$ are each independently a hydrogen atom or a substituent;

when $L^1$ is $CR^{3B}R^{3C}$ and ring Ar has substituent(s), $R^{3B}$ and the substituent are optionally bonded to each other to form an optionally substituted ring;

$X^1$, $X^2$ and $X^3$ are each independently $CR^5$ or N;

$R^5$ is a hydrogen atom, a halogen atom, a cyano group, an optionally substituted $C_{1-6}$ alkyl group, an optionally substituted $C_{1-6}$ alkoxy group or an optionally substituted $C_{3-10}$ cycloalkyl group;

$R^1$ is an optionally substituted $C_{1-6}$ alkyl group or an optionally substituted cyclic group;

$R^2$ is a halogen atom, an optionally substituted $C_{1-6}$ alkyl group or an optionally substituted cyclic group;

$Y^1$, $Y^2$ and $Y^3$ are each independently $CR^6$ or N; and $R^6$ is a hydrogen atom, a halogen atom, an optionally substituted $C_{1-6}$ alkyl group, an optionally substituted $C_{1-6}$ alkoxy group or an optionally substituted $C_{3-10}$ cycloalkyl group, or a salt thereof.

2. The compound according to claim 1, wherein ring Ar is a $C_{6-14}$ aromatic hydrocarbon ring or a 5- to 10-membered aromatic heterocycle, each of which is optionally further substituted by 1 to 3 substituents selected from the group consisting of:
(a) a halogen atom,
(b) a $C_{1-6}$ alkyl group optionally substituted by 1 to 3 halogen atoms,
(c) a $C_{1-6}$ alkoxy group optionally substituted by 1 to 3 halogen atoms, and
(d) a pentafluorosulfanyl group,
or a salt thereof.

3. The compound according to claim 1, wherein $L^1$ is $CH_2$; and $L^2$ is O, or a salt thereof.

4. The compound according to claim 1, wherein $X^1$, $X^2$ and $X^3$ are CH, or a salt thereof.

5. The compound according to claim 1, wherein $R^1$ is a $C_{1-6}$ alkyl group or a $C_{3-10}$ cycloalkyl group, or a salt thereof.

6. The compound according to claim 1, wherein $R^2$ is a $C_{1-6}$ alkyl group, or a salt thereof.

7. The compound according to claim 1, wherein $Y^1$, $Y^2$ and $Y^3$ are CH, or a salt thereof.

8. The compound according to claim 1, wherein ring Ar is a $C_{6-14}$ aromatic hydrocarbon ring or a 5- to 10-membered aromatic heterocycle, each of which is optionally further substituted by 1 to 3 substituents selected from the group consisting of:
(a) a halogen atom,
(b) a $C_{1-6}$ alkyl group optionally substituted by 1 to 3 halogen atoms,
(c) a $C_{1-6}$ alkoxy group optionally substituted by 1 to 3 halogen atoms, and
(d) a pentafluorosulfanyl group,
$L^1$ is $CH_2$,
$L^2$ is O,
$X^1$, $X^2$ and $X^3$ are CH,
$R^1$ is a $C_{1-6}$ alkyl group or a $C_{3-10}$ cycloalkyl group,
$R^2$ is a $C_{1-6}$ alkyl group, and
$Y^1$, $Y^2$ and $Y^3$ are CH, or a salt thereof.

9. 4-[(4-Chlorobenzyl)oxy]-1-(2,3-dimethyl-2H-indazol-5-yl)pyridin-2(1H)-one or a salt thereof.

10. 1-(2-Cyclopropyl-3-methyl-2H-indazol-5-yl)-4-{[5-(trifluoromethyl)thiophen-3-yl]methoxy}pyridin-2(1H)-one or a salt thereof.

11. 1-(2-Cyclopropyl-3-methyl-2H-indazol-5-yl)-4-{[2-(trifluoromethyl)-1,3-thiazol-4-yl]methoxy}pyridin-2(1H)-one or a salt thereof.

12. A pharmaceutical composition comprising the compound according to claim 1, or a salt thereof, and a pharmacologically acceptable carrier.

13. The pharmaceutical composition according to claim 12, which is a melanin-concentrating hormone receptor antagonist.

14. The pharmaceutical composition according to claim 12, which is an anorexigenic agent.

15. The pharmaceutical composition according to claim 12, which is a prophylactic or therapeutic agent for obesity.

16. A method of preventing or treating obesity in a mammal, comprising administering an effective amount of the compound according to claim 1 or a salt thereof to the mammal.

17. A method of antagonizing a melanin-concentrating hormone receptor in a mammal, comprising administering an effective amount of the compound according to claim 1 or a salt thereof to the mammal.

18. A method of suppressing food intake in a mammal, comprising administering an effective amount of the compound according to claim 1 or a salt thereof to the mammal.

19. The compound according to claim 1 or a salt thereof for use in the prophylaxis or treatment of obesity.

20. The compound according to claim 1 or a salt thereof for use in the suppression of food intake.

\* \* \* \* \*